US009259735B2

(12) United States Patent
Handique et al.

(10) Patent No.: US 9,259,735 B2
(45) Date of Patent: Feb. 16, 2016

(54) METHODS AND SYSTEMS FOR CONTROL OF MICROFLUIDIC DEVICES

(71) Applicant: HandyLab, Inc., Franklin Lakes, NJ (US)

(72) Inventors: Kalyan Handique, Ann Arbor, MI (US); Karthik Ganesan, Ann Arbor, MI (US); Sundaresh N. Brahmasandra, Ann Arbor, MI (US)

(73) Assignee: HandyLab, Inc., Franklin Lakes, NJ (US)

( * ) Notice: Subject to any disclaimer, the term of this patent is extended or adjusted under 35 U.S.C. 154(b) by 34 days.

(21) Appl. No.: 14/317,356

(22) Filed: Jun. 27, 2014

(65) Prior Publication Data

US 2014/0377850 A1  Dec. 25, 2014

Related U.S. Application Data

(63) Continuation of application No. 13/925,046, filed on Jun. 24, 2013, now Pat. No. 8,768,517, which is a continuation of application No. 13/189,453, filed on Jul. 22, 2011, now Pat. No. 8,473,104, which is a (Continued)

(51) Int. Cl.
*B01L 7/00* (2006.01)
*B01F 13/00* (2006.01)
(Continued)

(52) U.S. Cl.
CPC .............. *B01L 7/52* (2013.01); *B01F 13/0071* (2013.01); *B01F 13/0079* (2013.01);
(Continued)

(58) Field of Classification Search
CPC .............. B01L 7/52; B01L 2300/1827; B01L 2400/0677; B01L 2400/0487; B01L 3/502738; B01L 3/502723; B01L 2200/0684; B01L 2200/147; B01L 2300/0816; B01L 2300/087; B01L 2300/0887; B01L 2300/1822
See application file for complete search history.

(56) References Cited

U.S. PATENT DOCUMENTS 1,434,314 A   10/1922   Raich
1,616,419 A    2/1927   Wilson
(Continued)

FOREIGN PATENT DOCUMENTS

CA   2294819   1/1999
CN   103540518  1/2014
(Continued)

OTHER PUBLICATIONS

Kuo et al., "Remnant cationic dendrimers block RNA migration in electrophoresis after monophasic lysis", J Biotech. (2007) 129: 383-390.
(Continued)

*Primary Examiner* — Sally Merkling
(74) *Attorney, Agent, or Firm* — Knobbe, Martens, Olson & Bear, LLP

(57) ABSTRACT

The present invention provides control methods, control systems, and control software for microfluidic devices that operate by moving discrete micro-droplets through a sequence of determined configurations. Such microfluidic devices are preferably constructed in a hierarchical and modular fashion which is reflected in the preferred structure of the provided methods and systems. In particular, the methods are structured into low-level device component control functions, middle-level actuator control functions, and high-level micro-droplet control functions. Advantageously, a microfluidic device may thereby be instructed to perform an intended reaction or analysis by invoking micro-droplet control function that perform intuitive tasks like measuring, mixing, heating, and so forth. The systems are preferably programmable and capable of accommodating microfluidic devices controlled by low voltages and constructed in standardized configurations. Advantageously, a single control system can thereby control numerous different reactions in numerous different microfluidic devices simply by loading different easily understood micro-droplet programs.

15 Claims, 22 Drawing Sheets

Related U.S. Application Data continuation of application No. 11/251,188, filed on Oct. 13, 2005, now Pat. No. 7,987,022, which is a continuation of application No. 09/819,105, filed on Mar. 28, 2001, now Pat. No. 7,010,391.

(51) Int. Cl.

| | | |
|---|---|---|
| B01J 19/00 | (2006.01) | |
| B01L 3/00 | (2006.01) | |
| G01N 1/40 | (2006.01) | |
| G01N 35/10 | (2006.01) | |

(52) U.S. Cl.
CPC ...... *B01J 19/0093* (2013.01); *B01L 3/502784* (2013.01); *B01L 3/502792* (2013.01); *G01N 1/4077* (2013.01); *G01N 35/1083* (2013.01); *B01J 2219/0086* (2013.01); *B01J 2219/0097* (2013.01); *B01J 2219/00783* (2013.01); *B01J 2219/00828* (2013.01); *B01J 2219/00831* (2013.01); *B01J 2219/00833* (2013.01); *B01J 2219/00835* (2013.01); *B01J 2219/00837* (2013.01); *B01J 2219/00862* (2013.01); *B01J 2219/00873* (2013.01); *B01J 2219/00889* (2013.01); *B01J 2219/00891* (2013.01); *B01J 2219/00936* (2013.01); *B01J 2219/00943* (2013.01); *B01J 2219/00945* (2013.01); *B01J 2219/00961* (2013.01); *B01J 2219/00986* (2013.01); *B01L 2200/0605* (2013.01); *B01L 2200/0673* (2013.01); *B01L 2200/14* (2013.01); *B01L 2300/0816* (2013.01); *B01L 2400/0442* (2013.01); *B01L 2400/0493* (2013.01); *B01L 2400/0677* (2013.01); *Y10T 436/12* (2015.01); *Y10T 436/25* (2015.01); *Y10T 436/2575* (2015.01)

(56) References Cited

U.S. PATENT DOCUMENTS

| | | |
|---|---|---|
| 1,733,401 A | 8/1930 | Lovekin |
| D189,404 S | 12/1960 | Nicolle |
| 3,528,449 A | 9/1970 | Witte et al. |
| 3,813,316 A | 5/1974 | Chakrabarty et al. |
| 3,985,649 A | 10/1976 | Eddelman |
| 4,018,089 A | 4/1977 | Dzula et al. |
| 4,018,652 A | 4/1977 | Lanham et al. |
| 4,038,192 A | 7/1977 | Serur |
| 4,055,395 A | 10/1977 | Honkawa et al. |
| D249,706 S | 9/1978 | Adamski |
| 4,139,005 A | 2/1979 | Dickey |
| D252,157 S | 6/1979 | Kronish et al. |
| D252,341 S | 7/1979 | Thomas |
| D254,687 S | 4/1980 | Fadler et al. |
| 4,212,744 A | 7/1980 | Oota |
| D261,033 S | 9/1981 | Armbruster |
| D261,173 S | 10/1981 | Armbruster |
| 4,301,412 A | 11/1981 | Hill et al. |
| 4,439,526 A | 3/1984 | Columbus |
| 4,457,329 A | 7/1984 | Werley et al. |
| 4,466,740 A | 8/1984 | Kano et al. |
| 4,504,582 A | 3/1985 | Swann |
| 4,522,786 A | 6/1985 | Ebersole |
| D279,817 S | 7/1985 | Chen et al. |
| D282,208 S | 1/1986 | Lowry |
| 4,599,315 A | 7/1986 | Teraski et al. |
| 4,612,873 A | 9/1986 | Eberle |
| 4,612,959 A | 9/1986 | Costello |
| D288,478 S | 2/1987 | Carlson et al. |
| 4,647,432 A | 3/1987 | Wakatake |
| 4,654,127 A | 3/1987 | Baker et al. |
| 4,673,657 A | 6/1987 | Christian |
| 4,678,752 A | 7/1987 | Thorne et al. |
| 4,683,195 A | 7/1987 | Mullis et al. |
| 4,683,202 A | 7/1987 | Mullis |
| D292,735 S | 11/1987 | Lovborg |
| 4,720,374 A | 1/1988 | Ramachandran |
| 4,724,207 A | 2/1988 | Hou et al. |
| 4,798,693 A | 1/1989 | Mase et al. |
| 4,800,022 A | 1/1989 | Leonard |
| 4,841,786 A | 6/1989 | Schulz |
| D302,294 S | 7/1989 | Hillman |
| 4,871,779 A | 10/1989 | Killat et al. |
| 4,895,650 A | 1/1990 | Wang |
| 4,919,829 A | 4/1990 | Gates et al. |
| 4,921,809 A | 5/1990 | Shiff et al. |
| 4,935,342 A | 6/1990 | Seligson et al. |
| 4,946,562 A | 8/1990 | Guruswamy |
| 4,949,742 A | 8/1990 | Rando et al. |
| D310,413 S | 9/1990 | Bigler er al. |
| 4,963,498 A | 10/1990 | Hillman |
| 4,967,950 A | 11/1990 | Legg et al. |
| D312,692 S | 12/1990 | Bradley |
| 4,978,502 A | 12/1990 | Dole et al. |
| 4,978,622 A | 12/1990 | Mishell et al. |
| 4,989,626 A | 2/1991 | Takagi et al. |
| 5,001,417 A | 3/1991 | Pumphrey et al. |
| 5,004,583 A | 4/1991 | Guruswamy et al. |
| 5,048,554 A | 9/1991 | Kremer |
| 5,053,199 A | 10/1991 | Keiser et al. |
| 5,060,823 A | 10/1991 | Perlman |
| 5,061,336 A | 10/1991 | Soane |
| 5,064,618 A | 11/1991 | Baker et al. |
| 5,071,531 A | 12/1991 | Soane |
| 5,091,328 A | 2/1992 | Miller |
| D324,426 S | 3/1992 | Fan et al. |
| 5,096,669 A | 3/1992 | Lauks et al. |
| D325,638 S | 4/1992 | Sloat et al. |
| 5,126,002 A | 6/1992 | Iwata et al. |
| 5,126,022 A | 6/1992 | Soane et al. |
| D328,135 S | 7/1992 | Fan et al. |
| D328,794 S | 8/1992 | Frenkel et al. |
| 5,135,627 A | 8/1992 | Soane |
| 5,135,872 A | 8/1992 | Pouletty et al. |
| 5,147,606 A | 9/1992 | Charlton et al. |
| 5,169,512 A | 12/1992 | Wiedenmann et al. |
| D333,522 S | 2/1993 | Gianino |
| 5,186,339 A | 2/1993 | Heissler |
| 5,192,507 A | 3/1993 | Taylor et al. |
| 5,208,163 A | 5/1993 | Charlton et al. |
| 5,217,694 A | 6/1993 | Gibler et al. |
| 5,223,226 A | 6/1993 | Whittmer et al. |
| D338,275 S | 8/1993 | Fischer et al. |
| 5,250,263 A | 10/1993 | Manz |
| 5,252,743 A | 10/1993 | Barrett et al. |
| 5,256,376 A | 10/1993 | Callan et al. |
| 5,275,787 A | 1/1994 | Yuguchi et al. |
| 5,282,950 A | 2/1994 | Dietze et al. |
| 5,296,375 A | 3/1994 | Kricka et al. |
| 5,304,477 A | 4/1994 | Nagoh et al. |
| 5,304,487 A | 4/1994 | Wilding et al. |
| D347,478 S | 5/1994 | Pinkney |
| 5,311,896 A | 5/1994 | Kaartinen et al. |
| 5,311,996 A | 5/1994 | Duffy et al. |
| 5,316,727 A | 5/1994 | Suzuki et al. |
| 5,327,038 A | 7/1994 | Culp |
| 5,339,486 A | 8/1994 | Persic |
| D351,475 S | 10/1994 | Gerber |
| D351,913 S | 10/1994 | Hieb et al. |
| 5,364,591 A | 11/1994 | Green et al. |
| 5,372,946 A | 12/1994 | Cusak et al. |
| 5,374,395 A | 12/1994 | Robinson |
| 5,389,339 A | 2/1995 | Petschek et al. |
| D356,232 S | 3/1995 | Armstrong et al. |
| 5,397,709 A | 3/1995 | Berndt |
| 5,401,465 A | 3/1995 | Smethers et al. |
| 5,411,708 A | 5/1995 | Moscetta et al. |
| 5,414,245 A | 5/1995 | Hackleman |
| 5,416,000 A | 5/1995 | Allen et al. |
| 5,422,271 A | 6/1995 | Chen et al. |
| 5,422,284 A | 6/1995 | Lau |
| 5,427,946 A | 6/1995 | Kricka et al. |

(56) References Cited

U.S. PATENT DOCUMENTS

| | | |
|---|---|---|
| 5,443,791 A | 8/1995 | Cathcart et al. |
| 5,474,796 A | 12/1995 | Brennan |
| D366,116 S | 1/1996 | Biskupski |
| 5,486,335 A | 1/1996 | Wilding et al. |
| 5,494,639 A | 2/1996 | Grzegorzewski |
| 5,498,392 A | 3/1996 | Wilding et al. |
| 5,503,803 A | 4/1996 | Brown |
| 5,516,410 A | 5/1996 | Schneider et al. |
| 5,519,635 A | 5/1996 | Miyake et al. |
| 5,529,677 A | 6/1996 | Schneider et al. |
| 5,559,432 A | 9/1996 | Logue |
| 5,565,171 A | 10/1996 | Dovichi et al. |
| 5,569,364 A | 10/1996 | Hooper et al. |
| 5,578,270 A | 11/1996 | Reichler et al. |
| 5,578,818 A | 11/1996 | Kain et al. |
| 5,579,928 A | 12/1996 | Anukwuem |
| 5,580,523 A | 12/1996 | Bard |
| 5,582,884 A | 12/1996 | Ball et al. |
| 5,585,069 A | 12/1996 | Zanucchi et al. |
| 5,585,089 A | 12/1996 | Queen et al. |
| 5,585,242 A | 12/1996 | Bouma et al. |
| 5,587,128 A | 12/1996 | Wilding et al. |
| 5,589,136 A | 12/1996 | Northrup et al. |
| 5,593,838 A | 1/1997 | Zanzucchi et al. |
| 5,595,708 A | 1/1997 | Berndt |
| 5,599,432 A | 2/1997 | Manz et al. |
| 5,599,503 A | 2/1997 | Manz et al. |
| 5,599,667 A | 2/1997 | Arnold, Jr. et al. |
| 5,601,727 A | 2/1997 | Bormann et al. |
| 5,603,351 A | 2/1997 | Cherukuri et al. |
| 5,605,662 A | 2/1997 | Heller et al. |
| D378,782 S | 4/1997 | LaBarbera et al. |
| 5,628,890 A | 5/1997 | Carter et al. |
| 5,630,920 A | 5/1997 | Friese et al. |
| 5,631,337 A | 5/1997 | Sassi et al. |
| 5,632,876 A | 5/1997 | Zanzucchi et al. |
| 5,632,957 A | 5/1997 | Heller et al. |
| 5,635,358 A | 6/1997 | Wilding et al. |
| 5,637,469 A | 6/1997 | Wilding et al. |
| 5,639,423 A | 6/1997 | Northrup et al. |
| 5,643,738 A | 7/1997 | Zanzucchi et al. |
| 5,646,039 A | 7/1997 | Northrup et al. |
| 5,646,049 A | 7/1997 | Tayi |
| 5,647,994 A | 7/1997 | Tuunanen et al. |
| 5,651,839 A | 7/1997 | Rauf |
| 5,652,141 A | 7/1997 | Henco et al. |
| 5,652,149 A | 7/1997 | Mileaf et al. |
| D382,346 S | 8/1997 | Buhler et al. |
| D382,647 S | 8/1997 | Staples et al. |
| 5,667,976 A | 9/1997 | Van Ness et al. |
| 5,671,303 A | 9/1997 | Shieh et al. |
| 5,674,394 A | 10/1997 | Whitmore |
| 5,674,742 A | 10/1997 | Northrup et al. |
| 5,681,484 A | 10/1997 | Zanzucchi et al. |
| 5,681,529 A | 10/1997 | Taguchi et al. |
| 5,683,657 A | 11/1997 | Mian |
| 5,699,157 A | 12/1997 | Parce |
| 5,700,637 A | 12/1997 | Southern |
| 5,705,813 A | 1/1998 | Apffel et al. |
| 5,721,136 A | 2/1998 | Finney et al. |
| 5,726,026 A | 3/1998 | Wilding et al. |
| 5,726,404 A | 3/1998 | Brody |
| 5,726,944 A | 3/1998 | Pelley et al. |
| 5,731,212 A | 3/1998 | Gavin et al. |
| 5,744,366 A | 4/1998 | Kricka et al. |
| 5,747,666 A | 5/1998 | Willis |
| 5,750,015 A | 5/1998 | Soane et al. |
| 5,755,942 A | 5/1998 | Zanzucchi et al. |
| 5,763,262 A | 6/1998 | Wong et al. |
| 5,770,029 A | 6/1998 | Nelson et al. |
| 5,770,388 A | 6/1998 | Vorpahl |
| 5,772,966 A | 6/1998 | Maracas et al. |
| 5,779,868 A | 7/1998 | Parce et al. |
| 5,787,032 A | 7/1998 | Heller et al. |
| 5,788,814 A | 8/1998 | Sun et al. |
| 5,800,600 A | 9/1998 | Lima-Marques et al. |
| 5,800,690 A | 9/1998 | Chow et al. |
| 5,804,436 A | 9/1998 | Okun et al. |
| D399,959 S | 10/1998 | Prokop et al. |
| 5,827,481 A | 10/1998 | Bente et al. |
| 5,842,106 A | 11/1998 | Thaler et al. |
| 5,842,787 A | 12/1998 | Kopf-Sill et al. |
| 5,846,396 A | 12/1998 | Zanzucchi et al. |
| 5,846,493 A | 12/1998 | Bankier et al. |
| 5,849,208 A | 12/1998 | Hayes et al. |
| 5,849,486 A | 12/1998 | Heller et al. |
| 5,849,489 A | 12/1998 | Heller |
| 5,849,598 A | 12/1998 | Wilson et al. |
| 5,852,495 A | 12/1998 | Parce |
| 5,856,174 A | 1/1999 | Lipshutz et al. |
| 5,858,187 A | 1/1999 | Ramsey et al. |
| 5,858,188 A | 1/1999 | Soane et al. |
| 5,863,502 A | 1/1999 | Southgate et al. |
| 5,863,708 A | 1/1999 | Zanzucchi et al. |
| 5,863,801 A | 1/1999 | Southgate et al. |
| 5,866,345 A | 2/1999 | Wilding et al. |
| 5,869,004 A | 2/1999 | Parce et al. |
| 5,869,244 A | 2/1999 | Martin et al. |
| 5,872,010 A | 2/1999 | Karger et al. |
| 5,872,623 A | 2/1999 | Stabile et al. |
| 5,874,046 A | 2/1999 | Megerle |
| 5,876,675 A | 3/1999 | Kennedy |
| 5,880,071 A | 3/1999 | Parce et al. |
| 5,882,465 A | 3/1999 | McReynolds |
| 5,883,211 A | 3/1999 | Sassi et al. |
| 5,885,432 A | 3/1999 | Hooper et al. |
| 5,885,470 A | 3/1999 | Parce et al. |
| 5,895,762 A | 4/1999 | Greenfield et al. |
| 5,900,130 A | 5/1999 | Benregnu et al. |
| 5,912,124 A | 6/1999 | Kumar |
| 5,912,134 A | 6/1999 | Shartle |
| 5,916,522 A | 6/1999 | Boyd et al. |
| 5,916,776 A | 6/1999 | Kumar |
| 5,919,646 A | 7/1999 | Okun et al. |
| 5,919,711 A | 7/1999 | Boyd et al. |
| 5,922,591 A | 7/1999 | Anderson et al. |
| 5,927,547 A | 7/1999 | Papen et al. |
| 5,928,880 A | 7/1999 | Wilding et al. |
| 5,929,208 A | 7/1999 | Heller et al. |
| D413,391 S | 8/1999 | Lapeus et al. |
| 5,932,799 A | 8/1999 | Moles |
| 5,935,401 A | 8/1999 | Amigo |
| 5,939,291 A | 8/1999 | Loewy et al. |
| 5,942,443 A | 8/1999 | Parce et al. |
| D413,677 S | 9/1999 | Dumitrescu et al. |
| 5,948,227 A | 9/1999 | Dubrow |
| 5,948,363 A | 9/1999 | Gaillard |
| 5,955,028 A | 9/1999 | Chow |
| 5,955,029 A | 9/1999 | Wilding et al. |
| 5,957,579 A | 9/1999 | Kopf-Sill et al. |
| 5,958,203 A | 9/1999 | Parce et al. |
| 5,958,694 A | 9/1999 | Nikiforov |
| 5,959,221 A | 9/1999 | Boyd et al. |
| 5,959,291 A | 9/1999 | Jensen |
| 5,964,995 A | 10/1999 | Nikiforov et al. |
| 5,964,997 A | 10/1999 | McBride |
| 5,965,001 A | 10/1999 | Chow et al. |
| 5,965,410 A | 10/1999 | Chow et al. |
| 5,965,886 A | 10/1999 | Sauer et al. |
| 5,968,745 A | 10/1999 | Thorp et al. |
| 5,972,187 A | 10/1999 | Parce et al. |
| 5,973,138 A | 10/1999 | Collis |
| D417,009 S | 11/1999 | Boyd |
| 5,976,336 A | 11/1999 | Dubrow et al. |
| 5,980,704 A | 11/1999 | Cherukuri et al. |
| 5,980,719 A | 11/1999 | Cherukuri et al. |
| 5,981,735 A | 11/1999 | Thatcher et al. |
| 5,989,402 A | 11/1999 | Chow et al. |
| 5,992,820 A | 11/1999 | Fare et al. |
| 5,993,611 A | 11/1999 | Moroney, III et al. |
| 5,993,750 A | 11/1999 | Ghosh et al. |
| 5,997,708 A | 12/1999 | Craig |
| 6,001,229 A | 12/1999 | Ramsey |
| 6,001,231 A | 12/1999 | Kopf-Sill |

(56) References Cited

U.S. PATENT DOCUMENTS

| | | |
|---|---|---|
| 6,001,307 A | 12/1999 | Naka et al. |
| 6,004,515 A | 12/1999 | Parce et al. |
| 6,007,690 A | 12/1999 | Nelson et al. |
| 6,010,607 A | 1/2000 | Ramsey |
| 6,010,608 A | 1/2000 | Ramsey |
| 6,010,627 A | 1/2000 | Hood |
| 6,012,902 A | 1/2000 | Parce |
| D420,747 S | 2/2000 | Dumitrescu et al. |
| D421,130 S | 2/2000 | Cohen et al. |
| 6,024,920 A | 2/2000 | Cunanan |
| D421,653 S | 3/2000 | Purcell |
| 6,033,546 A | 3/2000 | Ramsey |
| 6,043,080 A | 3/2000 | Lipshutz et al. |
| 6,046,056 A | 4/2000 | Parce et al. |
| 6,048,734 A | 4/2000 | Burns et al. |
| 6,054,034 A | 4/2000 | Soane et al. |
| 6,054,277 A | 4/2000 | Furcht et al. |
| 6,056,860 A | 5/2000 | Amigo et al. |
| 6,057,149 A | 5/2000 | Burns et al. |
| 6,062,261 A | 5/2000 | Jacobson et al. |
| 6,063,341 A | 5/2000 | Fassbind et al. |
| 6,063,589 A | 5/2000 | Kellogg et al. |
| 6,068,752 A | 5/2000 | Dubrow et al. |
| 6,071,478 A | 6/2000 | Chow |
| 6,074,725 A | 6/2000 | Kennedy |
| 6,074,827 A | 6/2000 | Nelson et al. |
| D428,497 S | 7/2000 | Lapeus et al. |
| 6,086,740 A | 7/2000 | Kennedy |
| 6,096,509 A | 8/2000 | Okun et al. |
| 6,100,541 A | 8/2000 | Nagle et al. |
| 6,102,897 A | 8/2000 | Lang |
| 6,103,537 A | 8/2000 | Ullman et al. |
| 6,106,685 A | 8/2000 | McBride et al. |
| 6,110,343 A | 8/2000 | Ramsey et al. |
| 6,123,205 A | 9/2000 | Dumitrescu et al. |
| 6,123,798 A | 9/2000 | Gandhi et al. |
| 6,130,098 A | 10/2000 | Handique et al. |
| 6,132,580 A | 10/2000 | Mathies et al. |
| 6,132,684 A | 10/2000 | Marino |
| 6,133,436 A | 10/2000 | Koster et al. |
| D433,759 S | 11/2000 | Mathis et al. |
| 6,143,250 A | 11/2000 | Tajima |
| 6,149,787 A | 11/2000 | Chow et al. |
| 6,156,199 A | 12/2000 | Zuk |
| 6,158,269 A | 12/2000 | Dorenkott et al. |
| 6,167,910 B1 | 1/2001 | Chow |
| 6,168,948 B1 | 1/2001 | Anderson et al. |
| 6,171,850 B1 | 1/2001 | Nagle et al. |
| 6,174,675 B1 | 1/2001 | Chow et al. |
| 6,180,950 B1 | 1/2001 | Olsen |
| D438,311 S | 2/2001 | Yamanishi et al. |
| 6,190,619 B1 | 2/2001 | Kilcoin et al. |
| D438,632 S | 3/2001 | Miller |
| D438,633 S | 3/2001 | Miller |
| D439,673 S | 3/2001 | Brophy et al. |
| 6,197,595 B1 | 3/2001 | Anderson et al. |
| 6,211,989 B1 | 4/2001 | Wulf et al. |
| 6,213,151 B1 | 4/2001 | Jacobson et al. |
| 6,221,600 B1 | 4/2001 | Macleod et al. |
| 6,228,635 B1 | 5/2001 | Armstrong et al. |
| 6,232,072 B1 | 5/2001 | Fisher |
| 6,235,175 B1 | 5/2001 | Dubrow et al. |
| 6,235,313 B1 | 5/2001 | Mathiowitz et al. |
| 6,235,471 B1 | 5/2001 | Knapp et al. |
| 6,236,456 B1 | 5/2001 | Giebeler et al. |
| 6,236,581 B1 | 5/2001 | Foss et al. |
| 6,238,626 B1 | 5/2001 | Higuchi et al. |
| 6,251,343 B1 | 6/2001 | Dubrow et al. |
| 6,254,826 B1 | 7/2001 | Acosta et al. |
| 6,259,635 B1 | 7/2001 | Khouri et al. |
| 6,261,431 B1 | 7/2001 | Mathies et al. |
| 6,267,858 B1 | 7/2001 | Parce et al. |
| D446,306 S | 8/2001 | Ochi et al. |
| 6,271,021 B1 | 8/2001 | Burns et al. |
| 6,274,089 B1 | 8/2001 | Chow et al. |
| 6,280,967 B1 | 8/2001 | Ransom et al. |
| 6,281,008 B1 | 8/2001 | Komai et al. |
| 6,284,113 B1 | 9/2001 | Bjornson et al. |
| 6,284,470 B1 | 9/2001 | Bitner et al. |
| 6,287,254 B1 | 9/2001 | Dodds |
| 6,287,774 B1 | 9/2001 | Kikiforov |
| 6,291,248 B1 | 9/2001 | Haj-Ahmad |
| 6,294,063 B1 | 9/2001 | Becker et al. |
| 6,302,134 B1 | 10/2001 | Kellogg et al. |
| 6,302,304 B1 | 10/2001 | Spencer |
| 6,303,343 B1 | 10/2001 | Kopf-sill |
| 6,306,273 B1 | 10/2001 | Wainright et al. |
| 6,306,590 B1 | 10/2001 | Mehta et al. |
| 6,316,774 B1 | 11/2001 | Giebeler et al. |
| 6,319,469 B1 | 11/2001 | Mian et al. |
| 6,322,683 B1 | 11/2001 | Wolk et al. |
| 6,326,083 B1 | 12/2001 | Yang et al. |
| 6,326,147 B1 | 12/2001 | Oldham et al. |
| 6,326,211 B1 | 12/2001 | Anderson et al. |
| 6,334,980 B1 | 1/2002 | Hayes et al. |
| 6,337,435 B1 | 1/2002 | Chu et al. |
| 6,353,475 B1 | 3/2002 | Jensen et al. |
| 6,358,387 B1 | 3/2002 | Kopf-sill et al. |
| 6,366,924 B1 | 4/2002 | Parce |
| 6,368,561 B1 | 4/2002 | Rutishauser et al. |
| 6,368,871 B1 | 4/2002 | Christel et al. |
| 6,370,206 B1 | 4/2002 | Schenk |
| 6,375,185 B1 | 4/2002 | Lin |
| 6,375,901 B1 | 4/2002 | Robotti et al. |
| 6,379,884 B2 | 4/2002 | Wada et al. |
| 6,379,929 B1 | 4/2002 | Burns et al. |
| 6,379,974 B1 | 4/2002 | Parce et al. |
| 6,382,254 B1 | 5/2002 | Yang et al. |
| 6,391,541 B1 | 5/2002 | Petersen et al. |
| 6,391,623 B1 | 5/2002 | Besemer et al. |
| 6,395,161 B1 | 5/2002 | Schneider et al. |
| 6,398,956 B1 | 6/2002 | Coville et al. |
| 6,399,025 B1 | 6/2002 | Chow |
| 6,399,389 B1 | 6/2002 | Parce et al. |
| 6,399,952 B1 | 6/2002 | Maher et al. |
| 6,401,552 B1 | 6/2002 | Elkins |
| 6,403,338 B1 | 6/2002 | Knapp et al. |
| 6,408,878 B2 | 6/2002 | Unger et al. |
| 6,413,401 B1 | 7/2002 | Chow et al. |
| 6,416,642 B1 | 7/2002 | Alajoki et al. |
| 6,420,143 B1 | 7/2002 | Kopf-sill |
| 6,425,972 B1 | 7/2002 | McReynolds |
| D461,906 S | 8/2002 | Pham |
| 6,428,987 B2 | 8/2002 | Franzen |
| 6,430,512 B1 | 8/2002 | Gallagher |
| 6,432,366 B2 | 8/2002 | Ruediger et al. |
| 6,440,725 B1 | 8/2002 | Pourahmadi et al. |
| D463,031 S | 9/2002 | Slomski et al. |
| 6,444,461 B1 | 9/2002 | Knapp et al. |
| 6,447,661 B1 | 9/2002 | Chow et al. |
| 6,447,727 B1 | 9/2002 | Parce et al. |
| 6,448,064 B1 | 9/2002 | Vo-Dinh et al. |
| 6,453,928 B1 | 9/2002 | Kaplan et al. |
| 6,465,257 B1 | 10/2002 | Parce et al. |
| 6,468,761 B2 | 10/2002 | Yang et al. |
| 6,472,141 B2 | 10/2002 | Nikiforov |
| 6,475,364 B1 | 11/2002 | Dubrow et al. |
| D467,348 S | 12/2002 | McMichael et al. |
| D467,349 S | 12/2002 | Niedbala et al. |
| 6,488,897 B2 | 12/2002 | Dubrow et al. |
| 6,495,104 B1 | 12/2002 | Unno et al. |
| 6,498,497 B1 | 12/2002 | Chow et al. |
| 6,500,323 B1 | 12/2002 | Chow et al. |
| 6,500,390 B1 | 12/2002 | Boulton et al. |
| D468,437 S | 1/2003 | McMenamy et al. |
| 6,506,609 B1 | 1/2003 | Wada et al. |
| 6,509,193 B1 | 1/2003 | Tajima |
| 6,511,853 B1 | 1/2003 | Kopf-sill et al. |
| 6,515,753 B2 | 2/2003 | Maher |
| 6,517,783 B2 | 2/2003 | Horner et al. |
| 6,520,197 B2 | 2/2003 | Deshmukh et al. |
| 6,521,188 B1 | 2/2003 | Webster |
| 6,524,456 B1 | 2/2003 | Ramsey et al. |
| 6,524,790 B1 | 2/2003 | Kopf-sill et al. |

(56) References Cited

U.S. PATENT DOCUMENTS

| | | |
|---|---|---|
| 6,534,295 B2 | 3/2003 | Tai et al. |
| 6,537,771 B1 | 3/2003 | Farinas et al. |
| 6,540,896 B1 | 4/2003 | Manz et al. |
| 6,544,734 B1 | 4/2003 | Briscoe et al. |
| 6,547,942 B1 | 4/2003 | Parce et al. |
| 6,555,389 B1 | 4/2003 | Ullman et al. |
| 6,556,923 B2 | 4/2003 | Gallagher et al. |
| 6,558,916 B2 | 5/2003 | Veerapandian et al. |
| 6,558,945 B1 | 5/2003 | Kao |
| 6,569,607 B2 | 5/2003 | McReynolds |
| 6,572,830 B1 | 6/2003 | Burdon et al. |
| 6,575,188 B2 | 6/2003 | Parunak |
| 6,576,459 B2 | 6/2003 | Miles et al. |
| 6,579,453 B1 | 6/2003 | Bächler et al. |
| 6,589,729 B2 | 7/2003 | Chan et al. |
| 6,592,821 B1 | 7/2003 | Wada et al. |
| 6,597,450 B1 | 7/2003 | Andrews et al. |
| 6,602,474 B1 | 8/2003 | Tajima |
| 6,613,211 B1 | 9/2003 | Mccormick et al. |
| 6,613,512 B1 | 9/2003 | Kopf-sill et al. |
| 6,613,580 B1 | 9/2003 | Chow et al. |
| 6,613,581 B1 | 9/2003 | Wada et al. |
| 6,620,625 B2 | 9/2003 | Wolk et al. |
| 6,623,860 B2 | 9/2003 | Hu et al. |
| 6,627,406 B1 | 9/2003 | Singh et al. |
| 6,632,655 B1 | 10/2003 | Mehta et al. |
| 6,633,785 B1 | 10/2003 | Kasahara et al. |
| 6,640,981 B2 | 11/2003 | Lafond et al. |
| 6,649,358 B1 | 11/2003 | Parce et al. |
| 6,664,104 B2 | 12/2003 | Pourahmadi et al. |
| 6,669,831 B2 | 12/2003 | Chow et al. |
| 6,670,153 B2 | 12/2003 | Stern |
| 6,681,616 B2 | 1/2004 | Spaid et al. |
| 6,685,813 B2 | 2/2004 | Williams et al. |
| 6,692,700 B2 | 2/2004 | Handique |
| 6,695,009 B2 | 2/2004 | Chien et al. |
| 6,706,519 B1 | 3/2004 | Kellogg et al. |
| 6,730,206 B2 | 5/2004 | Ricco et al. |
| 6,733,645 B1 | 5/2004 | Chow |
| 6,734,401 B2 | 5/2004 | Bedingham et al. |
| 6,737,026 B1 | 5/2004 | Bergh et al. |
| 6,740,518 B1 | 5/2004 | Duong et al. |
| 6,750,661 B2 | 6/2004 | Brooks et al. |
| 6,752,966 B1 | 6/2004 | Chazan |
| 6,756,019 B1 | 6/2004 | Dubrow et al. |
| 6,764,859 B1 | 7/2004 | Kreuwel et al. |
| 6,766,817 B2 | 7/2004 | Dias da Silva |
| 6,773,567 B1 | 8/2004 | Wolk |
| 6,777,184 B2 | 8/2004 | Nikiforov et al. |
| 6,783,962 B1 | 8/2004 | Olander et al. |
| 6,787,015 B2 | 9/2004 | Lackritz et al. |
| 6,787,016 B2 | 9/2004 | Tan et al. |
| 6,787,111 B2 | 9/2004 | Roach et al. |
| 6,790,328 B2 | 9/2004 | Jacobson et al. |
| 6,790,330 B2 | 9/2004 | Gascoyne et al. |
| 6,811,668 B1 | 11/2004 | Berndt et al. |
| 6,818,113 B2 | 11/2004 | Williams et al. |
| 6,819,027 B2 | 11/2004 | Saraf |
| 6,824,663 B1 | 11/2004 | Boone |
| D500,363 S | 12/2004 | Fanning et al. |
| 6,827,831 B1 | 12/2004 | Chow et al. |
| 6,827,906 B1 | 12/2004 | Bjornson et al. |
| 6,838,156 B1 | 1/2005 | Neyer et al. |
| 6,852,287 B2 | 2/2005 | Ganesan |
| 6,858,185 B1 | 2/2005 | Kopf-sill et al. |
| 6,859,698 B2 | 2/2005 | Schmeisser |
| 6,861,035 B2 | 3/2005 | Pham et al. |
| 6,878,540 B2 | 4/2005 | Pourahmadi et al. |
| 6,878,755 B2 | 4/2005 | Singh et al. |
| 6,884,628 B2 | 4/2005 | Hubbell et al. |
| 6,887,693 B2 | 5/2005 | McMillan et al. |
| 6,893,879 B2 | 5/2005 | Petersen et al. |
| 6,905,612 B2 | 6/2005 | Dorian et al. |
| 6,906,797 B1 | 6/2005 | Kao et al. |
| 6,908,594 B1 | 6/2005 | Schaevitz et al. |
| 6,911,183 B1 | 6/2005 | Handique et al. |
| 6,914,137 B2 | 7/2005 | Baker |
| 6,915,679 B2 | 7/2005 | Chien et al. |
| 6,918,404 B2 | 7/2005 | Dias da Silva |
| 6,939,451 B2 | 9/2005 | Zhao et al. |
| 6,942,771 B1 | 9/2005 | Kayyem |
| 6,958,392 B2 | 10/2005 | Fomovskaia et al. |
| 6,964,747 B2 | 11/2005 | Banerjee et al. |
| 6,984,516 B2 | 1/2006 | Briscoe et al. |
| 7,004,184 B2 | 2/2006 | Handique et al. |
| 7,010,391 B2 | 3/2006 | Handique et al. |
| 7,037,416 B2 | 5/2006 | Parce et al. |
| 7,049,558 B2 | 5/2006 | Baer et al. |
| 7,066,586 B2 | 6/2006 | Dias da Silva |
| 7,118,910 B2 | 10/2006 | Unger et al. |
| 7,148,043 B2 | 12/2006 | Kordunsky et al. |
| 7,169,277 B2 | 1/2007 | Ausserer et al. |
| 7,169,618 B2 | 1/2007 | Skould |
| 7,192,557 B2 | 3/2007 | Wu et al. |
| 7,235,406 B1 | 6/2007 | Woudenberg et al. |
| 7,270,786 B2 | 9/2007 | Parunak et al. |
| 7,276,208 B2 | 10/2007 | Sevigny et al. |
| 7,288,228 B2 | 10/2007 | Lefebvre |
| 7,323,140 B2 | 1/2008 | Handique et al. |
| 7,332,130 B2 | 2/2008 | Handique |
| 7,338,760 B2 | 3/2008 | Gong et al. |
| 7,351,377 B2 | 4/2008 | Chazan et al. |
| 7,374,949 B2 | 5/2008 | Kuriger |
| 7,390,460 B2 | 6/2008 | Osawa et al. |
| 7,476,313 B2 | 1/2009 | Siddiqi |
| 7,494,770 B2 | 2/2009 | Wilding et al. |
| 7,527,769 B2 | 5/2009 | Bunch et al. |
| 7,553,671 B2 | 6/2009 | Sinclair et al. |
| 7,674,431 B2 | 3/2010 | Ganesan |
| D637,737 S | 5/2011 | Wilson et al. |
| 8,088,616 B2 | 1/2012 | Handique |
| 8,105,783 B2 | 1/2012 | Handique |
| 8,110,158 B2 | 2/2012 | Handique |
| 8,133,671 B2 | 3/2012 | Williams et al. |
| D669,597 S | 10/2012 | Cavada et al. |
| 8,287,820 B2 | 10/2012 | Williams et al. |
| 8,323,584 B2 | 12/2012 | Ganesan |
| 8,323,900 B2 | 12/2012 | Handique et al. |
| 8,324,372 B2 | 12/2012 | Brahmasandra et al. |
| 8,415,103 B2 | 4/2013 | Handique |
| 8,420,015 B2 | 4/2013 | Ganesan et al. |
| 8,440,149 B2 | 5/2013 | Handique |
| 8,470,586 B2 | 6/2013 | Wu et al. |
| 8,473,104 B2 | 6/2013 | Handique et al. |
| D692,162 S | 10/2013 | Lentz et al. |
| 8,679,831 B2 | 3/2014 | Handique et al. |
| 8,685,341 B2 | 4/2014 | Ganesan |
| 8,703,069 B2 | 4/2014 | Handique et al. |
| 8,709,787 B2 | 4/2014 | Handique |
| 8,710,211 B2 | 4/2014 | Brahmasandra et al. |
| 8,734,733 B2 | 5/2014 | Handique |
| 8,765,076 B2 | 7/2014 | Handique et al. |
| 8,852,862 B2 | 10/2014 | Wu et al. |
| 8,883,490 B2 | 11/2014 | Handique et al. |
| 8,894,947 B2 | 11/2014 | Ganesan et al. |
| 8,895,311 B1 | 11/2014 | Handique et al. |
| 9,028,773 B2 | 5/2015 | Ganesan |
| 9,040,288 B2 | 5/2015 | Handique et al. |
| 9,080,207 B2 | 7/2015 | Handique et al. |
| 2001/0012492 A1 | 8/2001 | Acosta et al. |
| 2001/0021355 A1 | 9/2001 | Baugh et al. |
| 2001/0023848 A1 | 9/2001 | Gjerde et al. |
| 2001/0038450 A1 | 11/2001 | McCaffrey et al. |
| 2001/0046702 A1 | 11/2001 | Schmebri |
| 2001/0048899 A1 | 12/2001 | Marouiss et al. |
| 2001/0055765 A1 | 12/2001 | O'Keefe et al. |
| 2002/0001848 A1 | 1/2002 | Bedingham et al. |
| 2002/0008053 A1 | 1/2002 | Hansen et al. |
| 2002/0009015 A1 | 1/2002 | Laugharn, Jr. et al. |
| 2002/0014443 A1 | 2/2002 | Hansen et al. |
| 2002/0015667 A1 | 2/2002 | Chow |
| 2002/0021983 A1 | 2/2002 | Comte et al. |
| 2002/0037499 A1 | 3/2002 | Quake et al. |
| 2002/0039783 A1 | 4/2002 | McMillan et al. |

(56) References Cited

U.S. PATENT DOCUMENTS

| | | |
|---|---|---|
| 2002/0053399 A1 | 5/2002 | Soane et al. |
| 2002/0054835 A1 | 5/2002 | Robotti et al. |
| 2002/0055167 A1 | 5/2002 | Pourahmadi et al. |
| 2002/0058332 A1 | 5/2002 | Quake et al. |
| 2002/0060156 A1 | 5/2002 | Mathies et al. |
| 2002/0068357 A1 | 6/2002 | Mathies et al. |
| 2002/0141903 A1 | 10/2002 | Parunak et al. |
| 2002/0142471 A1 | 10/2002 | Handique et al. |
| 2002/0143297 A1 | 10/2002 | Francavilla et al. |
| 2002/0143437 A1 | 10/2002 | Handique et al. |
| 2002/0155477 A1 | 10/2002 | Ito |
| 2002/0169518 A1 | 11/2002 | Luoma et al. |
| 2002/0187557 A1 | 12/2002 | Hobbs et al. |
| 2002/0192808 A1 | 12/2002 | Gambini et al. |
| 2003/0019522 A1 | 1/2003 | Parunak |
| 2003/0022392 A1 | 1/2003 | Hudak |
| 2003/0049174 A1 | 3/2003 | Ganesan |
| 2003/0049833 A1 | 3/2003 | Chen et al. |
| 2003/0064507 A1 | 4/2003 | Gallagher et al. |
| 2003/0070677 A1 | 4/2003 | Handique et al. |
| 2003/0072683 A1 | 4/2003 | Stewart et al. |
| 2003/0073106 A1 | 4/2003 | Johansen et al. |
| 2003/0083686 A1 | 5/2003 | Freeman et al. |
| 2003/0087300 A1 | 5/2003 | Knapp et al. |
| 2003/0096310 A1 | 5/2003 | Hansen et al. |
| 2003/0127327 A1 | 7/2003 | Kurnik |
| 2003/0136679 A1 | 7/2003 | Bohn et al. |
| 2003/0186295 A1 | 10/2003 | Colin et al. |
| 2003/0190608 A1 | 10/2003 | Blackburn et al. |
| 2003/0199081 A1 | 10/2003 | Wilding et al. |
| 2003/0211517 A1 | 11/2003 | Carulli et al. |
| 2004/0014202 A1 | 1/2004 | King et al. |
| 2004/0014238 A1 | 1/2004 | Krug et al. |
| 2004/0018119 A1 | 1/2004 | Massaro |
| 2004/0022689 A1 | 2/2004 | Wulf et al. |
| 2004/0029258 A1 | 2/2004 | Heaney et al. |
| 2004/0029260 A1 | 2/2004 | Hansen et al. |
| 2004/0037739 A1 | 2/2004 | McNeely et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0072375 A1 | 4/2004 | Gjerde et al. |
| 2004/0086427 A1 | 5/2004 | Childers et al. |
| 2004/0086956 A1 | 5/2004 | Bachur |
| 2004/0141887 A1 | 7/2004 | Mainquist et al. |
| 2004/0151629 A1 | 8/2004 | Pease et al. |
| 2004/0157220 A1 | 8/2004 | Kurnool et al. |
| 2004/0161788 A1 | 8/2004 | Chen et al. |
| 2004/0189311 A1 | 9/2004 | Glezer et al. |
| 2004/0200909 A1 | 10/2004 | McMillan et al. |
| 2004/0209331 A1 | 10/2004 | Ririe |
| 2004/0209354 A1 | 10/2004 | Mathies et al. |
| 2004/0219070 A1 | 11/2004 | Handique |
| 2004/0224317 A1 | 11/2004 | Kordunsky et al. |
| 2004/0235154 A1 | 11/2004 | Oh et al. |
| 2004/0240097 A1 | 12/2004 | Evans |
| 2005/0009174 A1 | 1/2005 | Nikiforov et al. |
| 2005/0013737 A1 | 1/2005 | Chow et al. |
| 2005/0037471 A1 | 2/2005 | Liu et al. |
| 2005/0041525 A1 | 2/2005 | Pugia et al. |
| 2005/0042639 A1 | 2/2005 | Knapp et al. |
| 2005/0048540 A1 | 3/2005 | Inami et al. |
| 2005/0058574 A1 | 3/2005 | Bysouth et al. |
| 2005/0058577 A1 | 3/2005 | Micklash et al. |
| 2005/0069898 A1 | 3/2005 | Moon et al. |
| 2005/0084424 A1 | 4/2005 | Ganesan et al. |
| 2005/0106066 A1 | 5/2005 | Saltsman et al. |
| 2005/0121324 A1 | 6/2005 | Park et al. |
| 2005/0129580 A1 | 6/2005 | Swinehart et al. |
| 2005/0133370 A1 | 6/2005 | Park et al. |
| 2005/0135655 A1 | 6/2005 | Kopf-sill et al. |
| 2005/0142036 A1 | 6/2005 | Kim et al. |
| 2005/0152808 A1 | 7/2005 | Ganesan |
| 2005/0186585 A1 | 8/2005 | Juncosa et al. |
| 2005/0202504 A1 | 9/2005 | Anderson et al. |
| 2005/0208676 A1 | 9/2005 | Kahatt |
| 2005/0214172 A1 | 9/2005 | Burgisser |
| 2005/0220675 A1 | 10/2005 | Reed et al. |
| 2005/0227269 A1 | 10/2005 | Lloyd et al. |
| 2005/0233370 A1 | 10/2005 | Ammann et al. |
| 2005/0272079 A1 | 12/2005 | Burns et al. |
| 2006/0041058 A1 | 2/2006 | Yin et al. |
| 2006/0057039 A1 | 3/2006 | Morse et al. |
| 2006/0057629 A1 | 3/2006 | Kim |
| 2006/0094108 A1 | 5/2006 | Yoder et al. |
| 2006/0133965 A1 | 6/2006 | Tajima et al. |
| 2006/0134790 A1 | 6/2006 | Tanaka et al. |
| 2006/0148063 A1 | 7/2006 | Fauzzi et al. |
| 2006/0165558 A1 | 7/2006 | Witty et al. |
| 2006/0166233 A1 | 7/2006 | Wu et al. |
| 2006/0177376 A1 | 8/2006 | Tomalia et al. |
| 2006/0177855 A1 | 8/2006 | Utermohlen et al. |
| 2006/0183216 A1 | 8/2006 | Handique |
| 2006/0201887 A1 | 9/2006 | Siddiqi |
| 2006/0207944 A1 | 9/2006 | Siddiqi |
| 2006/0210435 A1 | 9/2006 | Alavie et al. |
| 2006/0269961 A1 | 11/2006 | Fukushima et al. |
| 2007/0104617 A1 | 5/2007 | Coulling et al. |
| 2007/0116613 A1 | 5/2007 | Elsener |
| 2007/0196237 A1 | 8/2007 | Neuzil et al. |
| 2007/0215554 A1 | 9/2007 | Kreuwel et al. |
| 2007/0231213 A1 | 10/2007 | Prabhu et al. |
| 2007/0243626 A1 | 10/2007 | Windeyer et al. |
| 2007/0292941 A1 | 12/2007 | Handique et al. |
| 2008/0003649 A1 | 1/2008 | Maltezos et al. |
| 2008/0017306 A1 | 1/2008 | Liu et al. |
| 2008/0050804 A1 | 2/2008 | Handique et al. |
| 2008/0056948 A1 | 3/2008 | Dale et al. |
| 2008/0069729 A1 | 3/2008 | McNeely |
| 2008/0075634 A1 | 3/2008 | Herchenbach et al. |
| 2008/0095673 A1 | 4/2008 | Xu |
| 2008/0226502 A1 | 9/2008 | Jonsmann et al. |
| 2009/0047180 A1 | 2/2009 | Kawahara |
| 2009/0129978 A1 | 5/2009 | Wilson et al. |
| 2009/0130745 A1 | 5/2009 | Williams et al. |
| 2009/0131650 A1 | 5/2009 | Brahmasandra et al. |
| 2009/0134069 A1 | 5/2009 | Handique |
| 2009/0136385 A1 | 5/2009 | Handique et al. |
| 2009/0189089 A1 | 7/2009 | Bedingham et al. |
| 2009/0221059 A1 | 9/2009 | Williams et al. |
| 2011/0008825 A1 | 1/2011 | Ingber et al. |
| 2011/0158865 A1 | 6/2011 | Miller et al. |
| 2012/0022695 A1 | 1/2012 | Handique et al. |
| 2012/0122108 A1 | 5/2012 | Handique |
| 2012/0160826 A1 | 6/2012 | Handique |
| 2012/0171759 A1 | 7/2012 | Williams et al. |
| 2012/0183454 A1 | 7/2012 | Handique |
| 2012/0258463 A1 | 10/2012 | Duffy et al. |
| 2013/0037564 A1 | 2/2013 | Williams et al. |
| 2013/0071851 A1 | 3/2013 | Handique et al. |
| 2013/0096292 A1 | 4/2013 | Brahmasandra et al. |
| 2013/0101990 A1 | 4/2013 | Handique et al. |
| 2013/0164832 A1 | 6/2013 | Ganesan et al. |
| 2013/0183769 A1 | 7/2013 | Tajima |
| 2013/0217013 A1 | 8/2013 | Steel et al. |
| 2013/0217102 A1 | 8/2013 | Ganesan et al. |
| 2013/0251602 A1 | 9/2013 | Handique et al. |
| 2013/0280131 A1 | 10/2013 | Handique et al. |
| 2013/0288358 A1 | 10/2013 | Handique et al. |
| 2014/0030798 A1 | 1/2014 | Wu et al. |
| 2014/0045186 A1 | 2/2014 | Gubatayao et al. |
| 2014/0206088 A1 | 7/2014 | Lentz et al. |
| 2014/0212882 A1 | 7/2014 | Handique et al. |
| 2014/0227710 A1 | 8/2014 | Handique et al. |
| 2014/0297047 A1 | 10/2014 | Ganesan et al. |
| 2014/0323357 A1 | 10/2014 | Handique et al. |
| 2014/0323711 A1 | 10/2014 | Brahmasandra et al. |
| 2014/0329301 A1 | 11/2014 | Handique et al. |
| 2014/0342352 A1 | 11/2014 | Handique et al. |
| 2015/0064702 A1 | 3/2015 | Handique et al. |
| 2015/0118684 A1 | 4/2015 | Wu et al. |
| 2015/0133345 A1 | 5/2015 | Handique et al. |

(56) References Cited

U.S. PATENT DOCUMENTS

| | | | |
|---|---|---|---|
| 2015/0142186 A1 | 5/2015 | Handique et al. | |
| 2015/0152477 A1 | 6/2015 | Ganesan | |

FOREIGN PATENT DOCUMENTS

| | | |
|---|---|---|
| DE | 19929734 | 12/1999 |
| DE | 19833293 C1 | 1/2000 |
| EP | 0365828 A2 | 5/1990 |
| EP | 0483620 A2 | 5/1992 |
| EP | 0688602 A2 | 12/1995 |
| EP | 0766256 | 4/1997 |
| EP | 1077086 A2 | 2/2001 |
| EP | 1346772 A2 | 9/2003 |
| EP | 1541237 A2 | 6/2005 |
| EP | 1574586 A2 | 9/2005 |
| EP | 1792656 A1 | 6/2007 |
| EP | 2372367 A1 | 10/2011 |
| FR | 2672301 | 8/1992 |
| FR | 2795426 | 12/2000 |
| GB | 2453432 A | 4/2009 |
| JP | S50-100881 | 8/1975 |
| JP | 58212921 A | 12/1983 |
| JP | S62-119460 | 5/1987 |
| JP | H01-502319 | 8/1989 |
| JP | 03-054470 | 3/1991 |
| JP | 04-053555 U | 5/1992 |
| JP | 06-064156 U | 9/1994 |
| JP | 07-020010 | 1/1995 |
| JP | H07-290706 | 11/1995 |
| JP | H08-122336 | 5/1996 |
| JP | H08-211071 | 8/1996 |
| JP | H08-285859 | 11/1996 |
| JP | H09-325151 | 12/1997 |
| JP | 2001-502790 | 1/1998 |
| JP | 2000-514928 | 4/1999 |
| JP | H11-515106 | 12/1999 |
| JP | 2000-180455 | 6/2000 |
| JP | 2000-275255 | 10/2000 |
| JP | 2001-502319 | 2/2001 |
| JP | 2001-509437 | 7/2001 |
| JP | 3191150 B2 | 7/2001 |
| JP | 2001-515216 | 9/2001 |
| JP | 2001-527220 | 12/2001 |
| JP | 2002-503331 | 1/2002 |
| JP | 2002-085961 | 3/2002 |
| JP | 2002-517735 | 6/2002 |
| JP | 2002-215241 | 7/2002 |
| JP | 2002-544476 | 12/2002 |
| JP | 2003-500674 | 1/2003 |
| JP | 2003-047839 A | 2/2003 |
| JP | 2003-047840 A | 2/2003 |
| JP | 2003-516125 | 5/2003 |
| JP | 2003-185584 | 7/2003 |
| JP | 2003-299485 | 10/2003 |
| JP | 2003-329693 | 11/2003 |
| JP | 2004-506179 A | 2/2004 |
| JP | 2004-150797 A | 5/2004 |
| JP | 2004-531360 A | 10/2004 |
| JP | 2004-533838 | 11/2004 |
| JP | 2004-361421 | 12/2004 |
| JP | 2004-536291 | 12/2004 |
| JP | 2005-009870 | 1/2005 |
| JP | 2005-511264 | 4/2005 |
| JP | 2005-514718 | 5/2005 |
| JP | 2005-518825 | 6/2005 |
| JP | 2005-176613 A | 7/2005 |
| JP | 2005-192554 | 7/2005 |
| JP | 2005-204661 | 8/2005 |
| JP | 2005-525816 | 9/2005 |
| JP | 2005-291954 A | 10/2005 |
| JP | 2005-532043 | 10/2005 |
| JP | 2005-323519 | 11/2005 |
| JP | 2006-021156 A | 1/2006 |
| JP | 2006-094866 A | 4/2006 |
| JP | 2006-167569 | 6/2006 |
| JP | 2007-074960 | 3/2007 |
| JP | 2007-97477 | 4/2007 |
| JP | 2007-510518 | 4/2007 |
| JP | 2007-514405 A | 6/2007 |
| JP | 2007-178328 | 7/2007 |
| WO | WO 88/06633 | 9/1988 |
| WO | WO 90/12350 | 10/1990 |
| WO | WO 92/05443 | 4/1992 |
| WO | WO 94/11103 | 5/1994 |
| WO | WO 96/04547 | 2/1996 |
| WO | WO 97/05492 | 2/1997 |
| WO | WO 97/21090 | 6/1997 |
| WO | WO 98/00231 | 1/1998 |
| WO | WO 98/22625 | 5/1998 |
| WO | WO 98/35013 A1 | 8/1998 |
| WO | WO 98/49548 | 11/1998 |
| WO | WO 98/53311 | 11/1998 |
| WO | WO 99/01688 | 1/1999 |
| WO | WO 99/09042 | 2/1999 |
| WO | WO 99/12016 | 3/1999 |
| WO | WO 99/33559 | 7/1999 |
| WO | WO 01/05510 | 1/2001 |
| WO | WO 01/14931 | 3/2001 |
| WO | WO 01/27614 | 4/2001 |
| WO | WO 01/28684 | 4/2001 |
| WO | WO 01/41931 | 6/2001 |
| WO | WO 01/54813 | 8/2001 |
| WO | WO 01/89681 | 11/2001 |
| WO | WO 02/072264 | 9/2002 |
| WO | WO 02/078845 | 10/2002 |
| WO | WO 03/007677 | 1/2003 |
| WO | WO 03/012325 | 2/2003 |
| WO | WO 03/012406 | 2/2003 |
| WO | WO 03/048295 | 6/2003 |
| WO | WO 03/055605 | 7/2003 |
| WO | WO 03/076661 | 9/2003 |
| WO | WO 03/087410 | 10/2003 |
| WO | WO 2004/007081 | 1/2004 |
| WO | WO 2004/048545 | 6/2004 |
| WO | WO 2004/055522 | 7/2004 |
| WO | WO 2004/056485 A1 | 7/2004 |
| WO | WO 2004/074848 | 9/2004 |
| WO | WO 2004/094986 | 11/2004 |
| WO | WO 2005/011867 | 2/2005 |
| WO | WO 2005/030984 | 4/2005 |
| WO | WO 2005/107947 | 11/2005 |
| WO | WO 2005/108620 | 11/2005 |
| WO | WO 2005/116202 | 12/2005 |
| WO | WO 2005/118867 | 12/2005 |
| WO | WO 2005/120710 | 12/2005 |
| WO | WO 2006/010584 | 2/2006 |
| WO | WO 2006/032044 | 3/2006 |
| WO | WO 2006/035800 | 4/2006 |
| WO | WO 2006/066001 | 6/2006 |
| WO | WO 2006/079082 | 7/2006 |
| WO | WO 2006/113198 | 10/2006 |
| WO | WO 2006/119280 | 11/2006 |
| WO | WO 2007/044917 | 4/2007 |
| WO | WO 2007/050327 | 5/2007 |
| WO | WO 2007/064117 | 6/2007 |
| WO | WO 2007/091530 | 8/2007 |
| WO | WO 2007/112114 | 10/2007 |
| WO | WO 2008/030914 | 3/2008 |
| WO | WO 2008/060604 | 5/2008 |
| WO | WO 2009/054870 A2 | 4/2009 |
| WO | WO 2010/118541 | 10/2010 |
| WO | WO 2011/101467 | 8/2011 |

OTHER PUBLICATIONS

Tanaka et al., "Modification of DNA extraction from maize using polyamidoamine-dendrimer modified magnetic particles", Proceedings of the 74th Annual Meeting of the Electrochemical Society of Japan, Mar. 29, 2007; Faculty of Engineering, Science University of Tokyo; 2 pages.

Wu et al., "Polycationic dendrimers interact with RNA molecules: polyamine dendrimers inhibit the catalytic activity of Candida ribozymes", Chem Commun. (2005) 3: 313-315.

(56) References Cited

OTHER PUBLICATIONS

Zhou et al., "Cooperative binding and self-assembling behavior of cationic low molecular-weight dendrons with RNA molecules", Org Biomol Chem. (2006) 4(3): 581-585.

Zhou et al., "PANAM dendrimers for efficient siRNA delivery and potent gene silencing", Chem Comm.(Camb.) (2006) 22: 2362-2364.

Bollet, C. et al., "A simple method for the isolation of chromosomal DNA from Gram positive or acid-fast bacteria", Nucleic Acids Research, vol. 19, No. 8 (1991), p. 1955.

Brahmasandra et al., On-chip DNA detection in microfabricated separation systems, SPIE Conference on Microfluidic Devices and Systems, 1998, vol. 3515, pp. 242-251, Santa Clara, CA.

Breadmore, M.C. et al., "Microchip-Based Purification of DNA from Biological Samples", Anal. Chem., vol. 75 (2003), pp. 1880-1886.

Brody, et al., Diffusion-Based Extraction in a Microfabricated Device, Sensors and Actuators Elsevier, 1997, vol. A58, No. 1, pp. 13-18.

Broyles et al., "Sample Filtration, Concentration, and Separation Integrated on Microfluidic Devices" Analytical Chemistry (American Chemical Society), (2003) 75(11): 2761-2767.

Burns et al., "An Integrated Nanoliter DNA Analysis Device", Science 282:484-487 (1998).

Carlen et al., "Paraffin Actuated Surface Micromachined Valve," in IEEE MEMS 2000 Conference, Miyazaki, Japan, (Jan. 2000) pp. 381-385.

Chung, Y. et al., "Microfluidic chip for high efficiency DNA extraction", Miniaturisation for Chemistry, Biology & Bioengineering, vol. 4, No. 2 (Apr. 2004), pp. 141-147.

Handique et al, "Microfluidic flow control using selective hydrophobic patterning", SPIE, (1997) 3224: 185-194.

Handique et al., On-Chip Thermopneumatic Pressure for Discrete Drop Pumping, Analytical Chemistry, American Chemical Society, Apr. 15, 2001, vol. 73, No. 8, 1831-1838.

Handique, K. et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.

Handique, K. et al., "Mathematical Modeling of Drop Mixing in a Slit-Type Microchannel", J. Micromech. Microeng., 11:548-554 (2001).

Handique, K. et al., "Nanoliter Liquid Metering in Microchannels Using Hydrophobic Patterns", Anal. Chem., 72(17):4100-4109 (2000).

He, et al., Microfabricated Filters for Microfluidic Analytical Systems, Analytical Chemistry, American Chemical Society, 1999, vol. 71, No. 7, pp. 1464-1468.

Ibrahim, et al., Real-Time Microchip PCR for Detecting Single-Base Differences in Viral and Human DNA, Analytical Chemistry, American Chemical Society, 1998, 70(9): 2013-2017.

Khandurina et al., Microfabricated Porous Membrane Structure for Sample Concentration and Electrophoretic Analysis, Analytical Chemistry American Chemical Society, 1999, 71(9): 1815-1819.

Kopp et al., Chemical Amplification: Continuous-Flow PCR on a Chip, www.sciencemag.org, 1998, vol. 280, pp. 1046-1048.

Kutter et al., Solid Phase Extraction on Microfluidic Devices, J. Microcolumn Separations, John Wiley & Sons, Inc., 2000, 12(2): 93-97.

Lagally et al., Single-Molecule DNA Amplification and Analysis in an Integrated Microfluidic Device, Analytical Chemistry, American Chemical Society, 2001, 73(3): 565-570.

Livache et al., "Polypyrrole DNA chip on a Silicon Device: Example of Hepatitis C Virus Genotyping", Analytical Biochemistry, (1998) 255: 188-194.

Mascini et al., "DNA electrochemical biosensors", Fresenius J. Anal. Chem., 369: 15-22, (2001).

Nakagawa et al., Fabrication of amino silane-coated microchip for DNA extraction from whole blood, J of Biotechnology, Mar. 2, 2005, vol. 116, pp. 105-111.

Northrup et al., A Miniature Analytical Instrument for Nucleic Acids Based on Micromachined Silicon Reaction Chambers, Analytical Chemistry, American Chemical Society, 1998, 70(5): 918-922.

Oleschuk et al., Trapping of Bead-Based Reagents within Microfluidic Systems,: On-Chip Solid-Phase Extraction and Electrochromatography, Analytical Chemistry, American Chemical Society, 2000, 72(3): 585-590.

Plambeck et al., "Electrochemical Studies of Antitumor Antibiotics", J. Electrochem Soc.: Electrochemical Science and Technology (1984), 131(11): 2556-2563.

Roche, et al. "Ectodermal commitment of insulin-producing cells derived from mouse embryonic stem cells" Faseb J (2005) 19: 1341-1343.

Ross et al., Analysis of DNA Fragments from Conventional and Microfabricated PCR Devices Using Delayed Extraction MALDI-TOF Mass Spectrometry, Analytical Chemistry, American Chemical Society, 1998, 70(10): 2067-2073.

Shoffner et al., Chip PCR.I. Surface Passivation of Microfabricated Silicon-Glass Chips for PCR, Nucleic Acids Research, Oxford University Press, (1996) 24(2): 375-379.

Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.

Wang, "Survey and Summary, from DNA Biosensors to Gene Chips", Nucleic Acids Research, 28(16):3011-3016, (2000).

Waters et al., Microchip Device for Cell Lysis, Multiplex PCR Amplification, and Electrophoretic Sizing, Analytical Chemistry, American Chemical Society, 1998, 70(1): 158-162.

Weigl, et al., Microfluidic Diffusion-Based Separation and Detection, www.sciencemag.org, 1999, vol. 283, pp. 346-347.

Yoza et al., "Fully Automated DNA Extraction from Blood Using Magnetic Particles Modified with a Hyperbranched Polyamidoamine Dendrimer", Journal of Bioscience and Bioengineering, 2003, 95(1): 21-26.

Yoza et al., DNA extraction using bacterial magnetic particles modified with hyperbranched polyamidoamine dendrimer, Mar. 20, 2003, 101(3): 219-228.

Goldmeyer et al., "Identification of *Staphylococcus aureus* and Determination of Methicillin Resistance Directly from Positive Blood Cultures by Isothermal Amplification and a Disposable Detection Device", J Clin Microbiol. (Apr. 2008) 46(4): 1534-1536.

Meyers, R.A., Molecular Biology and Biotechnology: A Comprehensive Desk Reference; VCH Publishers, Inc. New York, NY; (1995) pp. 418-419.

METHODS AND SYSTEMS FOR CONTROL OF MICROFLUIDIC DEVICES

CROSS-REFERENCE TO RELATED APPLICATIONS

This application is a continuation of U.S. patent application Ser. No. 13/925,046, filed Jun. 24, 2013 and scheduled to issue on Jul. 1, 2014 as U.S. Pat. No. 8,768,517, which is a continuation of U.S. patent application Ser. No. 13/189,453, filed Jul. 22, 2011, issued as U.S. Pat. No. 8,473,104 on Jun. 25, 2013, which is a continuation of U.S. patent application Ser. No. 11/251,188, filed Oct. 13, 2005, issued as U.S. Pat. No. 7,987,022 on Jul. 26, 2011, which is a continuation of U.S. patent application Ser. No. 09/819,105, filed Mar. 28, 2001, issued as U.S. Pat. No. 7,010,391 on Mar. 7, 2006. The disclosures of all of the above-referenced prior applications, publications, and patents are considered part of the disclosure of this application, and are incorporated by reference herein in their entirety.

BACKGROUND OF THE INVENTION

1. Field of the Invention

The present invention relates to the field of microfluidics. More particularly, the present invention is directed to control methods, control systems, and control software for microfluidic devices that operate by moving discrete micro-droplets through a sequence of determined configurations.

2. Description of the Related Art

Micro/nano technology devices are known in the art as devices with components on the scale of 1 μm to 100s of μm that cooperate to perform various desired functions. In particular, microfluidic devices are micro/nano technology devices that perform fluid handling functions, which, for example, cooperate to carry out a chemical or biochemical reaction or analysis.

Most microfluidic devices in the prior art are based on fluid flowing through microscale passages and chambers, either continuously or in relatively large aliquots. Fluid flow is usually initiated and controlled by electro-osmotic and electrophoretic forces. See, e.g., U.S. Pat. No. 5,632,876, issued Apr. 27, 1997 and titled "Apparatus and Methods for Controlling Fluid Flow in Microchannels;" U.S. Pat. No. 5,992,820, issued Nov. 30, 1999 and titled "Flow Control in Microfluidics Devices by Controlled Bubble Formation;" U.S. Pat. No. 5,637,469, issued Jun. 10, 1997 and titled "Methods and Apparatus for the Detection of an Analyte Utilizing Mesoscale Flow Systems;" U.S. Pat. No. 5,800,690, issued Sep. 1, 1998 and titled "Variable Control of Electroosmotic and/or Electrophoretic Forces Within a Fluid-Containing Structure Via Electrical Forces;" and U.S. Pat. No. 6,001,231, issued Dec. 14, 1999 and titled "Methods and Systems for Monitoring and Controlling Fluid Flow Rates in Microfluidic Systems."

These devices are relatively disadvantageous because, inter alia, they require larger volumes of reactants by virtue of their flow-based design, and fluid control by electro-osmotic and electrophoretic forces typically requires relatively large voltages, which may be dangerous and are difficult to generate in small portable control devices. Control devices for microfluidic devices based on such technologies are larger, at least desktop in size.

More advantageous technologies for microfluidic devices have been developed by one or more of the inventors or the present application and others. This advantageous technology manipulates very small aliquots of fluids (known herein as "micro-droplets") in microscale passages by relying largely on pressure and other non-electric forces. These devices are advantageous in that smaller volumes of reagents are required, and in that non-electric forces can be generated by smaller voltages, of the order of magnitude output by standard microelectronic components. See, i.e., U.S. Pat. No. 6,057,149, issued May 2, 2000 and titled "Microscale Devices And Reactions In Microscale Devices;" U.S. Pat. No. 6,048,734, issued Apr. 11, 2000 and titled "Thermal Microvalves in a Fluid Flow Method;" and U.S. Pat. No. 6,130,098, issued Oct. 10, 2000.

However, to the knowledge of the inventors, no well-structured control systems have been provided for such micro-droplet-based microfluidic devices that exploits the essential advantages of such devices.

Citation or identification of any reference in this Section or any section of this application shall not be construed that such reference is available as prior art to the present invention.

SUMMARY OF THE INVENTION

It is one of the objects of the present invention to overcome this deficiency in the art and provide methods and systems for controlling micro-droplet-based microfluidic devices that exploits their essential advantages. Because of the structure and properties of such microfluidic devices, the methods and systems of this invention can be implemented in a wide range of embodiments, from entirely handheld embodiments to laboratory embodiments for performing high-throughput reactions and analyses. Further, because of the structure and properties of such microfluidic device, these methods and systems can be controlled by users to perform diverse reactions and analysis in a manner similar to programming a computer.

Thus, the present invention has for one of its several objects the provision of programmable control systems and software for what are known herein as "digital" microfluidic devices. The control systems provided, reflecting the design of preferred microfluidic devices themselves, have a generally hierarchical design in which detailed and lower-level device control is organized into a smaller number of basic control functions, while overall and higher-level device control is organized as sequences of the basic function that cause a particular device to carry out intended reactions of analyses. The control systems of the present invention are thereby adaptable to many different types of digital microfluidic devices and intended reactions; they are scalable to devices of various complexities, simple to program and economical.

An embodiment includes a system for controlling the operation of a microfluidic device having a micropassage for holding a micro-volume of liquid with a volume between one nano-liter and one micro-liter, a reaction chamber, and one or more active components. The system includes a processor that can receive a user request for the microfluidic device to perform a reaction program, memory including stored instructions corresponding to hierarchical control signals that can direct the microfluidic device to perform the user-requested reaction program, and a programmable digital acquisition unit including: a heater driver circuit, a temperature sensor driver circuit, and a detection driver circuit that passes signals to at least one active component that can detect reaction products in the reaction chamber. In some aspects, the digital acquisition unit generates control signals for the active components responsive to the user-requested reaction program that control (i) heating the micro-volume of liquid, (ii)

detecting a temperature related to the micro-volume of liquid, and (iii) detecting reaction products in the micro-volume of liquid.

An embodiment includes a system for controlling a microfluidic device having a micro-channel that can contain a micro-volume of liquid with a volume between one nano-liter and one micro-liter, a reaction chamber, and an actuator including associated and active components that can operate in coordination to achieve a desired functionality. The system includes memory having stored instructions corresponding to a user-selected reaction program. The memory includes a user level function corresponding to the reaction program, a microdroplet level function corresponding to an operation performed on a micro-volume of liquid contained within a microfluidic device, an actuator level function corresponding to an actuator operation, and a component level instruction directing the generation of a control signal for an individual component of the microfluidic device. The system includes an interface that can allow an operator to select a desired reaction program for the microfluidic device that corresponds to a user level function having a microdroplet level function, which microdroplet level function includes an actuator level function, and the actuator level function includes a component level function. The system further includes control circuitry that can create and transmit the control signal responsive to a component level function for controlling the component of the microfluidic device.

The present includes the embodiments recited above, as well as all combinations of the embodiments with their particular aspects and with the particular aspects of other embodiments. The invention further includes sub-combinations of these embodiments and aspects. This invention is also understood to include systems for practicing any of the described methods, these systems having the preferred hierarchical structures described in the following. This invention also includes combinations and sub-combinations of these systems, for example, a data acquisition board alone, or in combination with user interface hardware, or in combination with software, or in combination with microfluidic processor descriptive data, or so forth. This invention also includes computer readable media or computer memories storing programs for carrying out the methods of this invention along with necessary descriptive and state data.

BRIEF DESCRIPTION OF THE DRAWINGS

The present invention may be understood more fully by reference to the following detailed description of the preferred embodiment of the present invention, illustrative examples of specific embodiments of the invention, and the appended figures wherein.

In figures of the same numeric but differing alphabetic designation, for example, FIG. 5A and FIG. 5B, identical elements are referenced with the same reference characters.

Like reference symbols in the various drawings indicate like elements.

DETAILED DESCRIPTION OF THE PREFERRED EMBODIMENT

Preferred Microfluidic Devices

Figure 1:
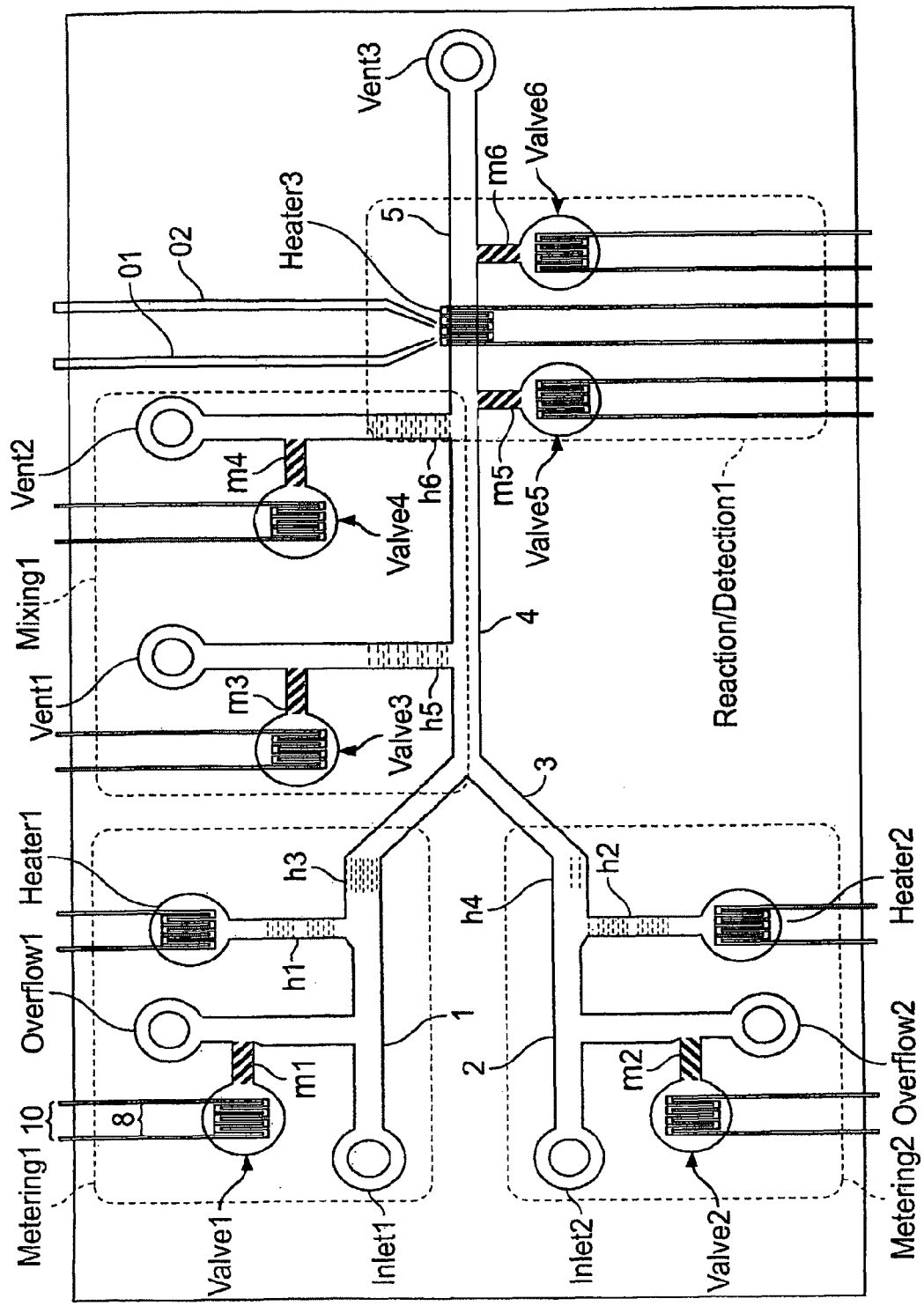
FIG. 1 illustrates an exemplary microfluidic device thermal controlled in a preferred manner.

This section generally describes preferred microfluidic devices controlled by the systems and methods of the present invention. The systems and methods of the present invention control microfluidic devices that operate in a manner referred to herein as "digital." In this sub-section, the general characteristics of "digital" microfluidic devices are first described. Subsequently, a more preferred type of thermally-controlled "digital" microfluidic device is described.

Digital Micro-Fluidic Devices

Microfluidic devices perform chemical or biochemical reactions or analyses by manipulating fluid reagents in chambers and passages which are generally sized in cross-section from approximately 10 to 50 $\mu M$ (micro-meter) up to approximately 100 to 1000 $\mu m$, and which are formed on or in a usually flat substrate having linear dimensions from approximately 1 mm (centimeter) to approximately 20 cm. A microfluidic device may manipulate fluid reactants as they flow through the passages and chambers of the device, either as continuous flows from input reservoirs through the device to outlet ports, or as semi-continuous flows of fluid aliquots substantially filling the passages and chambers of the device during operation. Alternatively, preferred microfluidic devices may manipulate fluid reagents as separate and discrete micro-droplets that are characterized by having lengths that are approximately an order of magnitude or more smaller than the dimensions of the device, for example, approximately 1 to 20 mm (millimeter) or less. Thus, during operation the passages and chambers of a preferred microfluidic device are largely free of fluid reagents. Micro-droplets may have, for example, volumes from approximately 1 nl (nano-liter) to approximately 1 $\mu l$ (microliter). For example a micro-droplet of size 10 $\mu m$ by 100 $\mu m$ by 1 mm has a volume of 1 nl; a 100 $\mu m$ by 1000 $\mu m$ by 10 mm micro-droplet has a volume of 1 $\mu l$. Each microfluidic device preferably manipulates micro-droplets of only a few pre-selected sizes or volumes.

"Digital" microfluidic devices, as this term is used and understood herein, are of the latter preferred type, maintaining and manipulating fluid reactants as separate and distinguishable micro-droplets. The passages and chambers of a digital microfluidic device have a plurality of predefined positions so that each micro-droplet either resides at one of the predefined positions or is moving between these predefined positions. The predefined positions, known herein as "stable" positions, are positions to which a micro-droplet can be moved and stably reside, and are created by configuration and arrangement of passages and chambers, and by the forces generated therein. A micro-droplet may reside motionless at a stable position even while other micro-droplets are moving between other stable positions. Stable positions may occur in regions where, for example, a force driving a micro-droplet may be made to vanish so that a micro-droplet becomes stationary, or where an extra force is required for transit so that in the absence of such extra force a micro-droplet will remain stationary, or where forces acting on the micro-droplet balance leaving no net driving force. In contrast, the less preferred type of microfluidic device that manipulates continuous or semi-continuous fluid flows through passages may be considered as an "analog" device.

Reactions in a digital microfluidic device may be specified in terms of micro-droplet residence at, and transitions between, stable positions. For example, during motion between stable positions, micro-droplets may be prepared for an intended reaction or analysis by metering a new micro-droplet from a fluid reservoir, or by mixing two or more existing micro-droplets into a single new micro-droplet, or so forth. ("Metering" a micro-droplet is taken herein to mean creating a new micro-droplet of approximately known volume or size.) A reaction may occur in a micro-droplet having the necessary composition while it resides at a stable position. Optionally, reaction in the stationary micro-droplet can be excited by, for example, heating, cooling, or radiation, or so forth, or may simply occur with the passage of time.

According to the present invention it is useful, but is not intended to be limiting, to consider digital microfluidic devices as analogous to finite-state machines (FSMs). FSMs are well known in the computer arts to have a finite number of states or configurations and to accomplish their functions through a series of state transitions from initial states to final states, each state transition being made in response to a determined input. Analogously, a state or configuration of a digital microfluidic device may be defined by a description of the micro-droplets present in the device and the stable position at which each micro-droplet currently resides. The number of these configurations is finite because a digital microfluidic device manipulates a finite number of discrete and distinguishable micro-droplets which reside at a finite number of stable positions. Operation of a digital microfluidic device to carry out an intended reaction or analysis may then be defined by a sequence of configurations from an initial configuration to a final configuration. In the initial configuration, the device has pre-loaded reagents in their initial positions and is ready for the loading of any remaining reagents or samples. Intermediate configurations result from micro-droplet manipulations that form a micro-droplet with the constituent reagents necessary for the intended reaction in a stable reaction position. In the final configuration, the intended reaction takes place in this formed micro-droplet.

Accordingly, control methods and systems of the present invention in preferred embodiments are structured so that reaction control may be specified in terms of manipulations of micro-droplets, or equivalently transitions of microfluidic device configurations. In this structure, details of actual device control, which are device technology and implementation dependent, appear only in relation to performing micro-droplet manipulations, and can otherwise be substantially ignored for reaction control. In an important aspect, the present invention structures the details of device control for micro-droplet manipulation by incorporating advantageous features, techniques, and principles known in the computer arts for the control of FSMs. For example, the stable positions in a digital microfluidic device may be considered as one or more "registers," the passages between stable states may be considered as "combinatorial logic" between the registers.

The configuration of a device may be considered as the occupancy of the "registers" by micro-droplets, and methods and systems for controlled digital microfluidic devices may be designed according to register-transfer design paradigms known for similar types of FSMs. As a further example, a digital microfluidic device may be controlled in an overlapped or pipelined manner, wherein the various micro-droplets arrive at their locations in a particular configuration at different times, so that the configuration is not realized at single time throughout the microfluidic device. Such overlap, or pipelining, of configurations may be advantageous because pipelined control, which breaks a single operation into a sequence of sub-operations, is known in the computer arts to be a method of achieving increased processor throughput.

In the more preferred embodiments to be described next, the details of device control make important use of the principles of hierarchical structure. It is to be understood, however, that this analogy is not intended to lead to limiting inferences. For example, the control methods and systems of this invention are not limited to known FSM control methods and techniques.

Preferred Digital Microfluidic Devices (Processors)

The systems and methods of the present invention may be applied to control general digital microfluidic devices as just described. They are preferably applied, however, to digital microfluidic devices that have the following additional properties (i) predominantly modular and hierarchical structures, and (ii) of controllability mainly by electrical control signals.

Such preferred digital microfluidic devices, hereinafter called microfluidic "processors" (or simply "processors"), are preferred over general digital microfluidic devices because a wide range of different processors may be flexibly and easily controlled by a single programmable control system implementing modular and hierarchically structured control methods. Control of a particular microfluidic process of a particular class is then specified by invoking a high-level control module, which hierarchically encapsulates details of low-level control for all microfluidic processors of that particular class.

These two preferred properties of microfluidic processors are next described in detail. The first property, that a microfluidic processor has a largely modular and hierarchical construction means herein, first, that a microfluidic processor is constructed from a limited number of types of basic functional modules, for example, preferably less than approximately 10 module types, or more preferably less than approximately 5 module types. In terms of the FSM analogy, these basic functional types of modules are analogous to the basic functional types of electrical circuits, for example, NAND, NOR gates, and flip-flops, out of which FSMs may be constructed. In the following, basic modules are primarily termed "actuators." A exemplary set of basic actuator types, sufficient for many (but not necessarily all) microfluidic processors, includes micro-valve type actuators, pressure generation type actuators (or other types of force generating actuators), heating/cooling type actuators, actuators for monitoring processor state, and so forth. Micro-valves can be controlled to close or open a particular passage, preferably reversibly, to the motion of micro-droplets, gases, or other passage contents. Pressure generation actuators can be controlled to create relative gas pressure (or relative vacuum). Heating/cooling actuators can be controlled to perform localized or generalized heating or cooling. Actuators for state monitoring can be controlled to provide input that signals micro-droplet position, local processor temperature, or other parameters. Actuators for optical excitation and detection may also be desirable. For example, radiation may initiate a reaction or monitor reaction products; radiation may also be used to monitor micro-droplet position and composition.

Modular and hierarchical construction is also taken to mean that actuators are in turn hierarchically constructed from atomically-controllable, discretely-implemented, device-level components. Atomic or discretely-implemented controllable components are those device-level controllable components that, in the technology used for a particular microfluidic processor, may be directly implemented, or are the simplest controllable components, or may not be decomposed into simpler controllable components, or so forth. Any particular microfluidic-processor technology typically does not have single, unitary, components at the device implementation level for the all actuator types. For example, in the preferred thermally-controllable class of processors to be described, there is no single atomically-controllable micro-valve component having a micro-valve function available for constructing microfluidic processors. Instead micro-valve actuator function is built from several individual components, each of which is atomically controllable and discretely implemented and which are arranged together and jointly controlled by the methods of this invention to have a micro-valve function. This is, of course, similar to electrically-controllable "macro-valves," which are also built from a number of unitary mechanical and electrical components which function together to perform the valve function. It is also analogous to FSMs where, for example, NOR gates cannot be directly implemented in many semiconductor fabrication technologies, but rather must be constructed from an arrangement of gates (made in turn from transistors) formed from regions of semiconductor, conductor, and insulator which can be directly implemented. Accordingly, in any implementation technology, each basic actuator type is usually constructed from several lower-level and discretely-implemented components which are arranged and controlled to have the particular actuator function. In other words, actuators are usually hierarchical constructs of individual device components available in a particular implementation technology.

Such substantially hierarchical construction does not rule out certain actuator types which may be constructed from only a single device component. In some technologies, certain actuator functions may, without limitation, be directly implemented. Nor does it rule out a certain amount of "special purpose" microfluidic functions which may be needed to implement certain limited and specialized functions not describable of the basic and generalized actuator functions. Preferably, special purpose function occupies less than 20%, and more preferably less than 10%, of the area or device count of a processor.

Substantially modular construction also preferably extends to higher design levels. At higher design levels, microfluidic processors are built from sub-assemblies of a limited number of sub-assembly types. Each type of sub-assembly is controlled to perform certain type of micro-droplet manipulations; in other words, it is sub-assemblies that are controlled to cause the transitions between device configurations necessary for the intended reaction or analysis. In keeping with the principle of hierarchical construction, each sub-assembly type is, in turn, built from a number of individual actuators combined and interconnected with passages, chambers, ports, and so forth. Generally, the methods of this invention have a hierarchical structured in parallel with the microfluidic processor technology so that actuators are controlled primarily to realize sub-assembly function, and device-level components are controlled primarily to realize actuator function.

Sub-assembly types are preferably limited to less than approximately 10 sub-assemblies, or more preferably to less than approximately 5 sub-assemblies. An exemplary set of sub-assembly types provides for metering micro-droplets of determined volumes, for moving micro-droplets, combining two or more micro-droplets, mixing a possibly heterogeneous micro-droplet, stimulating (or exciting) a reaction in a micro-droplet, observing and detecting reaction products, and so forth. For example, a metering sub-assembly may use a source of gas pressure to pinch off a fluid-filled passage of determined volume from a larger fluid reservoir. A sub-assembly for moving a micro-droplet may use a pressure generator actuator to generate mechanical force, gas pressure, to push the micro-droplet. A sub-assembly for combining two micro-droplets may include two inlet passages converging to a single outlet passage, the inlet passages being controlled with micro-valve actuators and being provided with micro-droplet motion actuators. A micro-droplet mixing sub-assembly may be built from a micro-droplet motion actuator that causes sufficiently rapid motion to induce laminar mixing. A reaction/analysis sub-assembly may be built from a chamber (or a length of passage) with access controlled by micro-valve actuators, and provided with actuators to stimulate the reaction, for example, through the application of heat or radiation. A stub-assembly for detecting results of reactions or analyses may, for example, employ actuators to sense micro-droplet optical properties. Further examples of actuators and sub-assemblies will be apparent to one of skill in the art in view of the following description of a specific exemplary digital microfluidic processor.

Largely modular and hierarchical construction is not intended to cause needless limitations or duplications in microfluidic processor design. For example, although each actuator is usually part of a single sub-assembly, it may be advantageous and economical for a single actuator to function as part of two or more sub-assemblies. Similarly, one device-level component may function as part of two or more actuators. How components or actuators may be employed as parts of higher-level functional structures is often technology specific.

The second preferred property of preferred microfluidic processors is that they are controlled primarily by electrical signals, and to a lesser extent by optical signals, with other types of signals, such as pneumatic, hydraulic, mechanical or so forth, being employed rarely if at all. Control signals are generated by control systems of the present invention operating according to the methods of the present invention, and are exchanged with a microfluidic processor being controlled in order to control the directly-controllable, device-level components, and thereby to realize higher-order actuator and sub-assembly functions. Monitoring signals may be transmitted from a controlled microfluidic processor to a control system to reflect the effect of prior control signals, such as, for example, whether a specified temperature has been reached, whether a micro-valve opened or closed as controlled, whether a micro-droplet moved as controlled, and so on. In other words, direct device control, and thus actuator control and sub-assembly control, is done on or in the microfluidic processor principally in response to electrical signals with little or no intervention by external devices. Use of external devices is preferably limited to unavoidable loading of samples or reactants not initially present in the processor, or to otherwise interfacing with the external environment.

Preferred electrical control signals are of relatively low voltage (preferably less than 50 V (volt), more preferably less than 25 V, and even more preferably less than 15 V or 10 V. Control signals sent to a microfluidic processor from a controller may include, for example, electrical inputs causing internal actuator operation, or optical inputs that excite or probe reaction products. The electrical inputs may be dedicated to individual microfluidic processors or, according to an embodiment of the invention, the electrical inputs may be shared in an array so as to reduce the number of external contacts. Control signals received from a microfluidic processor may include primarily electrical outputs for monitoring device state, for example, temperature-monitoring signals, or micro-droplet-position monitoring signals. Optical signal outputs may monitor micro-droplet presence, micro-droplet optical characteristics to determine the results of a reaction or analysis, or so forth. Whether optical signals are generated and detected on a microfluidic processor in response to external electrical control signals, or whether optical signals are externally generated and detected in a controller (also in response to electrical signals) and exchanged optically, for example, over fiber-optic paths with a processor, is an implementation matter.

Microfluidic processors may be constructed according to any technology that allows microfluidic processors to be controlled micro-droplet-configuration-by-micro-droplet-configuration using external electrical signals. For example, microfluidic processors can be constructed according to the arts of mechanical and silicon-based nano-technologies. Passages may be etched in glass or silicon; valves may include flexible silicon elements actuated by applied voltages; fluids may be moved by moveable nano-elements, or by controlled pressure, either available from an external source or generated internally. A single microfluidic device can be constructed in a single technology, or may include multiple technologies.

Preferred Micro-Fluidic Processors

Preferred microfluidic processors primarily use thermally-controlled actuators with optical signals for monitoring or detection. In particular they are constructed according to a technology that uses local resistive heating or Peltier-device cooling for control functions. For example, a thermally-controlled processor can be maintained at baseline temperature by a temperature-controlled heat sink or a cooling element, such as a Peltier device, with actuators controlled by localized heating above the baseline. Localized heating may preferably be provided by low power resistive heaters of less than approximately 1 to 2 W, advantageously controlled by low voltages, for example, less than 50, 25, 15 or 10 V.

Mechanical force, where needed for control purposes, may be provided by gas pressure generated by localized heating applied to a gas reservoir within a processor. For example, controlled gas pressure may be directly used to cause micro-droplet motion. Controlled gas pressure may also be used to control micro-valves by causing an obstructing element to move into and close a passage, while return to normal pressure may draw the obstructing element back and open the passage. In a preferred embodiment, the obstructing element may be a low melting point solid, which is melted for valve operation also by localized heating. Thermally-controlled micro-valves may act to admit externally provided relative pressure or relative vacuum into a processor for powering more complex actuators. Thermally-controlled mechanical force may also be generated by other means, such as by other heat-sensitive fluids, by differentially expandable materials, and so forth. Additionally, localized heating and cooling may be directly applied to micro-droplets for reaction control. Further, electrical signals may be used for actuator control in other manners, such as attractive or repulsive magnetic or electric forces.

In this embodiment, device monitoring signals are derived primarily from temperature sensitive elements mounted in the device, which preferably generate electrical monitoring signals such as, for example, temperature-sensitive resistive or semiconductor elements. Localized heating may be precisely controlled by sensed temperatures. Gas pressures may then be controlled by controlled localized heating. Local thermal capacity may be monitored by a combination of a temperature sensor with a small heater by measuring temperature responses with respect to a determined quantity of heat. Using local thermal capacity sensors, micro-droplet presence or absence may be sensed because a micro-droplet has a higher thermal capacity than an otherwise empty passage. Other electrical monitoring signals may be generated by, for example, detecting local electrical impedance, which may provide alternative means for detecting micro-droplet presence. Micro-sensors with deformable conductive elements may provide for direct detection of local pressures.

Optical signals may be used in preferred microfluidic processors where advantageous. For example, scattered radiation may provide the simplest means of detecting or observing reaction or analysis results. Incident radiation may be helpful to initiate or stimulate a reaction or analysis. Also, micro-droplet position sensors may be optically based.

In more detail, FIG. 1 illustrates, schematically and not to scale, an exemplary integrated microfluidic processor constructed in the preferred modular and hierarchical manner in an embodiment of the preferred thermal-control technology. This integrated microfluidic processor is designed to perform a sample analysis through the following steps: meter predetermined micro-droplets from two sources, for example, a source of the sample and a source of analysis reagents; mix the metered micro-droplets to form a third homogeneous micro-droplet; perform a temperature-controlled analysis reaction in the third micro-droplet; and finally, optically monitor the analysis results.

This exemplary microfluidic processor is constructed from three types of sub-assemblies, each sub-assembly being constructed from three types of actuators, and each actuator being constructed from one type of controllable device-level component. The processor also contains passive components such as passages, reservoirs, ports, outlets, optic conductors, and so forth. In particular, this processor has four separate sub-assemblies: two micro-droplet metering sub-assemblies, metering1 and metering2; one mixing sub-assembly, mixing 1; and one reaction/detection sub-assembly; referenced reaction/detection1. These sub-assemblies are constructed from three controllable heater actuators, six controllable valve actuators, and one optical detector, all interconnected with passive inlets, overflows, vents, and reservoirs. The sub-assemblies have the following components: sub-assembly metering1 includes inlet1, overflow1, valve1, heater1, and passage 1; sub-assembly metering2 includes inlet2, overflow2, valve2, heater2, and passage 2; sub-assembly mixing1 includes heater1 (and optionally heater2), valve3, valve4, vent1, vent2, Y-shaped passage 3 and passage 4; and sub-assembly reaction/detection1 includes valve5, valve6, heater3, and passage 5. Here, heater1 and heater2 are included in both the mixing and in the metering sub-assemblies. Also, heater1, valve3, valve4, vent1, vent2, and passages 1 and 4 alone may form a micro-droplet motion sub-assembly. Lastly, in addition to passive passages, the processor is constructed from only one type of controllable device-level components, localized resistive heaters. Preferably, resistive heaters are operatively coupled to resistive temperature detectors that provide feedback information.

Before a description of sub-assembly operation, exemplary passage configurations for creating and defining stable positions are described. Generally, stable positions are created by hydrophobic regions, or by the relative arrangement of main passages and vented side passages. (Main passages are continuing passages along which micro-droplets are manipulated; side passage are dead-end passages branching from the main passages.) First, hydrophobic regions, for example regions h1-h6 of FIG. 1, are limited regions whose interiors have been treated to assume a hydrophobic character, whereas the remainder of the passage interiors have a hydrophilic, or at least a wettable character (either normally or by treatment). Because of surface tension effects in micro-droplets, predominantly aqueous micro-droplets will travel in the hydrophilic regions of passages with smaller hindrance than when they travel in the hydrophobic regions. In effect, therefore, a barrier exists at junctions between hydrophilic and hydrophobic regions: the hydrophilic regions "attract" aqueous micro-droplets, while the hydrophobic regions "repel" such micro-droplets. Thus, these hydrophobic-hydrophilic junctions define relatively stable positions that a micro-droplet requires extra force to traverse. Because of the "repulsive" effects of the hydrophobic entrance regions h1, h2, h5, and h6 of the passages to heater1, heater2, vent1, and vent2 in FIG. 1, in comparison with the "attractive" effects of the substantially hydrophilic interiors of adjacent passages 1, 2, and 4, aqueous micro-droplets are restrained from penetrating into these hydrophobically-"protected" passages. Similarly, extra force is required to cause aqueous micro-droplets to pass the hydrophobically-protected regions h3 and h4, which therefore define stable regions between main passages 1-2 and Y-shaped main passage 3. In the case of predominantly hydrophobic micro-droplets, the hydrophobic and hydrophilic passage characteristics are reversed.

The present invention includes other methods of creating stable positions that will be apparent to one of skill in the art in view of the present description. For example, by placing a controllable vent adjacent to a passage with a valve, a stable position may be created when the valve is closed and the vent is open.

Because the effect of gravitational forces is negligible at the spatial dimensions used in these devices, surface tension may be exploited by designing local passage size differences within the device, perhaps in conjunction with adjacent hydrophobic regions. For example, since a narrowed passage will draw fluid from a larger passage by the capillary effects of surface tension, a relatively stable position can be created where a relatively narrow passage joins a relatively wider passage. This stable position may be reinforced by the presence of an adjacent hydrophobic region.

Stable positions can also be created by a local configuration of passages, preferably where a hydrophobically-protected side passage is vented to the exterior branches from a main passage. For example in FIG. 1, if a micro-droplet is being moved along passage 4 toward vent 3 by pressure applied to its left surface, and if valve3 is closed while valve4 is open, then the micro-droplet will come to reside at the stable position in passage 5 just beyond the entrance to the side passage leading to vent2. The micro-droplet will not penetrate the side passage to vent2 because of hydrophobic region h6, and it will not pass into passage 5 because all applied pressure will be released through vent2 to the exterior. Therefore this position, just beyond the side passage to vent2, is a stable position if valve3 and valve4 are properly actuated. (If valve4 is closed, the micro-droplet will continue moving through passage 5.) In this manner valved and vented side passages with hydrophobically-protected entrances also define stable positions.

In summary, hydrophobic regions h3 and h4 create adjacent stable positions in passages 1 and 2, respectively. Side passages to vent1 and vent2, hydrophobically-protected by regions h5 and h6, respectively, define stable regions adjacent and to the right of their junctions with passage 4.

Now turning to actuator and then to sub-assembly operations, micro-valve actuators, for example, valve1-valve6, preferably use meltable elements, for example, m1-m6, respectively, to reversibly obstruct, under the control of gas pressure, their respective controlled passages. For simplicity of illustration only, micro-valves are schematically illustrated FIG. 1 as having only one heater element, whereas, in a preferred subsequently-described embodiment (FIGS. 6A-B), they usually have three separate heaters and one temperature sensor (also up to three temperature sensors). Heater1 and heater2, which heat their respectively gas reservoirs, form thermally-controlled gas pressure generator actuators, which are part of micro-droplet motion and formation sub-assemblies. Heater 3, which heats passage 5, provides for thermal control of reactions in micro-droplets present in this passage. Results of reactions completed in passage 5 are detected in this exemplary microfluidic processor by an optical actuator, namely input optic conductor o1, which conducts incident radiation to the reaction region, and output optic conductor o2, which conducts scattered and emitted radiation from the sample for analysis. The incident radiation may be in the IR, visible, or UV bands as required for a particular application. Other detection means can be employed in other applications.

Operations of the sub-assemblies result from the coordinated operations of their component actuators. First, two micro-droplet motion actuators move micro-droplets along passages 1 and 2 by means of gas pressures generated by pressure generators controlled by heater1 and heater2, respectively. Next, sub-assembly metering1, which is composed of actuators valve1, heater1, inlet1, overflow1, and passage 1, meters a micro-droplet of determined volume from an aliquot of fluid introduced through port inlet1 in the following manner. Initially, if not already open, valve3 and valve1 are opened so that the side passage to vent1 is not blocked. Next, fluid introduced into inlet1, for example, by an external manual or robotic device, and flows up to the stable position created by the first hydrophobic region h3 just beyond the widening of passage 1, with any excess fluid flowing out through port overflow1. Region h1 prevents the introduced fluid from entering the side passage to heater1. Finally, controlled gas pressure generated by heater1 pinches the micro-droplet from the introduced fluid that lies between the junction of the side passage to heater1 and region h3, and propels it to just beyond the junction with the side passage to vent1. Region h5 prevents the micro-droplet from entering the side passage to vent1, and vent1 allows the propelling gas pressure to escape. Sub-assembly metering2 is constructed and operates similarly. (Optionally, valves, not illustrated, may be present adjacent to inlet1 and inlet2 in order to prevent passages 1 and 2 to refill after droplet metering.)

Sub-assembly mixing1 mixes two micro-droplets of differing constituents, which have been adjacently positioned at the stable position created by the junction of main passage 4 and the side passage to vent1, in the following manner. First, valve3 (and valve1 and valve1) are closed so that the adjacently situated micro-droplets in passage 4 can be propelled toward passage 5. Next, gas pressure is generated by heater 1, or by heater2, or by both, so that the two micro-droplets in passage 4 are moved to the stable position just beyond the junction of the side passage to vent2. Importantly, the generated pressure is controlled so that the motion is sufficiently rapid to mix the micro-droplets. Finally, the remaining sub-assembly illustrated in FIG. 1, sub-assembly reaction/detection1, which includes valve5, valve6, heater2, o1, o2, and passage 5, operates as follows. After a mixed micro-droplet of the correct composition is positioned in passage 5, this passage is sealed by closing valve5 and valve6. Next, heater3 is controlled to stimulate a reaction in the trapped micro-droplet, and the results of the stimulated reaction are optically detected by radiation conducted by o1 and o2.

FIG. 1 also illustrates leads and external connectors for the electrical and optical signals. For example, control and monitoring leads 8 for valve1 are schematically illustrated as two leads extending from the valve to the microfluidic processor's edge terminating in connectors 10. (A full and complete illustration of a micro-valve preferably has four, or six or more signal leads.) Although leads 8 are illustrated here as substantially straight, in most microfluidic processors with more actuators and leads, leads bend to avoid obstacles and other leads, or are combined where control requirements allow, or crossover each other separated by insulating films. The terminating connectors are preferably standardized, for example, as an array of pins that may be accommodated by an external socket, or, illustrated here, as rounded protrusions along processor edges that may be accepted by mating contacts in a receptacle in a control system. Also, exemplary optic conductors o1 and o2 are illustrated as extending substantially straight from the reaction/detection sub-assembly to optical couplings or connectors 7, also preferably standardized for routine connection to external radiation sources and detectors. Also, these conductors may need to bend or crossover obstacles. Optical conductors may comprise light pipes, optical fibers, or other means for spatial transmission of an optical signal.

According to a preferred embodiment of the invention, the number of terminating connectors required for the control of a plurality of actuators may be reduced by arranging/sharing, in the form of an array, the contact wiring to each actuator. The resulting compression of the number of terminating connectors advantageously simplifies communication with the entire microfluidic processor. Whereas each actuator requires two leads to complete an electrical circuit, according to a conventional arrangement of leads and contacts, a device comprising N actuators comprises 2N leads and 2N terminal contacts. By configuring the contact wiring in an array, however, the number of required terminal connectors can be reduced to as few as 2 N. For example, in a hypothetical device comprising 100 actuators, the number of external contacts can be reduced from 200 to 20. This greatly simplifies external wiring and device control.

As stated above, the compression is accomplished by arranging the contacts in an array. According to this arrangement, electrical contacts for the N actuators are configured in R rows and C columns such that the product RC=N, preferably where R is approximately equal to C, and most preferably where R=C. With this arrangement, actuators located in a given row share a common electrical contact. Similarly, actuators arranged in a given column also share a contact. Each actuator has a unique address, though, given by its unique row/column combination. Therefore, each actuator is individually actuatable by supplying electric current to the appropriate row-column combination.

It is also preferable that microfluidic processors for control by the present invention be physically standardized so that microfluidic processors designed for different reactions or analyses may be controlled by a single external control systems. Standardization would, for example, limit a microfluidic processor to only a few selected sizes. Electrical and optical connectors would be limited to standard forms, positions, and alignments. Inlet ports, overflow ports, vents, and so forth would be limited to standard forms and locations (for easy robotic access). A further preferable feature of microfluidic processors that promotes standardization is a self-description function. A processor may be described by providing its controllable and passive components, their mutual relations and interconnections, and, for each controllable component, the identity of the connectors for its control and monitoring signals. This self-descriptive information may be used by the control methods and systems to generate correct control signals at correct connectors for a particular microfluidic processor, otherwise such self-descriptive information must be explicitly entered by a user or "hard-coded" into the methods. This function may be variously implemented. For example, all the self-descriptive information may be stored in the microfluidic processors; alternatively, a processor may store a key to a database of this self-descriptive information which is stored elsewhere.

Further description of the construction and functioning of preferred microfluidic processors are provided in U.S. Pat. Nos. 6,048,734, 6,057,149, and 6,130,098, issued Apr. 11, 2000, May 2, 2000, and Oct. 10, 2000, respectively. These patents are incorporated herein in their entireties by reference without any admission that they are prior art to the inventions claimed herein.

Preferred Control Systems and Methods

This section describes preferred embodiments of these control systems and methods in view of the characteristics of preferred microfluidic devices. The control systems of the present invention control general digital microfluidic devices, and generate physical control information in proper modalities and sequences for causing the microfluidic devices to perform an intended reaction or analysis as a sequence of configurations or "state" transitions. Starting from an initial configuration, the microfluidic device is controlled to pass through a series of intermediary configurations, and to complete operation at a final configuration in which the intended reaction or analysis is performed. Each sequential configuration transition typically results from the creation of a new micro-droplet such as by metering, mixing, or moving a micro-droplet; the excitation of a micro-droplet by thermal or optical means, the detection of reaction results, and so forth. During these operations, a microfluidic device preferably generates monitoring signals that the control systems and methods use to insure successful completion of each operation.

In preferred embodiments, the control systems and methods of this invention control digital microfluidic devices that are also modularly and hierarchically constructed and controlled with electrical and optical signals as described above. In other words, in preferred embodiments the present invention controls microfluidic processors. More preferably, controlled microfluidic processors are implemented in a thermally-controlled technology and are physically standardized, also as described. Although the following description is largely limited to this more preferred embodiment, one of skill in the art will readily appreciate how to generalize the preferred embodiments described for the control of general microfluidic processors of other technologies, and also of general digital microfluidic devices.

Therefore, in this more preferred embodiment, the control systems of the present invention generate electrical (and optical) signals for controlling the individually-controllable device-level components of preferred thermally-controlled microfluidic processors. Optionally, the systems also receive electrical (and optical) monitoring signals. Then, the control methods of this invention command the control systems of the present invention to generate signals that reflect the modular and hierarchical construction of the preferred microfluidic processors. Signals controlling the individually-controllable device-level components are generated to cause these components to function together as actuators. Further, these signals are generated to cause the actuators to function together as sub-assemblies that manipulate micro-droplets. At the highest control level, these signals are generated to cause the sub-assemblies to function together so that the microfluidic processor as a whole performs an intended reaction or analysis, preferably by passing through a sequence of predetermined configurations designed to perform the reaction.

This hierarchical signal generation can also be considered as hierarchically constrained signal generation. To repeat, at the device level, a preferred microfluidic processor is composed of individually-controllable components that may be constructed according to a chosen nano-technology as a single atomic and elementary entity, not substantially or significantly decomposable for construction as a group of more elemental entities. The first constraint is that control signals are generated so that these individually-controllable components function together only as actuators, that is so that the component control signals are determined by requested actuator control functions. A second constraint is then that the actuator control functions are generated so that the separate, controllable actuators act together only as sub-assemblies manipulating processing, that is so that actuator control functions are determined by requested sub-assembly control function, also perhaps represented as sub-assembly control signals. Finally, the "sub-assembly control" functions are requested according to a script, or program, so that the microfluidic processor performs configurations leading from an initial configuration to a configuration in which the intended reaction or analysis is performed.

From either viewpoint, a microfluidic processor is preferably controlled according to the present invention by "programming" the control system so that the sub-assemblies function to achieve the correct configurations in the correct sequence necessary to complete a reaction. This "programming" is in terms of sub-assembly function, such as the creation, mixing, movement, thermal (or other) excitation, and detection of reaction results in micro-droplets. In other words, this "programming" is in terms, intuitively familiar from the chemistry laboratory where reagent are measured, mixed, heated, and so forth. It is the systems and methods of the present invention that then convert, or interpret, or otherwise process such a "sub-assembly program" to generate the correct detailed control signals for all the individually-controllable microfluidic processor components, and preferably generate these signals so that the individual microfluidic processor components function as actuators and that the actuators function as sub-assemblies. Stated differently, these methods of the present invention, performed by the systems of the present invention, enforce the described hierarchical constraints and encapsulate the device-level detail of a controlled microfluidic processor. The end user is presented with a vastly simplified control, or "programming" task.

These "sub-assembly programs" are performed by control systems of the present invention which are preferably structured as an at least two-level hierarchy. At the highest level are one or more programmable components, for example, a PC-type computer or an embedded microprocessor. At the next level is include peripheral interface circuitry which is under control of the programmable components and which actually generates and responds to the electrical (and optical) control signals. The methods of the present invention are then preferably implemented as programs for this programmable apparatus that cause the programmable apparatus to control the peripheral circuitry to generate and receive control signals passed to and from the individually-controllable components in the controlled microfluidic processor.

In more detail, the "sub-assembly" programs, which are supplied by a user to cause a microfluidic processor to perform an intended reaction or analysis, are alternatively lists of sub-assembly functions that the processor is caused to perform in order, or lists of processor configurations that the processor is caused to assume in order. Optionally, these program lists may include commands for testing, branching, or iteration. Testing and branching are advantageous where a microfluidic processor generates monitoring signals and where the systems and methods of this invention make the monitored information available at the "sub-assembly program" level. The methods of the present invention then convert, compile, interpret, or otherwise cause the programmable control systems acting through the peripheral control circuitry to generate the requested hierarchically structured or constrained control signals for the microfluidic processor.

In a preferred implementation, the hierarchical structure of control signals, or, equivalently, the constraints on control signal generation, may then be preferably implemented as a corresponding hierarchical structure of signal generation functions. In such a structure, when functions at a particular level act in a correctly constrained manner only by means of functions of lower levels, signal structure and constraints will be automatically and easily maintained at all levels as long as the lower-level functions also maintain their lower-level constraints. For example, "sub-assembly-level" functions perform micro-droplet functions by requesting correct sequences of "actuator-level" functions without concern for how actuators are implemented by individual processor components. "Actuator-level" functions request correct sequences of device commands, without concern for how a thermally-controlled microfluidic processor is implemented. Finally, only "component-level" functions actually convert user programs to control signals generation and actually receive monitoring signals, and contain most details of thermally-controlled device implementation.

Such a hierarchical organization of control functions, along with attendant data, may be expressed in many suitable programming languages and software engineering paradigms. On one hand, the methods of the present invention may wait to translate user-provided, sub-assembly programs into function requests until operation of the controlled microfluidic processor. For example, component, actuator, and sub-assembly control functions may be implemented as objects in an object-oriented programming system (using an object-oriented language such as C++). Here, the control functions are object methods and are executed in sequence in response to method message exchanged during operation. Similarly, the methods may be implemented as an interpretive system which also invokes functions only during operation. On the other hand, these methods may translate programs during an initial compilation step. For example, the control functions of the various levels may be implemented as macros (using a procedural language with a macro facility such as C) in a procedural paradigm, which translate each sub-assembly command into a corresponding plurality of actuator commands, so that programs are translated into instructions for the programmable apparatus. Mixed implementations are possible. For example, control functions can be represented as library routines, or higher-level functions may be objects and lower-level functions may be macros.

Data for the methods of the present invention includes, for example, the current configuration of the microfluidic processor and the current state of the actuators and components in the processor. These data can (including micro-droplet changes between successive configurations) be represented in manners advantageously suited to use by micro-droplet control functions.

Control Methods

This sub-section describes preferred structures for the control signal generation functions along with preferred structures for their data and parameters, both for a thermally-controlled microfluidic processor of the preferred implementation. The following descriptions apply to any implementation paradigm: for implementation with objects, the object hierarchy is described; for procedural implementation with macros, the macro inclusion hierarchy is described; for procedural implementation with library routines, the procedure invocation hierarchy is described. One of skill in the art will be readily able to apply the following description to the chosen paradigm. Also, although the following describes a currently preferred allocation of functions to hierarchical levels, the methods of this invention are readily adaptable to other function allocations, and even to other function definitions. In particular, the grouping of components into actuators may be implementation- and technology-dependent. Also, there may be fewer functional levels, for example, just sub-assembly and actuator levels, or more functional levels, where advantageous.

Preferred Functional Structures

Figure 2:
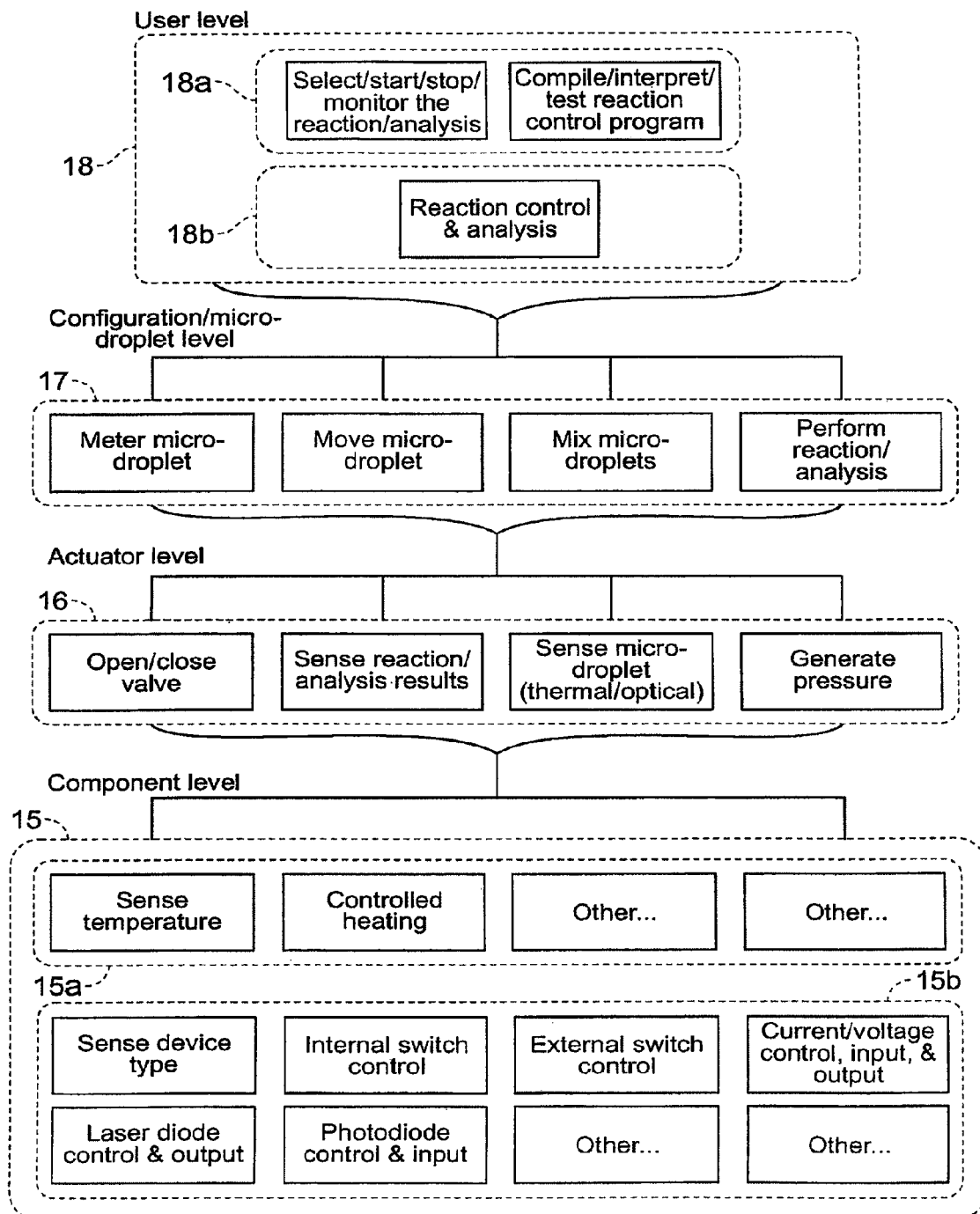
FIG. 2 illustrates a functional hierarchy of the present invention.

FIG. 2 illustrates an exemplary and non-limiting, but preferred, hierarchical organization of signal generation functions for a thermally-controlled microfluidic processor implemented in a preferred technology. This figure illustrates four function levels, a component level, an actuator level, a sub-assembly (which is functionally identified in FIG. 2 as a configuration or micro-droplet level), and a user level. Since higher-level function act only by invoking lower-level functions, they necessarily abide not only by their own constraints but also by the constraints of all lower-level functions. As described, this insures that processor control signals ultimately generated abide by the entire preferred hierarchical structure and constraints.

First, the lowest-level functions are component-level functions 15b, which are preferably the only functions that directly cause generation of electrical and optical signals for control of the individually-controllable microfluidic processor components. For example, the "current/voltage control" primitive function causes the control system to generate or monitor specified electrical control signals. The "external switch control" function causes the control system to switch these signal generators to signal connectors. (The "internal switch control" function controls switches internal to a microfluidic processor, which, if present, route electrical control signals from processor to connectors to internal components.) Therefore, the joint action of these two functions generates and monitors electrical control signals between the control system and electrically-controlled processor components. Correct connectors for component control of particular components may be determined from the previously-described self-descriptive microfluidic processor data, which includes such connector-component information. In the case of preferred self-descriptive microfluidic processors, this self-descriptive information, or a key to it, can be obtained from the microfluidic processor itself. The function reading this information from a processor is called the "sense device type" function. Finally, the functions "laser diode control" and "photodiode control" provide similar control of optical signals.

Level 15 may also include certain additional simple functions 15a, which implement actions somewhat more complex than the actions of atomically implementable device components, but which are nevertheless simple and best classified as components rather than as actuators. Functions 15a may invoke functions 15b or other functions 15a. An example of such a generalized component-level function is the "sense temperature" function, which outputs the temperature at a given sensor element. Given a specified (resistive) temperature monitor element, its external contacts may be indicated by descriptive microfluidic processor data. The electrical output of these indicated contacts may then be monitored by the "current/voltage control" and "external switch control" functions, and then converted to a temperature in view of known physical properties of the given sensor. The "controlled heating" may apply, using the more primitive control and switch functions, a given power to a given heater element, or may adjust the applied power in view of the output of a "sense temperature" function to achieve a given temperature.

These component-level functions and their suggested implementations are not intended to be limiting. First, other and additional component-level functions may be defined; the listed functions are exemplary and not exhaustive. Second, since component-level functions are typically determined by the implementation technologies, they typically will differ for microfluidic processors of different technology. Even within a single technology, details of heating, sensing, and so forth differ in different specific microfluidic processor implementations. Further, even for a single processor type, different preferred embodiments may package the primitive and generalized component-level functions differently.

Actuator-level 16 includes functions that control groups of one or more usually interconnected components in a manner and sequence so that they function together to achieve a particular actuator-type function. Actuator-type functions are those typically associated with the "plumbing" or "machinery" necessary to implement a chemical reaction, such as opening or closing a micro-valve in the microfluidic processor, generating pressure, sensing quantities, and so forth. For example, a "sense reaction results" function may be optically implemented. It may act by means of the "laser diode control" and the "photodiode control" functions, first, to cause the proper incident radiation to be provided to the proper external optical connectors in order that reaction results are illuminated, and second, to cause scattered or emitted radiation to be observed. A "sense micro-droplet" function may sense the presence or absence of a micro-droplet by, in effect, measuring a local thermal capacity. Thus, this actuator function may, first, provide a given quantity of heat by means of the "controlled heating" function, and second, determine the temperature response by means of the "sense temperature" function. A greater temperature increase indicates a lower heat capacity indicative of the absence of a micro-droplet, and vice versa. This function may also be optically implemented to determine micro-droplet presence or absence in a region by sensing optical properties of the region in a manner similar to the "sense reaction results" function. A "generate pressure" function may use the "controlled heating" function at a given power or to a given temperature in order to heat gas in a reservoir to increased pressure. Generated pressure may be monitored with a pressure sensor if available in the microfluidic processor. Finally, the important "open/close" valve functions are described subsequently.

Information describing an actuator's individual components and interconnection indexed by an actuator identifier may be available from self-descriptive processor data. In this case, simply an actuator identifier may be specified to the actuator functions, which then automatically determine component parts from the self-descriptive processor data without requiring user attention or input of this information. In turn, component information, for example, connector identification, may be automatically determined by component-level functions from this same data.

Actuator-type functions are expected to be more standardized than component-level functions because they reflect facilities needed by virtually all microfluidic reaction processors. For example, virtually all microfluidic processors will have micro-valves with open and close valve functions. Nevertheless, the actuator-level functions and their suggested implementations described herein are exemplary, and not exhaustive or intended to be limiting. For example, certain component-level functions, especially generalized functions 15*a*, may be considered actuator functions in different implementations. Second, even though many of these types of actuator functions may be substantially similar in different processors, their implementation may differ from those suggested above depending on the processor components available in the implementation technology. Third, different actuator functions may be present to take advantage of different component types present on different processors, for example, a wider range of sensing actuators may be present to take advantage of a broader sensing technology.

Configuration/micro-droplet 17 functions (performed, generally, by sub-assemblies) are those that act on micro-droplets, preferably invoking primarily actuator functions 16 so that micro-droplets move from stable position to stable position. Therefore, the configuration/micro-droplet 17 functions provide that the microfluidic processor progresses through configurations that are defined by the micro-droplets present in a processor and their stable positions. In other words, a micro-droplet function starts with one or more micro-droplets at stable positions and invokes actuator functions so that upon completion the one or more micro-droplets are again at different stable positions. These functions do not complete with micro-droplets at unstable positions, positions from which a micro-droplet may spontaneously move and in an indeterminate manner. Micro-droplets at unstable positions would therefore make predictable and orderly operation of a microfluidic processor impossible, and this situation is to be avoided.

Input information for micro-droplet functions includes positions of the micro-droplets to be acted on. Preferably, this information may be obtained from an initial processor configuration, which is updated with new micro-droplet positions, to a final configuration upon function termination. Also where sense actuators are present, these functions may check micro-droplet position and report an error if the measured position and intended position are inconsistent. Even more preferably, using micro-droplet position and processor self-descriptive data, these functions automatically determine which actuators to invoke for achieving the intended result. Otherwise, micro-droplet position, and possibly also the correct actuators, must be determined by a user (assuming prior micro-droplet operations were successful) and then input to these functions.

Micro-droplet-level functions are preferably provided to correspond to standard types of chemistry laboratory operations, such as measuring, mixing, heating, and so forth. Thus, functions 17 usually include: functions to meter a micro-droplet from a fluid source in order to form a new micro-droplet of known volume, to move a micro-droplet from one stable position to another stable position, to mix an inhomogeneous micro-droplet to form a homogeneous micro-droplet, to perform a reaction by thermal or other type of excitation, and so forth.

Because microfluidic processors of this invention act in a digital manner by manipulating micro-droplets to perform chemical or biological analysis, basic micro-droplet functions types are largely "microfluidic processor independent." Certain micro-droplet functions, for example, separation of micro-droplet constituents, may be added where required by a certain type of reaction. Alternatively, certain combinations of basic micro-droplet functions may be made available as a single function for efficiency. Variation in function details and function implementation may occur between different technologies and processor types. Preferred implementations of these functions for preferred processors are subsequently described.

User-level 18 functions do the work useful to an end user, performing and monitoring an intended reaction or analysis in a microfluidic processor. Functions 18*a*, "protocol/compiler/interpreter" functions, direct a microfluidic processor to actually carry out an intended reaction. These key functions interpret, convert, compile, or otherwise process a user-provided reaction program, preferably specified substantially as a sequence of micro-droplet-level functions that prepare a micro-droplet containing the necessary reactants, cause the intended reaction to occur in this prepared micro-droplet, and then detect or sense reaction results. As described, reactions are preferably "programmed" largely by invoking micro-droplet-level functions, and rely on the function hierarchy of this invention to ultimately generate the necessary control signals on the correct connectors to cause a microfluidic processor to perform the invoked functions. Because micro-droplet functions, as well as actuator and component function, encapsulate most details of processor actuator operation, users may advantageously specify reactions in terms corresponding to routine chemical laboratory operations. Self-descriptive microfluidic processor data permits this specification without attention to internal processor details.

User-level 18 may also contain operator-type functions 18*b*, which provide for microfluidic processor control by permitting the selection of the reaction or analysis "program" to be performed by a microfluidic processor, by initiating the selected reaction "program" after readying the processor, and by terminating the reaction and returning the sensed reaction results, and so forth. Operator function may also provide for monitoring a microfluidic processor as it processes a reaction. For example, monitoring functions may show on an appropriate display device a graphical (or otherwise formatted) portrayal of the current state of a microfluidic processor such as the current position of micro-droplets, the current state of microfluidic processor actuators and components, and so forth, along with indications of the "program" steps already performed and yet to be performed. Optionally, operator-type functions may include program development and debugging tools, for example, tools for entering micro-droplet function commands, for "single-stepping" a processor through a program, and for further facilities familiar from programming environments for computer systems. Since a function of a particular hierarchical level performs its actions by making requests of functions, the exchange of requests is fundamental and is variously referred to herein. For example, a higher-level function may generate, or send, or transmit, or so forth a request, which a lower-level function then processes, or accepts, or receives, or so forth. Alternatively, a higher-level function may provide a request to a lower-level function.

Preferred Data Structures

The hierarchically arranged signal-generating functions preferably utilize and maintain certain data, for example, self-descriptive data for the microfluidic processor, data descriptive of the current processor state, and the configuration or state of micro-droplets present in the processor. Self-descriptive data for a microfluidic processor generally specifies the processor's components, how they are interconnected, and by what external contacts they are controlled. For example, processor components may be described as a list of atomic components, their type, properties, and where controllable, control connectors. Actuators may be also described as a list of their type, properties, and atomic components out of which they are constructed. The external contacts controlling the components of an actuator can be determined from the component of the actuator and the connectors controlling these components. Component interconnection may be described by a list of the passages, hydrophobic regions, inlet ports, outlet ports, vents, and so forth, along with indications of the connectivity of these elements, which may be represented as a network flow diagram.

The self-descriptive processor data may be automatically supplied, preferably by the microfluidic processor, or less preferably by the control system or by both acting in combination. In one embodiment, a ROM-type memory (or EPROM, or other permanent or quasi-permanent memory) is embedded in or on a microfluidic processor containing at least this processor-descriptive data. Alternatively, this memory can be limited to a few ($\leq$10) bytes that store only key-type information for lookup in a control system database retrieving complete self-descriptive data. In another embodiment, machine-readable indicia, such as a bar code, or human-readable indicia, such as a serial number, may be provided on a microfluidic processor. The "sense device type" component function obtains this self-descriptive data either by accessing the embedded microfluidic processor memory by means of standardized connectors (for example connections "1, 2, 3, and 4" on all microfluidic processors), or by reading machine-readable indicia, or by manual input of human-readable indicia.

Self-descriptive microfluidic processor data preferably permits simplified parameterization of the component and actuator-level functions by the symbolically identified components and actuators. For example, a "controlled heating" function may be applied to "heater-6B," wherein "heater-6B" is identified by the functions in the self-descriptive data. In contrast, applying a "controlled heating" function to external contacts 39, 42, 43, and 68 is less flexible. An "open/close valve" function may be more preferably applied to "valve-12," instead of to "valve-12"'s components or to their connectors. Information describing a microfluidic processor also preferably includes the state of the symbolically-identified components and actuators. For example, the current temperature, or the past heating of "heater-6B" is 80 C; valve-12" is currently "open"; and so forth.

Function data further includes micro-droplet configuration or "state" data, which includes a list of the micro-droplets currently present in a microfluidic processor and their composition and current position. Micro-droplet composition may, for example, be recorded by the source or sources from which the micro-droplet was created. Micro-droplet position records its current unstable position occurring only transiently during transitions between configurations. Micro-droplets may be symbolically specified in the configuration, for example, the sixth micro-droplet created being "micro-droplet-6," and micro-droplet functions may then be applied to symbolically specified micro-droplets. For example, when the "move micro-droplet" function is applied to "micro-droplet-6" the function determines this micro-droplet's current position from the current processor configuration. From this determined position, the "move micro-droplet" function next determines from the self-descriptive processor data the correct actuators to invoke to move "micro-droplet-6," and from current state information, the current state of these actuators. When the determined actuators are invoked their components, their component's connectors, and their component's state are similarly determined. Alternatively, in simpler but less preferred embodiments, the actuators, components, and connectors may be pre-specified.

Finally, user-level operator monitoring and display functions may display this function data. For example, animation of microfluidic processor operation may be displayed as a map of the microfluidic processor components and their connections along with the current position of the micro-droplet and the current component activations. Limited aspects of the current state may also be operator-selected for display.

In one embodiment of the present invention, a microfluidic processor may be represented in an object-oriented programming paradigm. In an exemplary object representation, where some or all of the components, actuators, micro-droplets, and so forth may be represented as objects, the maintained data would be represented as object instance data, defining for each object its type, state, geometric relation to other objects, and so forth. The control functions would be methods manipulating the component, actuator, and micro-droplet objects. These microfluidic processor control function may be represented in other programming paradigms where the maintained data may be represented as lists, tables, trees, or other known data structures.

Control Systems

A control system of the present invention preferably has a distributed and hierarchical structure, generally paralleling the hierarchical control function structure illustrated in FIG. 2. Preferably, lowest-level control functions, such as component-level functions 15 and actuator-level functions 16, are implemented in system interface hardware configured for direct connection to a controlled microfluidic processor (for example, data acquisition and control board 26 in FIG. 3A), while highest-level functions, user-level functions 18, especially operator functions 18b, are implemented in system user hardware configured for user interaction (for example, personal computer 27 in FIG. 3A). Intermediate function levels, reaction control 18a level, micro-droplet level 17 (or configuration level), and actuator level 16 may be implemented in the interface or in the user hardware, or in an intermediary hardware level, as convenient. (Micro-droplet level 17 functions are those functions performed by the physical sub-assemblies described above, which in turn are composed of actuators and perhaps individual components.)

Control systems, and especially system interface hardware, may be implemented with electronic microprocessor, such as those available from Intel, Motorola or other electronic suppliers. To avoid confusion, such control system electronic processors will be always called "microprocessors," while microfluidic processors will be called both "microfluidic processors" and simply "processors."

Figure 3A:
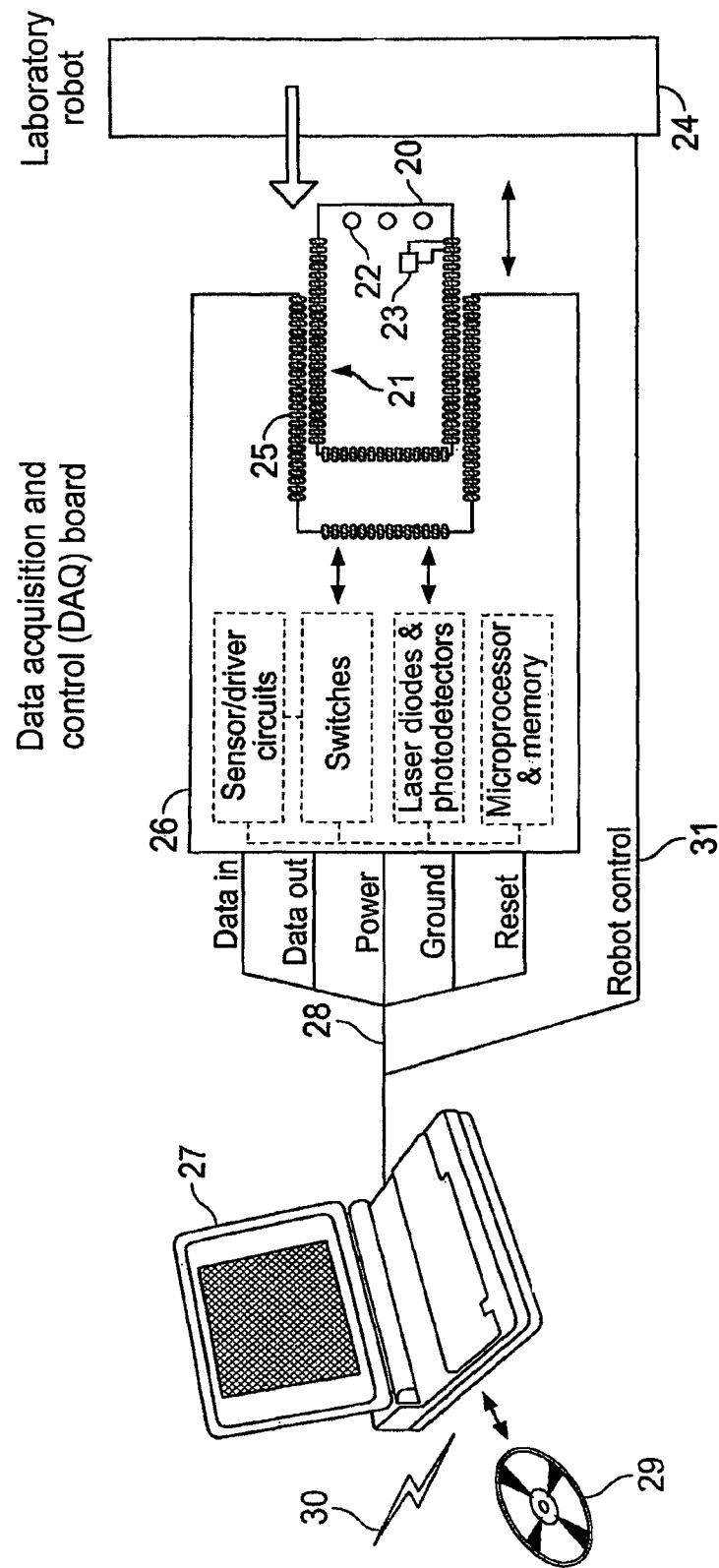
FIGS. 3A-B illustrate preferred control system structure of the present invention.

FIG. 3A illustrates an exemplary preferred two-level control. Microfluidic processor 20 is illustrated as having a standardized physical configuration including a standardized size, shape, and electrical and optical connectors 21, which are arranged along three edges of the rectangular processor. The processor is shown being inserted into (or removed from) an interface hardware receptacle having electrical and optical connectors 25 standardized to mate with contacts 21 of the processor. Most connectors are for electrical signals, while certain are for optical signals (IR, visible, UV) in the case of optically monitored or excited microfluidic processors. Further, exemplary microfluidic processor 20 is illustrated with three inlet ports 22 for accepting fluid reagents or samples. Preferably, these inlet ports are in standard position on the processor so that laboratory robot 24, where available, may be easily programmed for automatic loading of ports of several types of microfluidic processors. Otherwise, the ports should be accessible for manual loading. Where possible, reagents may also be pre-packaged on a microfluidic processor. Additionally, processor 20 has micro-circuit 23 accessible through certain standard connectors for storing at least self-descriptive processor information. Alternately, processor 20 may bear indicia, such as a bar code, indicating device type or further information.

Illustrated first-level, interface hardware comprises data acquisition ("DAQ") board 26 directly connected to microfluidic processor 20. A preferred DAQ board is programmable, for example including an embedded microprocessor (such as those produced by Intel, Motorola, etc.) with RAM memory (for example, 1-8 MB), which controls electrical and optical sensor/driver circuits and switches between outputs of these circuits and connectors 25. The sensor/driver circuits are switched among connectors 25 under microprocessor control to provide control signals to the microfluidic processor, or to receive monitoring signals. Optical signaling components, for example laser diode radiation sources and photodiode radiation detectors, are similarly controlled by the microprocessor. The DAQ board also preferably includes a standardized external interface that permit links to a broad range of higher-level portions of the control system. Illustrated here is generic 5-wire, bi-directional, serial interface 28, similar to such standard interfaces as UART, USB, Firewire, Ethernet, and so forth, all of which may be used in this invention. In other embodiments, the DAQ board can be configured to plug into the busses of higher-level control systems. User hardware preferably communicates with a DAQ by means of message exchange according to a standard protocol.

A DAQ board with sufficient microprocessor and memory resources may perform virtually all control functions. For example, such a board may perform component-level functions 15, actuator-level functions 16, micro-droplet-level functions 17, and reaction-control function 18a. In this preferred embodiment, only the user interface functions are more efficiently performed on user hardware. Such a capable DAQ board would function with most user hardware of limited resources. With a less capable DAQ-board, control functions may be advantageously shifted to user hardware, starting with higher-level reaction control functions and proceeding lower in the function hierarchy. In the former case, limited monitoring messages would need to be exchanged between the DAQ board and the user hardware; in the latter case, user hardware would send parameterized messages to the DAQ board invoking lower-level functions. These messages may be divided into packets for actual transfer across the DAQ interface, and the transfer may be error checked.

In alternative embodiments, certain lowest-level control functions may be offloaded from the DAQ board onto control hardware embedded in processor 20 itself, for example, onto micro-circuit 23. For example, this circuit could serve as an internal switch so that a smaller number of external contacts 21 may be switched among a larger number of control or monitoring leads on the processor, thus conserving external contacts. Other certain component control functions may be offloaded to the microfluidic processor.

User hardware (also called herein a "host") is the top-level of the control systems of this invention. In most embodiments user hardware performs at least user interface functions 18b in FIG. 2. In response to user input, these top-level functions have final control of starting, monitoring, and stopping a reaction on a processor, and of reporting reaction results. The user hardware, or host, further may perform administrative functions, among which may be managing the software instructions and data for itself and for attached DAQ boards. Software instructions for causing the host to perform its functions may be loaded from computer-readable media, such as optical disk 29, or may be downloaded from network interconnection 30. Data may also be loaded to the host computer from computer readable media, in particular a database of microfluidic processor descriptive data may be loaded into the host. Further, the host may "download" software instructions and data to the DAQ board, where such is not already resident by being stored in, for example, a ROM/Flash memory card or a small hard disk. This downloaded software and data loaded causes the DAQ board to perform its assigned tasks. User hardware is preferably programmable, for example, with microprocessor, memory, and storage, and connects to a controlled DAQ board by means of the standardized interface on the DAQ board.

The hierarchical control systems of this invention—the user hardware, the DAQ board and, optionally, the microfluidic processor itself—may conveniently be constructed to a number of different design points suitable for different applications. As illustrated in FIG. 3A, user hardware 27 may be a laptop PC, typically with a microprocessor of 500 Mhz or greater speed, with 64 MB or more of memory, and connected to stand-alone DAQ board 26 by bi-directional UART 28 which plugs into the PC. This implementation is suitable for portable medium-throughput applications or for light in-laboratory use.

A still more portable design point is a handheld analysis system, in which host 27 may be a palmtop or other type of handheld type computer, DAQ board 26 plugs into an "expansion" socket or other receptacle or plug on the handheld host, and microfluidic processor 20 in turn plugs into a DAQ board receptacle. The handheld may also include remote communication interfaces, such as wireless access. This design point would have medical applications in a doctor's office, or at bedside, or in an emergency situation, or so forth. It may also have industrial applications for the "field" of manufacturing processes of industrial chemicals. Other applications will be readily apparent to those of skill in the art.

Another design point is a less portable, but higher throughput laboratory analysis system in which host 27 may be any PC-type or workstation-type laboratory computer and one or more DAQ boards 26 with microfluidic processors 20 arranged in a number of appropriate configurations. In a simple arrangement, the DAQ board may reside in a tabletop holder (not illustrated) which connects to host 27 via data cable 28. Alternatively, multiple microfluidic processors 20 with their associated DAQ boards may reside in a single holder, or multiple holders, and may be connected to host 27 by a network connections such as Ethernet connections. For more complete laboratory automation, one or more processors 20 with their associated DAQ boards may be arranged so that samples or reactants may be introduced into the processors by one or more standard laboratory robots. In FIG. 3A this is illustrated by laboratory robot 24 which has access to inlet ports 22 of microfluidic processor 20. This laboratory robot is controlled via cable 31 from host 27 so that microfluidic processor loading and processor operation can be conveniently and automatically controlled from a single computer. Alternatively, the robot may be controlled by a separate computer.

A broad range of further design points that are suitable for various other applications will be apparent to those of skill in the art.

Preferred Thermally-Controlled Embodiment

This section describes more preferred thermally-controlled microfluidic devices and their more preferred control systems and methods; furthermore, this section describes additional embodiments.

In a more preferred embodiment, this systems and methods of this invention are applied to thermally-controlled microfluidic processors, such as is illustrated in FIG. 1. This subsection describes in order the systems and the methods of this more preferred embodiment.

DAQ Board Architecture

The DAQ board of this embodiment is relatively more capable, and therefore may be interfaced to user equipment, or hosts, of a wide range of capabilities. DAQ board architecture includes both a preferred hardware architecture and a preferred system software architecture, described herein.

Hardware Architecture

Figure 3B:
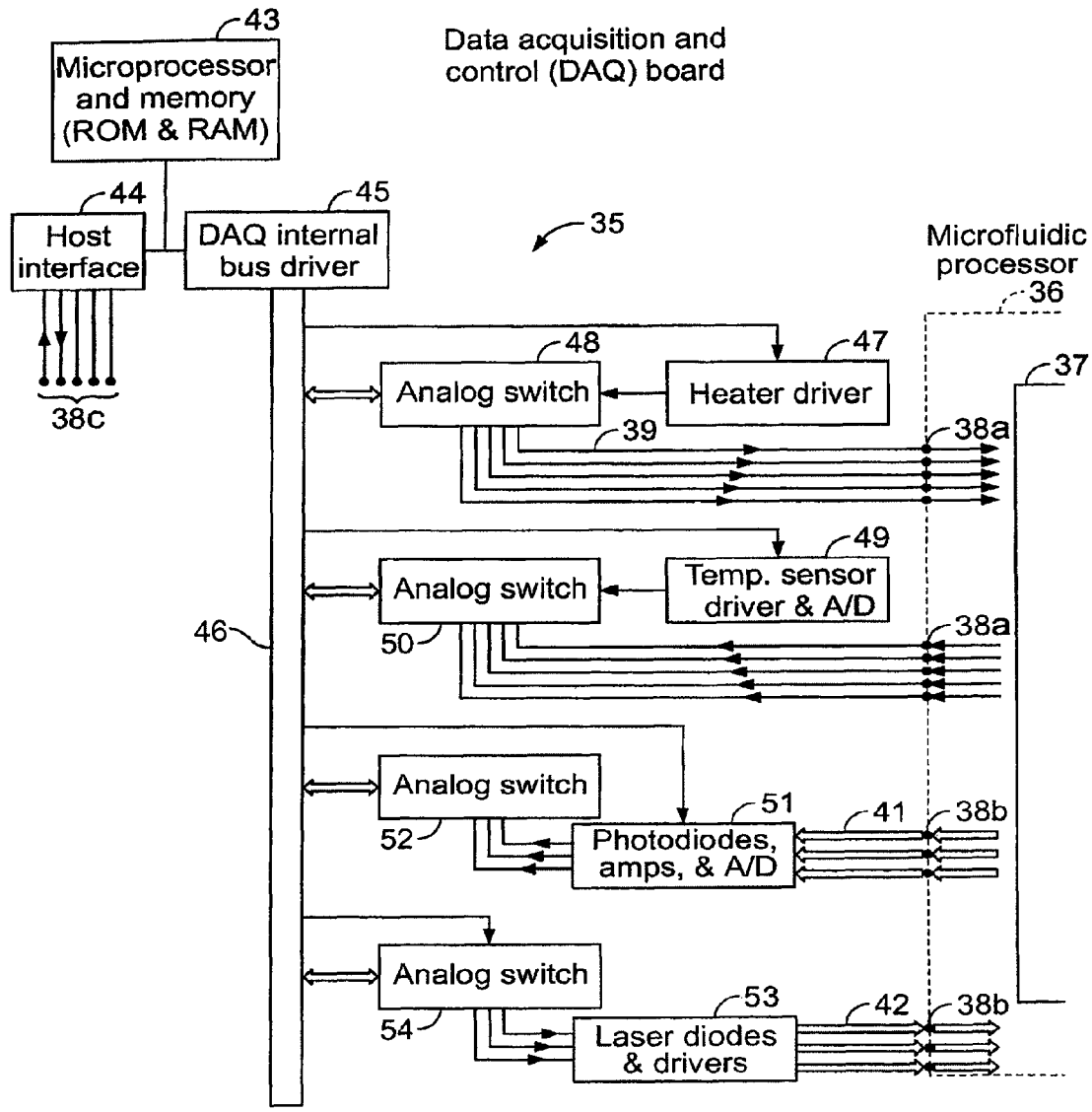

FIG. 3B illustrates a preferred hardware architecture for DAQ boards of this embodiment. First, DAQ boards have one or more receptacles, slots, sockets, or so forth where one or more replaceable microfluidic processors may be accommodated in a firmly supporting manner with good contact to its external connectors. Microfluidic processors, are preferably mounted on a relatively tough substrate, for example a PCB board. Processor substrates are standardized to have one, or at most a few, selected shapes, sizes, and connector arrangements for easy replacement in one, or at most a few, corresponding DAQ board receptacle types. Thus, FIG. 3B illustrates microfluidic processor 37 mounted on substrate 36.

Standardized electrical connectors 38a connect between both electrical control lines 39 and lines on substrate 36 leading to microfluidic processor 37, and also between electrical monitoring lines 40 and corresponding substrate lines. Optical connectors 38b connect between both optical conductors 42 from DAQ board light sources and optical conductors 41 to DAQ board light sensors and corresponding optical conductors on processor substrate 36 also leading to the microfluidic processor. The electrical connectors, which may have many embodiments, are illustrated here as edge connectors that are engaged when the processor substrate is inserted in a DAQ board receptacle. Alternatively, connectors may be suitable for engaging a flexible ribbon cable, or may be multi-pin sockets, or so forth. The optical connectors may be of types known for connecting fiber-optic cables.

Host computer interface 44 is preferably selected according to the type of host used in a particular control system. For example, for handheld hosts the DAQ board may plug into an available slot or interface integrated into the handheld device. For laboratory systems using PC or workstation type hosts, the DAQ board provides a modular, simple, and preferably standardized connector and interface, for example, suitable for a USB, or a Firewire, or an Ethernet cable connection. Illustrated in FIG. 3B is a simple, bi-directional, UART serial interface with cable connector 38c. The illustrated interface has serial data-in and data-out lines and a reset line, which should be capable of bringing the DAQ board to a known state. This interface also provides power and ground lines.

The DAQ board is preferably externally powered by a host computer (or by a standalone holder). Power may be supplied at standard voltages, for example, at +12 V, +5 V, or other voltage, which the board itself converts to and regulates at required internal voltages. Preferably, a DAQ board is able to negotiate with host (or with its holder) concerning the power requirements of the board and an attached microfluidic processor, and to generate an error indication if the power supply does not meet requirements. Similar power negotiations are known from USB interfaces employed in personal computers.

FIG. 3B generally illustrates a preferred microprocessor-based DAQ board architecture. Microprocessor and memory 43 (such as RAM or ROM) communicate with both host interface controller 44 and with internal bus controller 45 over a microprocessor bus optimized for high speed communication with a few devices. Internal bus 46 is typically different from the microprocessor bus because it is designed and optimized for controlling and monitoring interfaces to numerous, lower-speed peripheral circuit controllers. Internal bus controller 45 links the microprocessor bus bi-directionally with the internal bus. Alternatively, the microprocessor bus may directly connect to peripheral circuit controllers, and the internal bus may be eliminated. Although not illustrated, the DAQ board may also include one or more hard disks of small form factor, readers for flash devices, RAM, or other interfaces.

In an economical embodiment, the signal generation and sensing function includes peripheral circuitry in which a smaller number of bus-controlled signal generation and monitoring circuits are switched (or multiplexed) by bus-controlled signal switching circuits among a larger number of leads or lines for connection to a microfluidic processor. Thus, the microprocessor controls microfluidic processor control-signals by controlling the signal generation and signal switching circuits by means of the internal bus 46. Alternatively, a driver/sensor circuit may be provided for each external connector, and the signal switches may be eliminated.

Accordingly, FIG. 3B illustrates heater driver 47 circuit, controlled by bus 46, with relatively few outputs leads being switched or routed by analog switch 48, also controlled by bus 46, among relatively more numerous control lines 39. The heater driver circuits may control heater elements on the microfluidic processor by providing either a source of constant voltage or current, or a source of pulses of controlled width or frequency, or of sources of signals of other modulation schemes. Heater elements should be controllable from zero power up to a maximum power, where the maximum is preferably from 1.0 to 2.0 W, and more preferably from 0.5 to 2.5 W. Microfluidic processors also typically have at least one cooling device, for example a Peltier device, which is used to establish a baseline operating temperature appropriate to the reaction or analysis being performed, for example, a room temperature of approximately 25° C. or lower. DAQ boards, therefore, also include peripheral circuitry, controllable by the microprocessor for controlling such a cooling device.

Similarly, monitoring signals generated in a microfluidic processor and conducted on relatively more numerous monitoring lines 40 are switched by switch 50, under control of bus 46, to one of relatively fewer number of digital sensor circuits 49, which may be an analog-to-digital converter of similar. Also, the sensor circuits may also provide signals to activate sensors where needed. The digitized monitoring signals are then transmitted to microprocessor and memory 43 over internal bus 46. Monitoring signals are typically generated by temperature detectors, preferably at least one detector accompanying and for control of each resistive heater. Temperature detectors are preferably resistive temperature detectors (preferably of platinum) with resistance in the range of $1000\Omega$ to $4000\Omega$ at 25° C. Since temperature measurements preferably have an accuracy and resolution of approximately 0.5° C., temperature sensor circuitry should be able to measure a resistance (for platinum temperature detectors) in the above range with an accuracy and resolution of better than approximately 0.25%, and more preferably better than approximately 0.13%.

Similar switch-based control may be used for optical signals. FIG. 3B illustrates bus-controlled analog switch 54 which switches a bus-provided control signal to relatively numerous laser diodes and drivers 53. Laser diode output is then conducted by light conductors 42 to substrate 36, and then to microfluidic processor 37. To provide excitation light to a microfluidic processor, a DAQ board has at least one, and preferably two or more, laser diodes (or other controllable light sources) with a power range of 1-10 mW and with wavelengths useful for reaction excitation and detection. Preferably, a plurality of laser diodes are provided with a plurality of wavelengths specific to plurality of different microfluidic processors performing a plurality of different reactions or analyses. Further, the laser diodes, or their optic conductors, may optionally be provided with optic elements, such as filters or polarizers. Driver circuits for the laser diodes are preferably controllable (by the microprocessor) so that laser diode output power can be adjusted over their range.

Optical monitoring signals are received over light conductors 41 and are sensed by photodiodes 51 (or other light sensors). The digitized photodiode output is switched onto the bus by switches 54. To monitor light returned from a microfluidic processor, a DAQ board preferably has one or more photodiodes, preferably four, or five, or more photodiodes with characteristics, such as wavelength responsiveness, dark current, quantum efficiency, and so forth, specific to the reactions or analysis. Preferably, a plurality of photodiodes are provided with a variety of characteristics specific to a variety of microfluidic processors performing a variety of reactions or analyses. Further, the photodiodes, or the optic conductors, may optionally be provided with optic elements, such as spectral filters, to adapt their responsiveness to the reaction. Photodiode digitization circuits preferably have adjustable gains and ranges to accommodate photodiodes of different characteristics.

Alternatively, where controllable optical switches are economically available, this architecture illustrated may be replaced by a switched architecture similar to that for electrical signal generation and monitoring, namely fewer optical sources and sensors optically switched among more numerous optical conductors.

FIG. 3B is intended to illustrate, not limit, the preferred DAQ board architecture. First, this architecture is easily scalable. Since microfluidic processors typically have numerous electrically driven heaters and electrical sensors many of which may operate in parallel, a DAQ board preferably has capability to simultaneously drive at least two heaters and to simultaneously sense at least two monitoring leads by, for example, having two or more analog switch/driver or analog switch/sensor pairs. Although simultaneous generation and monitoring of more than one optical signal is usually not required, this capability may be provided if necessary in the case of electrical signals. Second, DAQ boards may be based on other types of programmable devices and may have other arrangement of components for generating control signals and sensing monitoring signals that will be apparent to one of skill in the art in view of the above description. For example, the internal bus may be eliminated in favor of direct communication between the microprocessor and the signal generation/monitoring elements. Also, one or more switches may be eliminated in favor of an increased number of signal generation or sensing circuits. Finally, a single DAQ board may have receptacles and peripheral circuitry for controlling more than one microfluidic processor.

Software Architecture

Software instruction executed by microprocessor 43 (or other programmable control element) controls the DAQ board. In particular, responses to host messages and control signal generation are enabled according to the hierarchical microfluidic processor control functions. Although allocation of control system function among a host, a DAQ board, and a microfluidic processor is flexible, preferably, as described, the DAQ board performs most of the control functions in order that the microfluidic processor need provide only self-identification and in order that the user equipment need only provide an operator interface. Thereby, microfluidic processor cost is reduced, and the user equipment is freed from real-time microfluidic processor control.

A preferred software architecture is layered as is known in the art. At the lowest layer is an "operating system," which preferably provides, for example, standard software process control, communication, memory allocation, and access for control of DAQ-board peripheral circuitry. Software process and memory control preferably provides real-time, asynchronous control with interfaces for standard languages, such as C or C++. Drivers for peripheral circuitry preferably provide asynchronous control over the electrical and optical signals output to a microfluidic processor and asynchronous sensing of monitoring signals from a controlled processor. Such a system may be built, for example, from a minimal Linux kernel augmented with peripheral circuitry drivers.

In a software process-based method implementation, the operating system executes software processes managing, for example, microfluidic processor control functions, host communication, and internal DAQ board administrative functions. Host communication software processes preferably implement a layered communication protocols. At a network layer, communication is preferably packet based with error checking (for example, by a checksum with retransmission of lost or corrupt packets). At a physical layer, the protocol may be implemented over host communication link, such as the illustrated serial link from host interface 44, Ethernet, or so forth with provision for negotiation of transmission rates, packet sizes, and so forth. Exemplary protocols may be selected from the IP family, such as SLIP or TCP, or from other known protocols.

Internal administrative software processes provide responses to, for example, host requests for DAQ-board status, and for the operation and status of an attached microfluidic processor. Administrative software processes may also provide for DAQ-board software update. For example, in response to a host status request, the DAQ board should report its status (e.g., free, reaction in progress, steps completed, results now available, and so forth). The DAQ board may also perform diagnostic tests of the board itself and calibrate on-board sensor circuitry. In response to a power requirements request, the DAQ board should negotiate the power it expects to draw from the host in advance (e.g. for this particular reaction in this particular microfluidic processor). In response to a software update request, the DAQ board should request or accept software (or firmware) from the host. Further internal status requests and responses may also be provided for.

Microfluidic processor control software processes perform functions that have been generally described with respect to FIG. 2 above, and will be described in more detail below for the preferred thermally-controlled microfluidic processors. In a preferred embodiment, component-level, actuator-level, micro-droplet-level, and the user-provided reaction control function are performed by DAQ board software processes. Preferably, at least, functions for drop metering and mixing, temperature cycling, and separation of micro-droplet components in a separation media are performed on a DAQ board. In a software process-based embodiment, functions for the software control processes are hierarchically structured as are the function themselves. For example, an actuator software process sends request messages to its component-level software processes. Other control implementations will be apparent to those of skill in the art.

Methods and Functions

This sub-section describes control function for preferred thermally-controlled microfluidic processors, component-level functions, actuator-level functions, micro-droplet-level functions, and lastly user-level functions. This description is exemplary and not limiting. In view of the following description, one of skill in the art will understand how to construct other implementations of the described functions, and also how other possible components and actuators, which may constructed in the preferred thermally-controlled technologies, may be controlled according to this invention.

Temperature Control Functions

Temperature sensing and controlled heating are important component-level functions for preferred thermally-controlled microfluidic processors. Temperature sensor elements are preferably resistive elements (resistive temperature detectors or "RTDs") configured to have measurable resistance changes in response to temperature changes. Such a sensor may be made of platinum with resistance in the range of approximately 1000Ω (Ohm) to 4000Ω at 25° C., so that an accuracy and resolution of approximately 0.5° C. can be achieved with sensor circuitry capable of resistance measurements of approximately 0.25% or better accuracy and resolution.

Figure 4A:
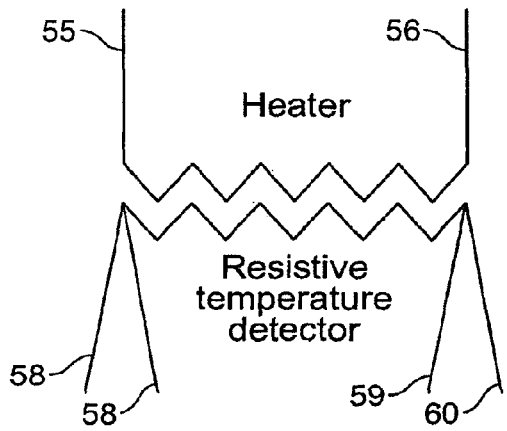
FIGS. 4A-C illustrate controlled heating component functions for a preferred microfluidic processor.
Figure 4B:
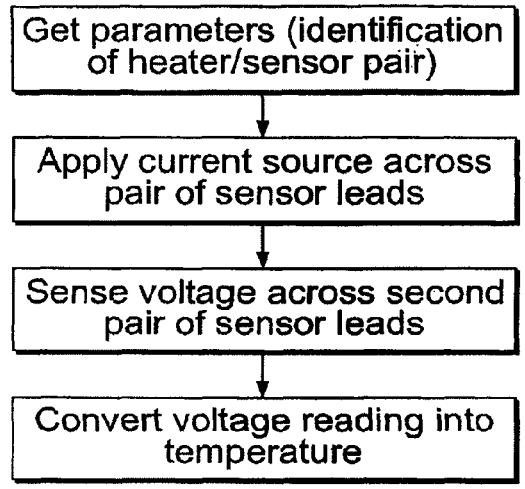

FIG. 4A illustrates an exemplary RTD, which can operate in at least two modes. FIG. 4B illustrates a function performing the first mode of temperature measurement. The function first obtains input parameters, here principally the identity of the particular RTD in question. RTD identity may be provided, for example, as an input to a procedural function invocation, or can be a local variable in an object representing this RTD, or by other means. However provided, this identity determines the control leads (and thus the DAQ-board connectors) to be used for measurement, for example, leads 57-60 in FIG. 4A, so that the DAQ-board microprocessor can control the appropriate peripheral circuitry. Next, a small current is applied across the RTD on one pair of leads, for example, leads 57 and 60, while the resulting voltage is sensed across a second pair of leads, for example, leads 58 and 59. Finally, the resistance of the RTD is determined from the supplied current and measured voltage (or vice versa), and the temperature is then converted from the measured resistance. The applied current is chosen small enough not to generate significant local heating, but large enough to generate a voltage drop measurable at the above precision. The use of two pairs of leads improves accuracy, because, since the voltage measurement can be made with little to no current, little or no voltage drop develops in measurement leads 58 and 59; most voltage drop measured being measured across the RTD itself. Alternatively, where less accuracy is sufficient, a single pair of leads can be used for current supply and voltage measurement.

In a second mode, the RTD can sense the presence or absence of a micro-droplet by measuring a local specific heat, which is greater when a micro-droplet is present in a nearby passage nearby than when no micro-droplet is present. This mode functions in a manner substantially similar to the first mode except that the applied current is greater and is applied for a time sufficient to generate enough heat to increase the surrounding temperature by a measurable amount, for example, by approximately, 2° to 4° C. in the absence of a micro-droplet. In the presence of a micro-droplet, the temperature increase will be less. Therefore, the presence or absence of a micro-droplet can be sensed by measuring the rate of the temperature increase.

Heaters are also preferably resistive and configured to controllably generate between 0.5 and 1.5 W of heat with a low voltage source. Since a preferred low source voltage is 5-10 V or less, the resistance of the resistive heaters in the range of approximately 15Ω to 1000Ω at 25° C. (even smaller heaters may be needed for source voltages of less than 5 V). As FIG. 4A illustrates, a heater with a nearby RTD may provide for controlled heating.

Figure 4C:
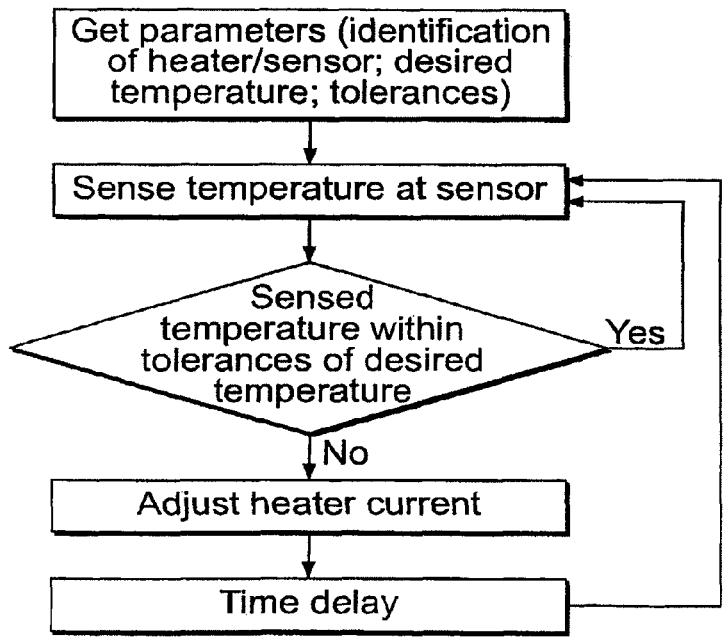

FIG. 4C illustrates a component-level controlled heating function. Input parameters include the identity of the heater/RTD pair, so that the microprocessor via the internal bus can energize or monitor the correct leads (and thus the correct DAQ-board connectors), and a desired temperature and temperature tolerance. Using a temperature sensing function, for example, the function illustrated in FIG. 4B, the temperature at the heater is determined. The heater current is then adjusted in view of the measured temperature, the desired temperature, and the tolerance. The time delay is chosen to provide for smooth control characteristics. These control steps, especially the current adjustment step, may also implement an alternative control method, such as a PID or a fuzzy logic method, that may depend on the currently measured temperature and on one or more temperatures measured in the recent past.

A further temperature-related, component-level function provides for controlling baseline device temperature. In addition to heaters, a preferred microfluidic processor may have a Peltier (or other) cooling device (or devices) in order to generally maintain the processor at a baseline temperature, for example, at a room temperature of 25° C. Alternatively, a Peltier cooler can be mounted on the DAQ board in a manner such that it makes thermal contract with a microfluidic processor when inserted into the board. Such a cooler prevents the progressive build-up of the effects of heaters energized during the course of a reaction or analysis. A cooling device may be controlled similarly to a resistive heater by adjusting a control current to maintain a specific temperature sensor at the desired baseline temperature, where the specific sensor is mounted at a thermal distance from heaters to sense background processor temperature.

Further Component-Level Functions

Figure 5A:
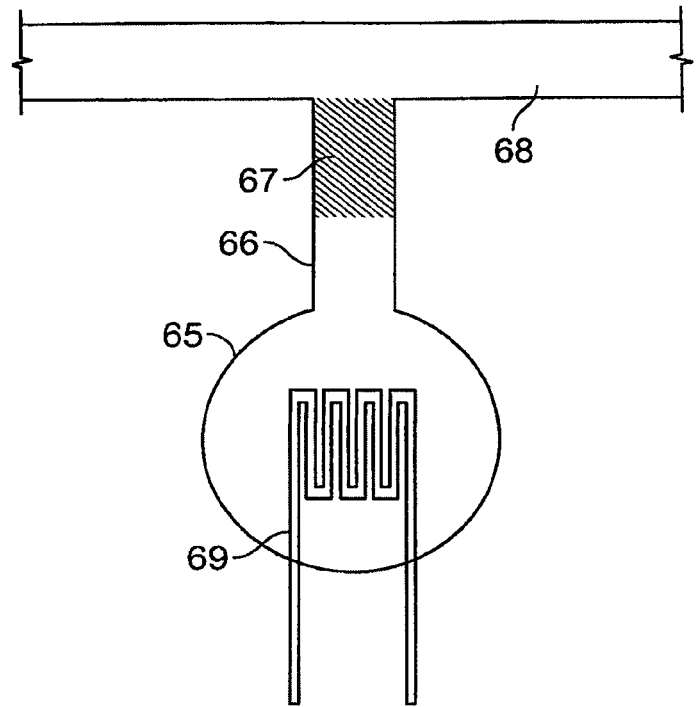
FIGS. 5A-B illustrate pressure generator component functions for a preferred microfluidic processor.

A further component-level function controllably generates pressure, for example, to move micro-droplets or other materials in a microfluidic processor. This function is an important component of several higher-level actuators requiring thermally-controlled mechanical force. A preferred embodiment of a pressure generator includes a gas reservoir with a controlled heating element and a passage conducting gas pressurized by heating to its point of application. FIG. 5A illustrates a preferred embodiment with relatively larger gas reservoir 65 and relatively smaller conducting passage 66 linking to the point of pressure application in passage 68. The gas in the reservoir is preferably inert, such a nitrogen or argon, but can be air. The reservoir has controlled heater 69 (the accompanying temperature sensor is not illustrated) embedded in its base (or top). Region 67 of passage 68 has a hydrophobic surface so that any (aqueous) fluid present in passage 68 is excluded from gas reservoir 69.

Figure 5B:
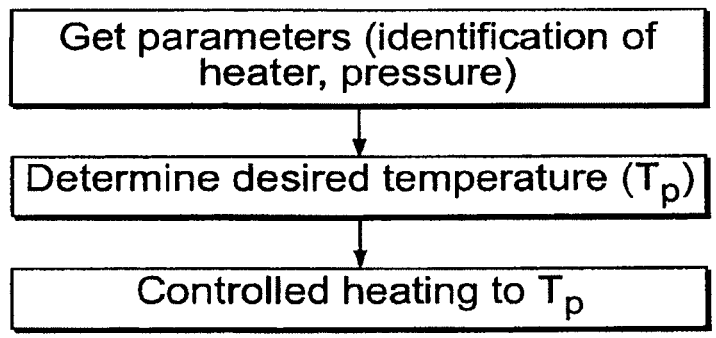

FIG. 5B illustrates a component-level control function for this pressure generator. In the first step, the function obtains identification of the pressure generator and its associated heater and a parameter representing the desired pressure to be generated. In a next step, the desired pressure is converted into a desired quantity of heat needed, and in the final step, the heater is controlled (by a control signal across connectors determined from component identity) to a temperature for a time sufficient to supply the needed heat.

In addition to micro-droplet sensors depending on temperature effects described previously, further component-level functions may control other types of micro-droplet sensors present on a microfluidic processor. For example, micro-droplet sensors may be based on capacitive detection, in which an impedance between two leads is altered by the presence or absence of a micro-droplet. The DAQ board then includes switchable impedance sensing circuits. Pressure sensors may also be present and can be used as micro-droplet position sensors as explained subsequently. Pressure sensors may also provide direct feedback for use in the controllable pressure function of FIGS. 5A-B.

Micro-Valve Function

Figure 6B:
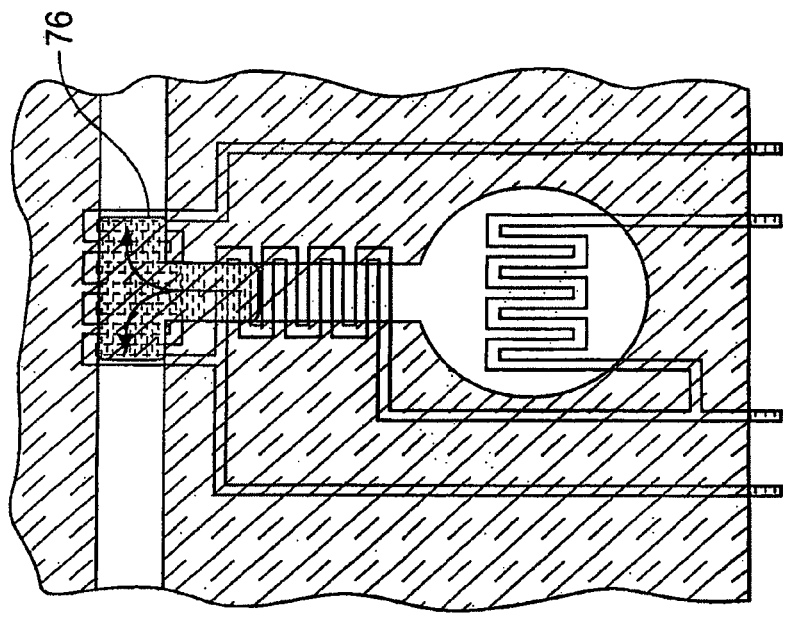
FIGS. 6A-D illustrate micro-valve actuator functions for a preferred microfluidic processor.
Figure 6A:
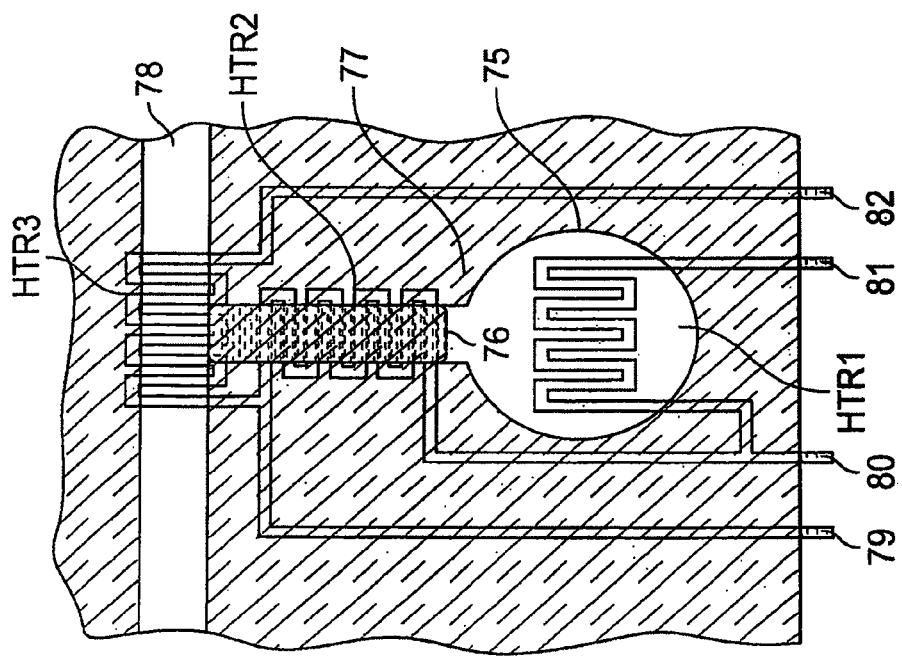

A micro-valves function is an important actuator-level function that will be present in most microfluidic processors. FIG. 6A illustrates a preferred embodiment of a micro-valve for closing and opening controlled passage 78. The micro-valve has a pressure generator, for example, including gas reservoir 75 with heater HTR1 and side passage 77 connecting with controlled passage 78. Side passage 77 is blocked by plug 76 of low melting-point, inert material. The melting point is preferably greater than the baseline operating temperature of the microfluidic processor but less than the boiling point of any micro-droplet controlled by this micro-valve in passage 78. For example, the melting point may be from 40° to 90° C., preferably from 50° to 70° C.; the material may be a wax (for example, an olefin) or a eutectic alloy (for example, a solder). The micro-valve also includes heater HTR2 for controlled heating of side passage 77, and heater HTR3 for controlled heating of controlled passage 78, as illustrated. Sensors optionally accompanying these three heaters are omitted from FIG. 6A for simplicity and without limitation.

The configuration of leads 79-82 is one arrangement that provides independent control of all three heaters with only four directly-routed and non-overlapping control leads. This illustrated arrangement is exemplary. For example, six leads, two for each heater, may be provided instead.

Figure 6C:
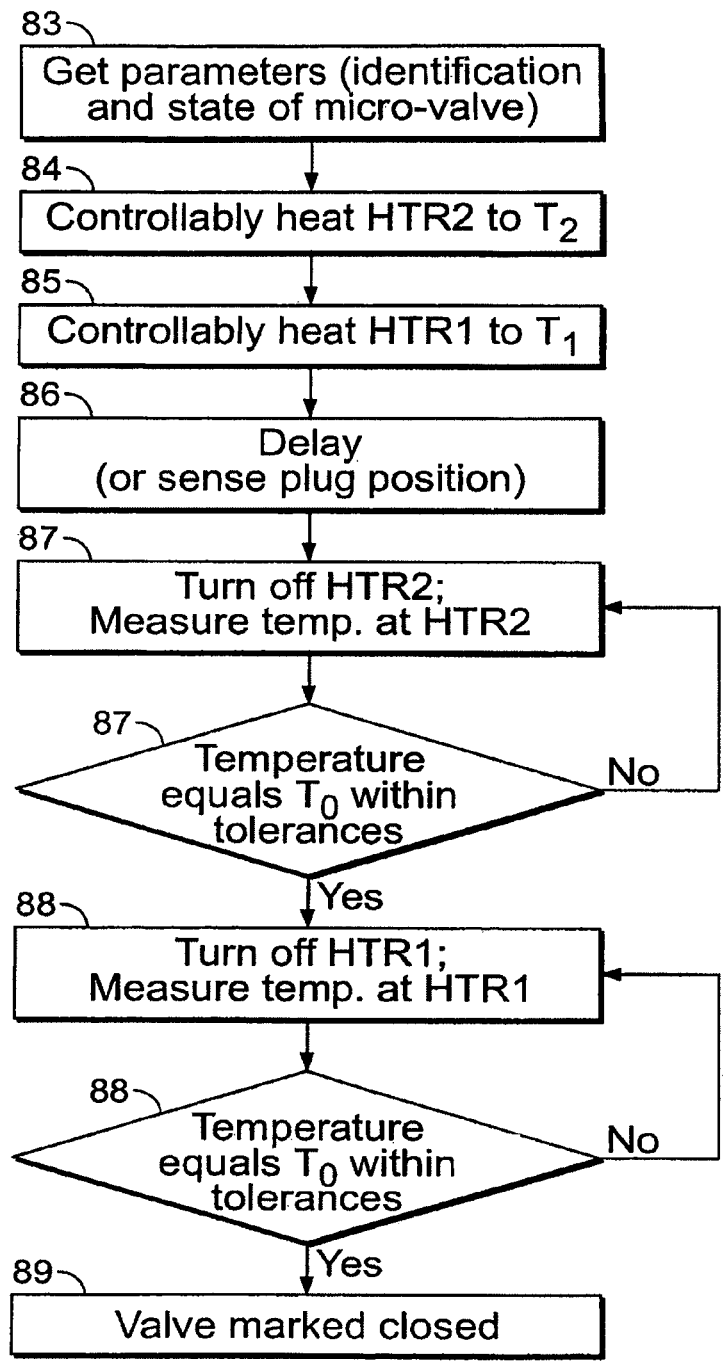

The micro-valve closing operation is described with reference to FIG. 6A, which depicts the micro-valve in an opened state, FIG. 6B, which depicts the micro-valve in a closed state, and FIG. 6C, which depicts the steps of the micro-valve close function. The close function first obtains input parameters 83, which identify the particular micro-valve to be closed, its component heaters, and the connectors for the heater control leads and for monitoring signals from any optional sensors. The input parameters also includes the current micro-valve state, which must be "open" for the micro-valve close function. (If the micro-valve is already closed, the close function may simply exit). Next, step 84 controllably heats HTR2 (by activating leads 79 and 80) and side passage 77 to a temperature $T_2$ slightly, but sufficiently, above (for example, no 5° C. above) the melting temperature of plug 76 so that the plug melts. After or simultaneous with plug melting, step 85 controllably heats HTR1 (by activating leads 80 and 81) to a temperature $T_1$ and for a time so the sufficient gas pressure is generated to move the melted plug from exit passage 77 into controlled passage 78. Preferably, $T_1 > T_2$. This pressure is maintained for a time delay 86 determined to be sufficient for the plug to move into passage 78. Alternatively, where a position sensor for the plug is available (for example, a thermal sensor in association with HTR3), the delay lasts until sufficient movement of the plug is sensed.

Step 87 then deactivates HTR2 and waits until its temperature returns within tolerances to $T_0$, the baseline processor temperature, so that the plug solidifies again. The return to baseline temperature may either be sensed by a sensor or may be assumed after sufficient time delay. After the plug is solidified, step 88 similarly returns the temperature of HTR1 and gas reservoir 75 to baseline. Because the volume of the gas is now greater because of the motion of the plug out of passage 77, a relatively lower gas pressure is present in reservoir 75 at the baseline temperature when the micro-valve is closed than when it is open.

The micro-valve is now closed because controlled passage 78 is blocked with the solidified plug. Step 89 marks the state of the micro-valve as closed in the data describing current microfluidic processor configuration.

Figure 6D:
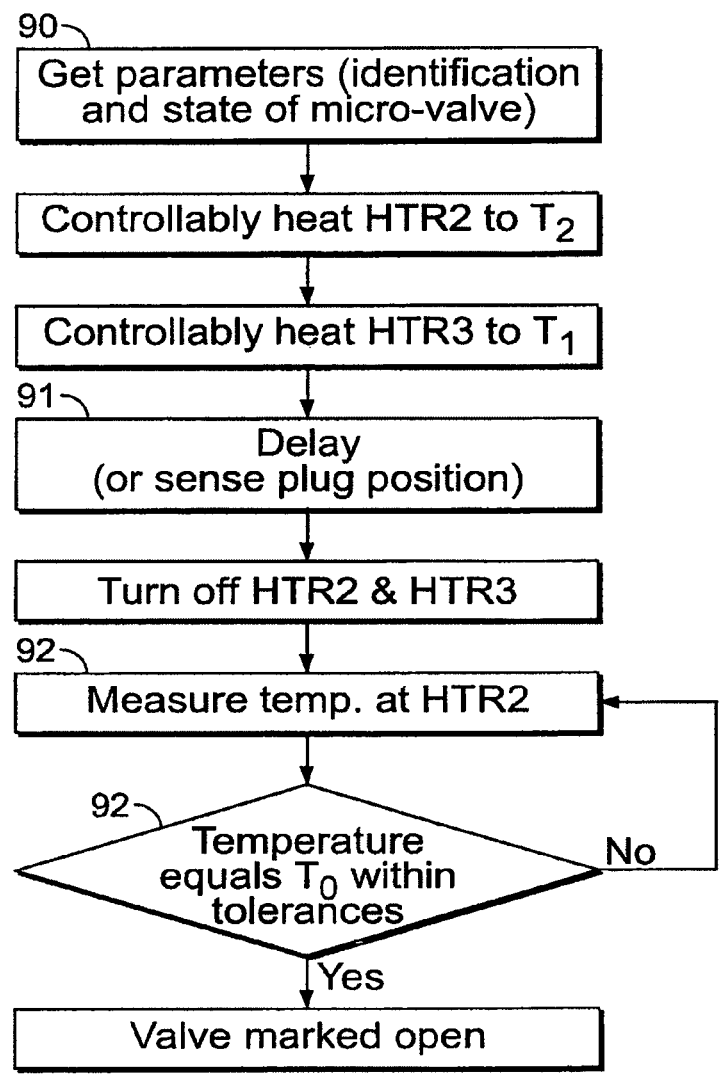

The micro-valve opening operation is described with reference to FIG. 6B, which depicts the micro-valve in a closed state, FIG. 6A, which depicts the micro-valve in an opened state, and FIG. 6D, which depicts the steps of the micro-valve open function. As customary, this function first obtains 90 input parameters. These parameters identify the control and monitoring connectors and indicate a closed stated (otherwise, the function simply exits). First, the function controllably heats HTR2 and side passage 77 to temperature $T_2$ and HTR3 and controlled passage 78 to temperature $T_1$. $T_1$ and $T_2$ are both above the melting point of the plug, as described above. Plug 76 in controlled passage 78 thereby melts, and, under the influence of the relatively lower pressure in gas reservoir 75 remaining from the micro-valve closing, is drawn back into side passage 77. These heaters are activated for a time delay 91 determined to be sufficient for the plug to move back into side passage 77. Alternatively, where a position sensor for the plug is available (for example, a thermal sensor in association with HTR2), the delay is until movement of the plug is sensed. Finally, heaters HTR2 and HTR3 are deactivated, and step 92 waits until the temperature in the vicinity of the exit passage heater has returned to within tolerances to baseline (either by temperature monitoring or by time delay). Finally, the micro-valve state is marked as closed with the plug now solidified in exit passage 77 and controlled passage 78 unblocked.

In the following descriptions, for ease of illustration and without limitation, micro-valves are schematically represented with a single heater and a single pair of leads, instead of their full illustration, as in FIGS. 6A-B, with three heaters and at least four leads.

Optical Detection Function

Optical sensing of the results of microfluidic processor reactions or analyses is preferred because it may be easily performed externally to a microfluidic-processor without any physical removal of reaction results from these passages. Alternatively, where a microfluidic processor includes a separation facility for reaction results, detection of components separated thereby is also preferably by optical means. Optical sensing may depend on scattered incident radiation or generated fluorescent radiation, or so forth. The invention also provides for the excitation of a reaction or analysis by radiation.

Basic optical detection components and control functions are illustrated with reference to FIGS. 11A-B. FIG. 11A illustrates limited section 165 of a microfluidic processor with exemplary components for optic sensing of micro-droplet md1, which is illustrated as stably positioned adjacent to hydrophobic region h1 of main passage 167. Optic components include radiation conductor 166 for conducting incident radiation (for example, from a DAQ-board laser diode) to md1, and radiation conductor 169 for conducting radiation from micro-droplet 1 for analysis (for example, to a DAQ-board photodiode). Radiation conducted from md1 may be scattered radiation, fluorescent radiation, or so forth. Lens 168 schematically illustrates elements for radiation gathering or focusing, filtering wavelengths, or so forth, present on the processor. Also, a reflector may be placed adjacent to the main passage to double the radiation path through the micro-droplet being sensed. Such a reflector may optionally have wavelength-dependent properties, being, for example, an interference filter or a dichroic mirror.

Limited portion 165 could be a substantially vertical depiction, illustrating substantially vertically arranged optic conductors out of the plane of the microfluidic processor and passing illumination through the thickness of the processor. This portion could also be a substantially horizontal depiction, illustrating substantially horizontally arranged optic conductors in the plane of the microfluidic processor and passing illumination through only one passage of the processor. Further, the optic conductors may run substantially in the plane of the processor (horizontally), only to angle to a final orientation near their target.

Figure 11B:
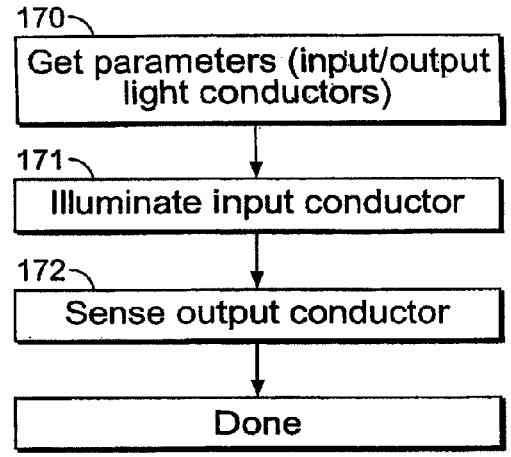
FIGS. 11A-B illustrate optic detection actuator functions for a preferred microfluidic processor.
Figure 11A:
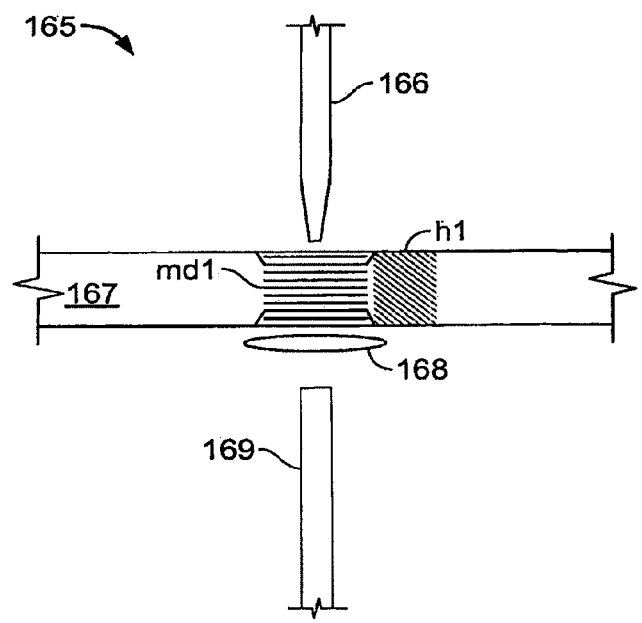

FIG. 11B illustrates an actuator-level, optical-sensing function. This function begins by obtaining parameters 170 that identity the particular optical-sensing actuator, so that the DAQ-board microprocessor may control those radiation generation and detection components that connect to the correct connectors for the identified detection optical sensor. Next, the input radiation conductor is illuminated 171, and the resulting radiation is sensed 172.

Other such entirely external detection methods, based on exteriorly-applied magnetic (NMR) or electric fields, or on a combination of these fields with optical detection, can also be preferably used in the microfluidic processors of this invention. In this case, field generation components must be placed on a microfluidic processor or on the DAQ board (or on a DAQ-board housing), must be identified to the control function, and must be activated by the control function.

Micro-Droplet Move Function

A micro-droplet move function is an important configuration-level function that will be present in most microfluidic processors. This function moves a micro-droplet from a first position to a second position, thereby advancing the microfluidic processor from a first configuration to a second configuration in which the micro-droplet moved is in its second position. This, and other micro-droplet-level functions, act most reliably when the initial and final micro-droplet positions are stable. They are preferably only invoked or only act when the data describing the current processor configuration indicates that micro-droplets are corrected positioned at a stable position. As described, a stable position can be established by, for example, a hydrophobic region in a passage, or by a local configuration of passages.

Micro-droplet motion of course requires thermally-controlled mechanical force and generally, in preferred microfluidic processors, this mechanical force is gas pressure-generated by a pressure generator actuator. Micro-droplet motion may be stopped when the motion pressure is dissipated by, for example, a vent to the processor exterior. Motion may also be stopped by a hydrophobic region which requires more motive force than is being supplied (coupled with deactivating the pressure generator actuator).

Figure 7B:
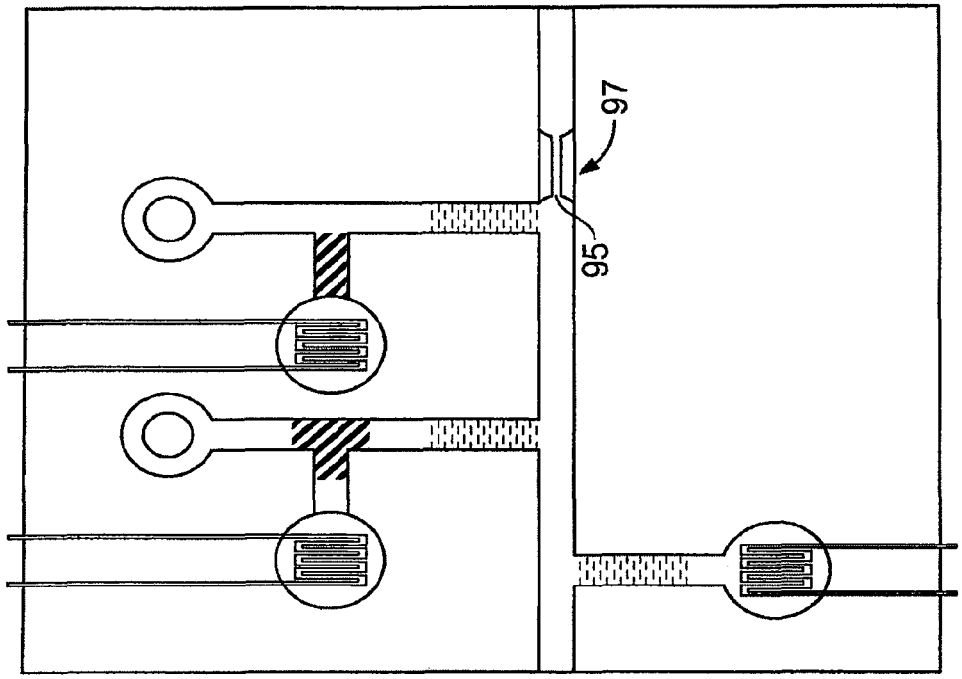
FIGS. 7A-C illustrate micro-droplet motion functions for a preferred microfluidic processor.
Figure 7A:
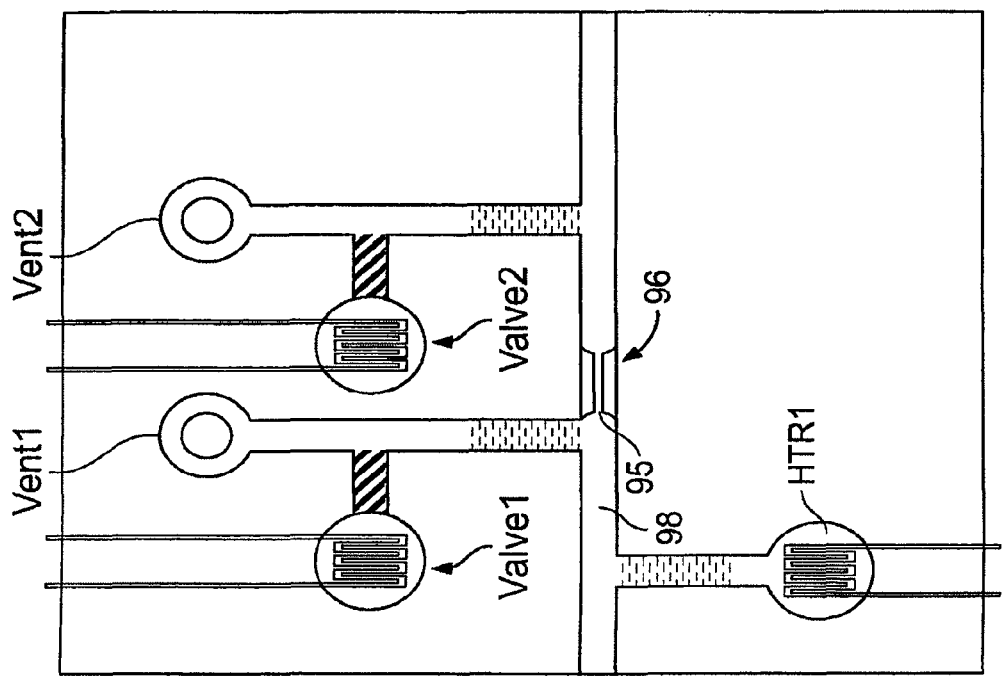
Figure 7C:
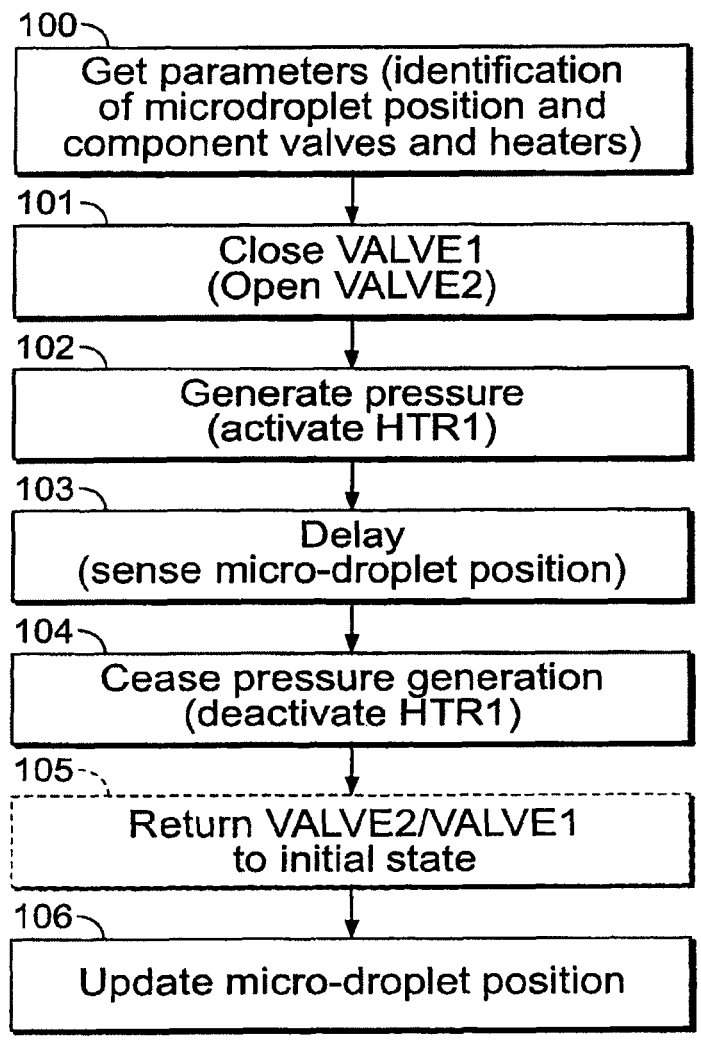

Micro-droplet motion is illustrated with reference to FIG. 7A, depicting micro-droplet 95 in initial position 96, FIG. 7B, depicting micro-droplet 95 in final position 97, and to FIG. 7C, depicting the steps of the micro-droplet-motion function. Micro-valves in these figures (and subsequently) are schematically represented with only a single heater. Step 100 of the move function customarily obtains parameters identifying the components of the sub-assembly for moving micro-droplet 95, here, valve1, valve2, and HTR1, their spatial relationship, and their control leads or external connectors. In the exemplary configuration illustrated, initial micro-droplet position 96 is just beyond the side passage to vent1, a stable position after a prior movement with valve1 open, leaving vent1 accessible from main passage 98 to dissipate any driving pressure. Alternatively (not illustrated), the initial stable position may be defined by a hydrophobic region in passage 98, and valve1, vent1, and their connecting side passage may be absent from the microfluidic processor. Micro-droplet 95 is determined from the input configuration data to be correctly in an initial stable position 96, because the known, current, microfluidic-processor configuration records the position of all micro-droplets present in the processor. If there is no micro-droplet at position 96, there is nothing for this function to do, and it exits. Preferably, the present motion function is called by a higher-level function only when micro-droplet 95 is in position 96 as a result of prior functions.

Next, step 101 prepares the micro-valves for micro-droplet motion by invoking the actuator-level micro-valve functions to close valve1 (if present and previously open, as determined by its state in the microfluidic processor configuration data) and to open valve2 (if previously closed, as also determined by its state). Step 102 then generates a pre-determined pressure by invoking actuator-level pressure-generation functions 102. The generated pressure moves the micro-droplet to the right (it being assumed that generated pressure is not dissipated to the left in passage 98 and that passage 98 is "open" to the right of position 97), until final position 97 where the applied pressure dissipates to the exterior through vent2. The micro-droplet itself is prevented from entering vent2 by the hydrophobic protection of its connecting side passage. When the micro-droplet reaches its final position, after delay 103, step 104 halts the pressure generation functions by deactivating HTR1. The duration of active pressure generation may be determined as a pre-selected time interval, optionally dependent on the processor configuration. Alternatively, where a micro-droplet position sensor is available (for example, a thermal-type sensor or a capacitive-type sensor), step 103 may wait until the micro-droplet is sensed to be in the final position. Optional step 105 invokes the micro-valve functions to return valve1 and valve2 to their states before micro-droplet motion.

Finally, upon successful completion, the micro-droplet position in the microfluidic-processor configuration data is then updated in step 106.

Micro-Droplet Metering Function

The configuration-level micro-droplet metering function creates a new micro-droplet of a more precisely known and smaller volume of fluid from a usually less precisely known and larger fluid volume (a reactant, a sample, or so forth) introduced into a microfluidic processor.

Figure 8B:
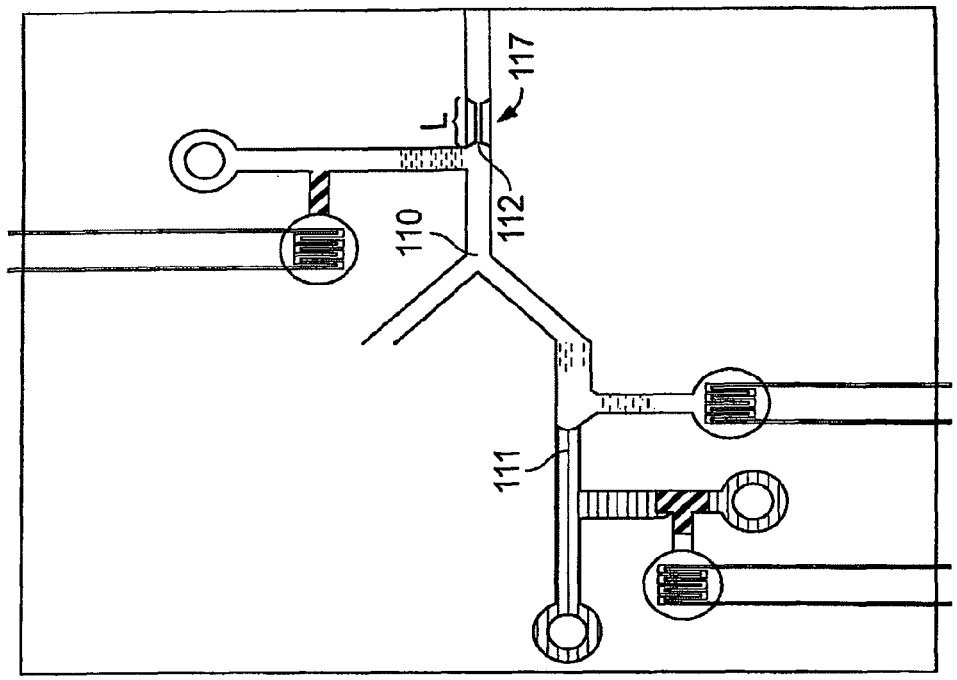
FIGS. 8A-D illustrate micro-droplet metering functions for a preferred microfluidic processor.
Figure 8A:
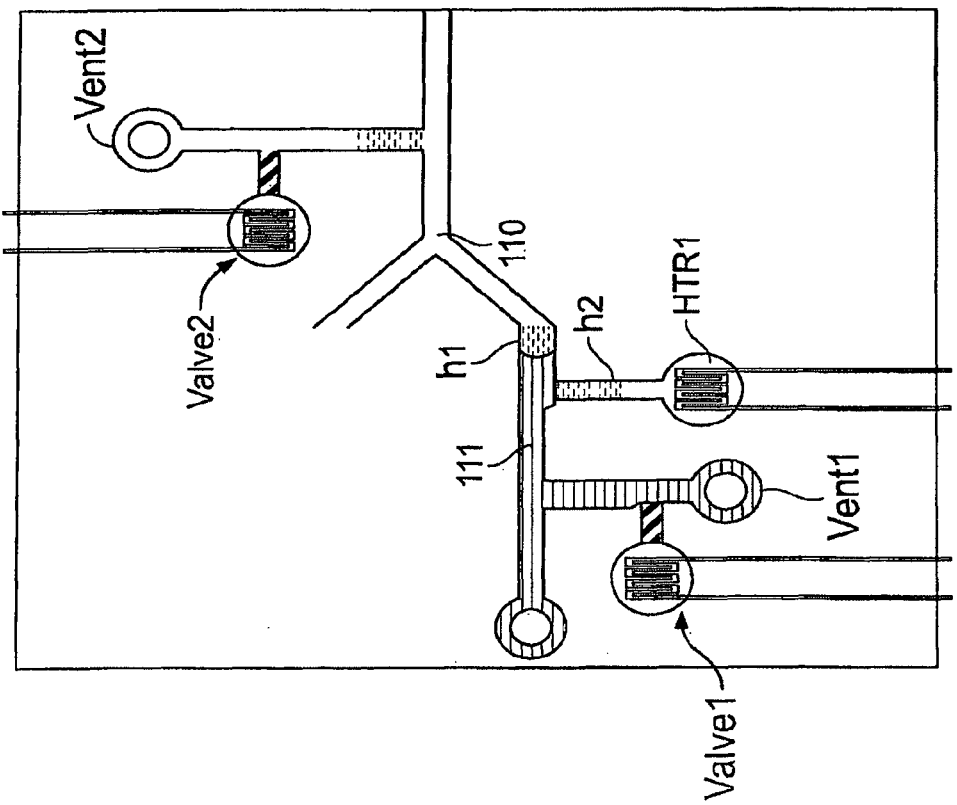
Figure 8C:
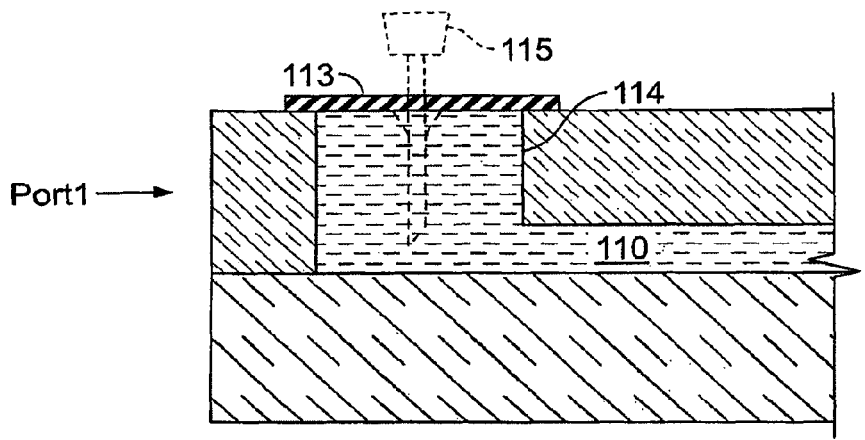

Fluids may be introduced into a processor through ports by manual transfer means (for example, a pipette) or by automatic transfer means (for example, a robot) from an exterior source. Ports may be provided on the microfluidic processor to accept various fluid transfer means, for example syringes or pipettes. FIG. 8C illustrates an exemplary port adapted for syringes. Port1 includes fluid reservoir 114, covered with puncturable membrane 113 (for example, of a self-sealing, rubber-like material), and connected to passage 110 in a microfluidic processor. This figure illustrates syringe 115 having punctured membrane 113 and already having introduced fluid into the port. The membrane insures injected fluid penetrates into the processor without back flow. In the case of pipettes, the shape of reservoir 114 may be adapted to a sealed fit with the pipette tip for fluid transfer.

In a preferred embodiment, a new micro-droplet is metered by being pinched off from the larger volume, generally by means of a gas pressure force. Micro-droplet metering is illustrated with reference to FIG. 8A, which shows an initial configuration before metering, FIG. 8B, which shows a final configuration with new, metered micro-droplet 112, and to FIG. 8C, which shows steps of the preferred metering control function. FIG. 8A illustrates fluid aliquot 111, having been introduced through port1 (such as the port illustrated in FIG. 8C) filling passage 110 up to the stable position formed by hydrophobic region h1. Hydrophobic region h2 prevents fluid entry into the side passage to HTR1. Excess fluid may escape through vent1, since valve1 is initially open, and excess gas may escape though vent2, since valve2 is initially open. Passage 110 is designed, i.e., by having the illustrated relative sizes, so that fluid aliquot 111 experiences greater capillary force there than in the side passage to vent1, in order that the fluid aliquot extends to the hydrophobic patch before excess liquid extends to vent1. This configuration of passage sizes further stabilizes the stable position formed by hydrophobic region h1.

The metering operation begins, as usual, at step 120, which identifies the metering components, their states, their arrangement, order, and their signal lines or external connectors. Optional step 121 opens valve1 and valve2 by means of the actuator-level micro-valve functions, if they were not initially open. Next, the metering function waits 122 for the loading of the fluid aliquot from which a micro-droplet is to be metered. Its loading may be indicated by an external manual signal provided to the user equipment (and transmitted to the DAQ board), or may be automatically indicated by completion of robotic loading, or may be provided by an internal sensor can detect the presence of fluid adjacent to hydrophobic region h1 of passage 110. Step 123 then closes valve1 by invoking the micro-valve close function, so that no more fluid may escape out of vent1.

Step 124 generates pressure by invoking the actuator-level pressure generator function (which activates HTR1). The pressure generator is controlled to a pre-determined pressure (if pressure sensors are available) or, alternatively, to a pre-determined metering temperature The resulting gas pressure pinches a length L of aliquot 111 that lies between the exit of the side passage to the pressure generator and the end of the aliquot at the stable position, forming a new micro-droplet. The volume of the metered micro-droplet is determined by length L and the cross-section of passage 110. With reference now to FIG. 8B, the generated pressure further acts to move new micro-droplet 112, in the manner of the micro-droplet motion function described above, to position 117, which is just beyond a side passage to vent2. The generated pressures dissipates out vent2 since valve2 is open. Steps 125 and 126 cease pressure generation after a pre-determined delay, or alternatively after micro-droplet 112 is sensed to be in position 117 (by a micro-droplet position sensor). Finally, an optional step closes valve2, to prevent further gas escape, thereby keeping the new micro-droplet from rejoining fluid aliquot 111. Valve1 may returned to its initial state.

Lastly, step 127 updates the microfluidic processor configuration to reflect the presence, location, and composition (the same as aliquot 111) of the new micro-droplet.

Micro-Droplet Mixing Function

Effective mixing of inhomogeneous micro-droplets is useful because simple diffusion, especially of biological macro-molecules, is often too slow to be practicable, even for adjacent micro-droplets in physical contact. Generally, micro-droplet mixing is achieved by motion that is sufficiently rapid, in view of the passage size and droplet viscosity, to induce micro-droplet mixing. Preferably, the micro-droplet velocity equals or exceeds the critical inter-layering velocity. In a preferred embodiment, a micro-droplet-level mixing function may invoke a micro-droplet-level motion function in such a manner that the motion is sufficiently rapid. This may be achieved by activating the pressure generator actuator, which provides the mechanical force to move the micro-droplet, so that the generated pressure rises sufficiently rapidly to a sufficiently high level to cause rapid motion. Appropriate activation of the pressure generator heater so that mixing of micro-droplets of particular viscosities occurs in passages of various sizes can be readily be determined experimentally and stored for use by the mixing function.

Figure 9A:
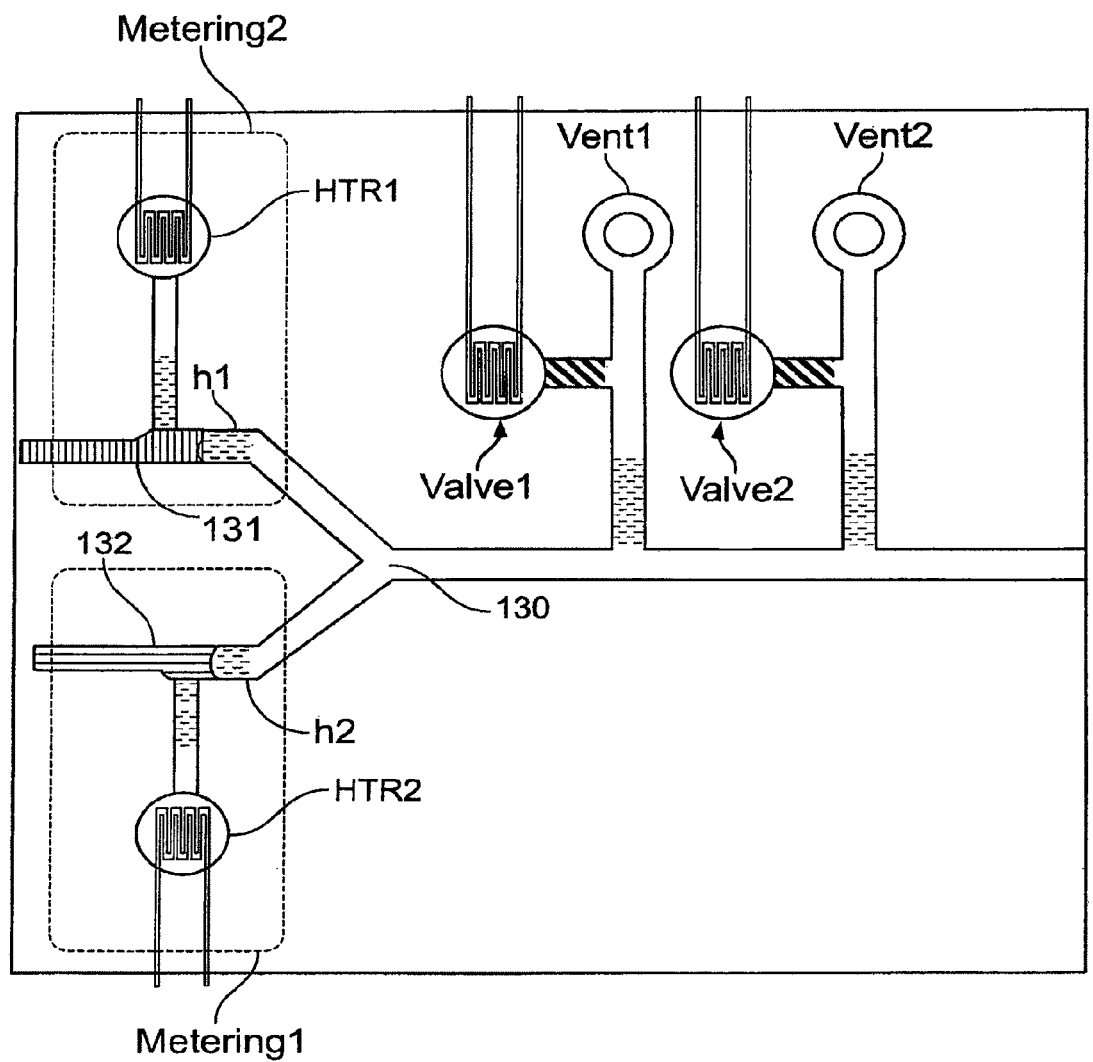
FIGS. 9A-E illustrate micro-droplet mixing functions for a preferred microfluidic processor.
Figure 9B:
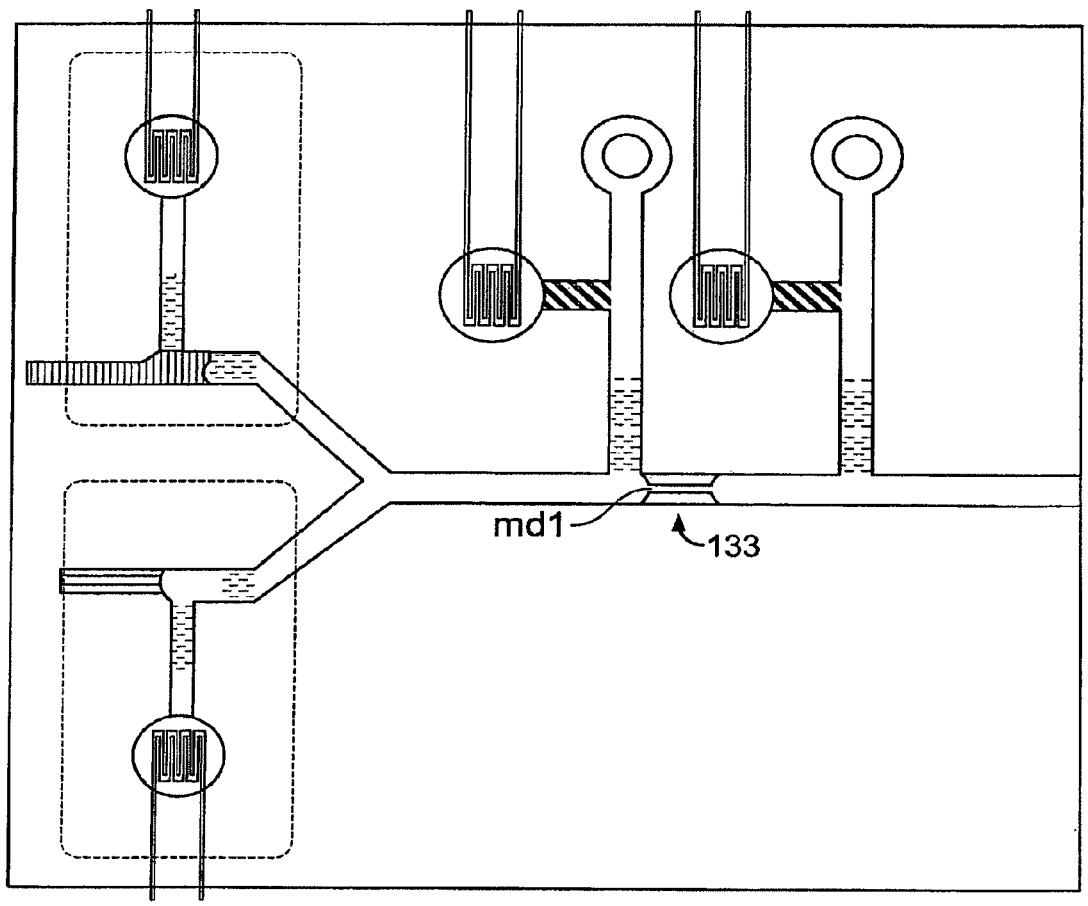
Figure 9C:
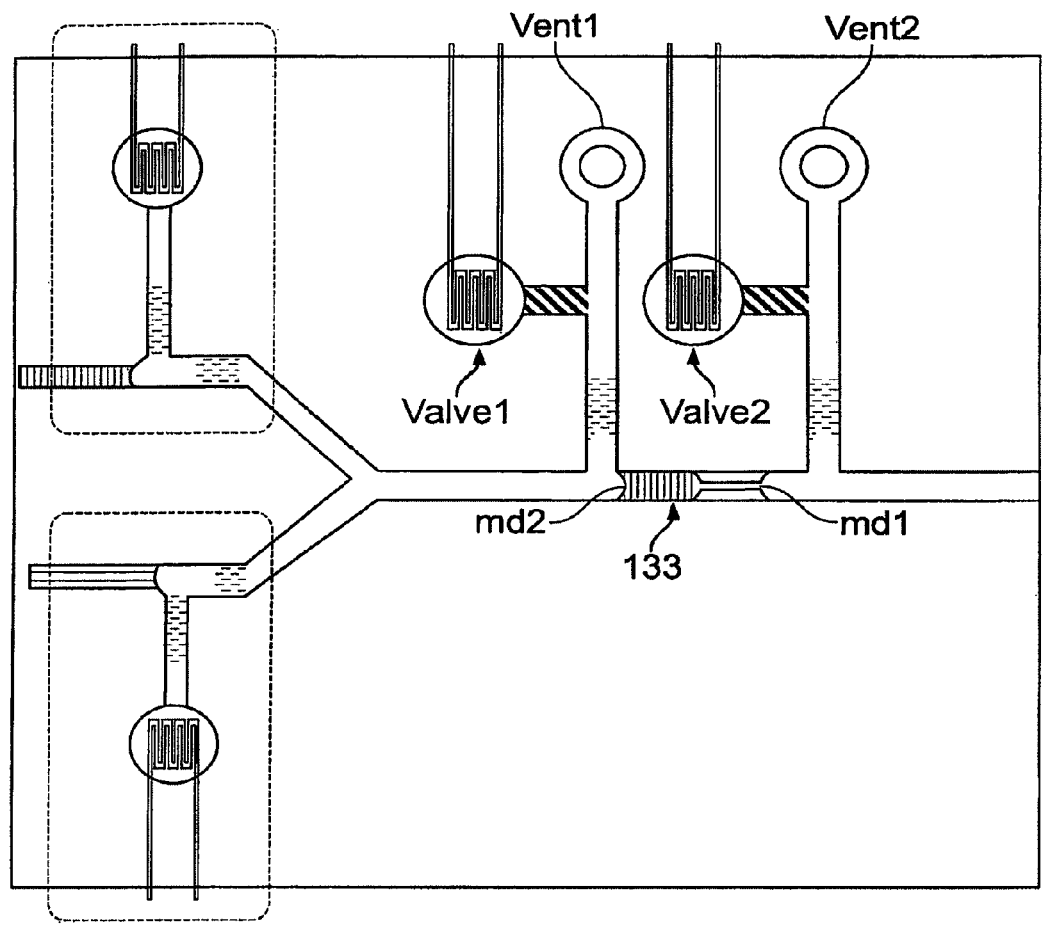

Inhomogeneous micro-droplets requiring mixing may arise for various reasons. For example, FIGS. 9A-C illustrate formation of an inhomogeneous micro-droplet as a result of metering two different fluid aliquots into two adjacent micro-droplets. FIG. 9A illustrates portions of two metering assemblies, metering1 and metering2, after loading aliquot 131 of a first fluid and aliquot 132 of a second fluid, but prior to micro-droplet metering. (FIGS. 8A-B illustrate such metering assemblies in full.) Pressure generator heaters, HTR1 and HTR2, are parts of these two metering assemblies. FIG. 9B next illustrates micro-droplet, md1, in position 133 after it has been metered from aliquot 131. Next, FIG. 9C illustrates md2 in position 133 after it in turn has been metered from aliquot 132. Md2 is positioned adjacent to md1, and these two micro-droplets now form, in effect, a single inhomogeneous micro-droplet.

Figure 9D:
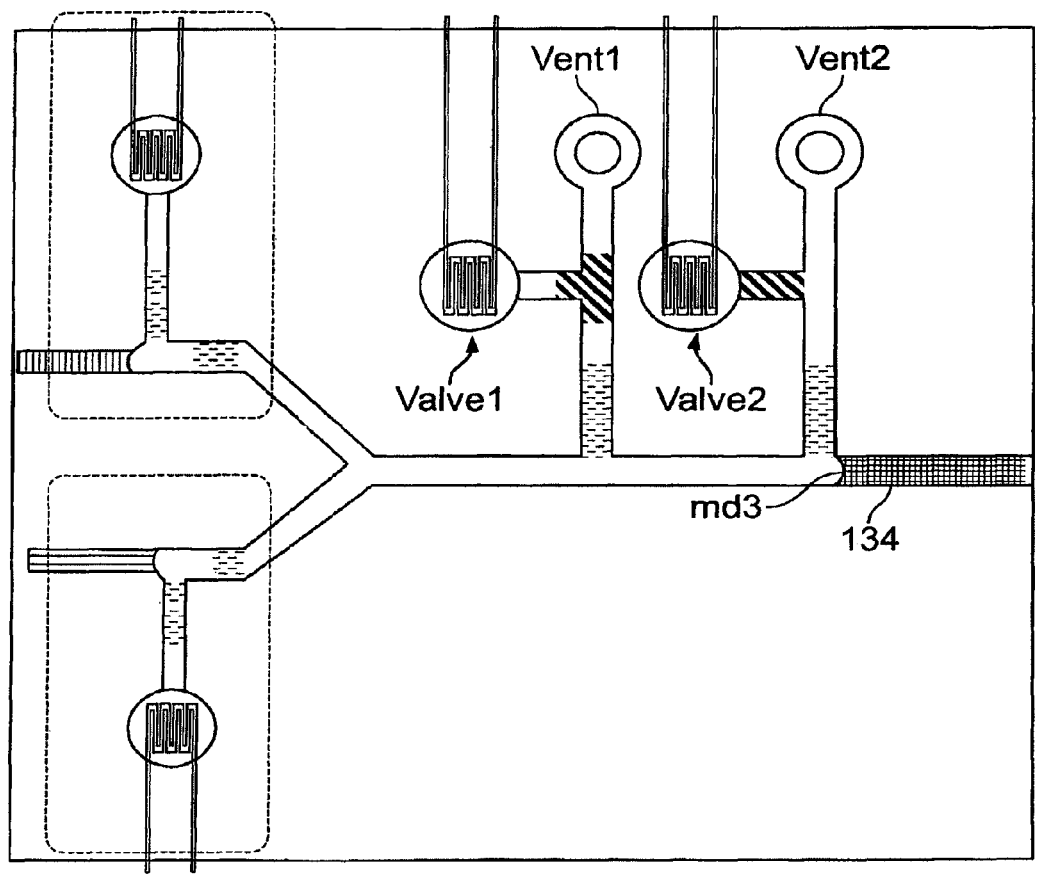
Figure 9E:
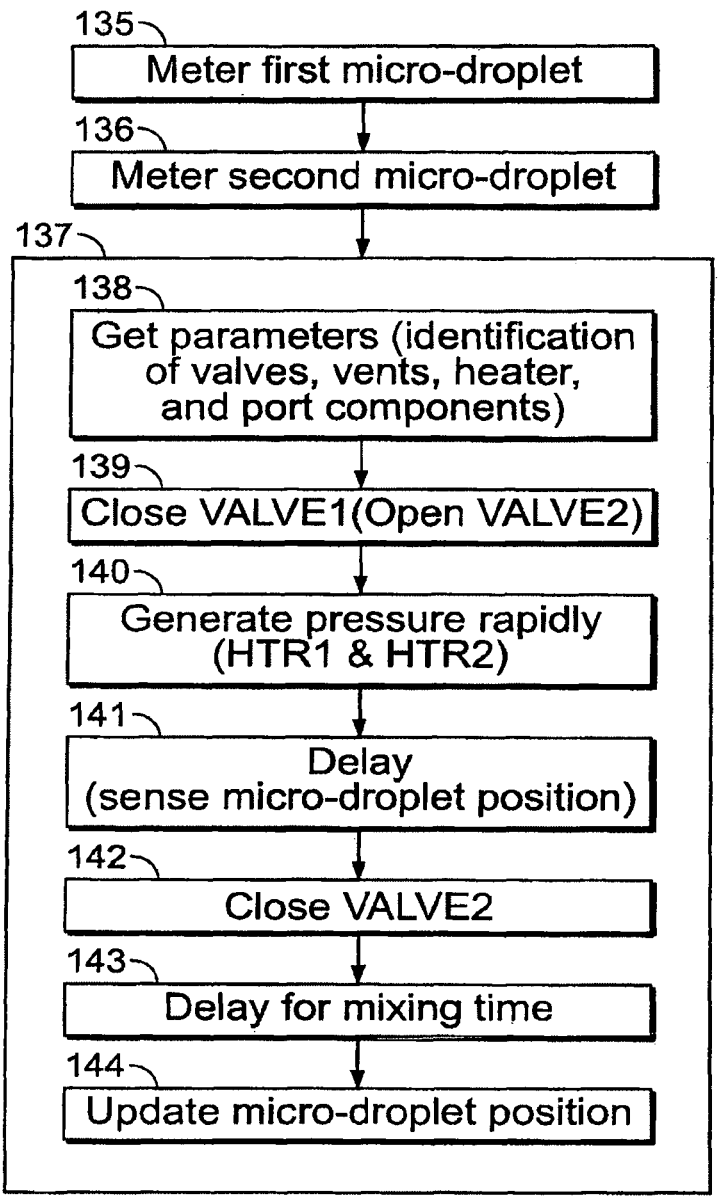

The mixing function is now described with reference to FIG. 9C, which depicts the configuration prior to mixing, FIG. 9D, which depicts the configuration after results of mixing, and FIG. 9E. This latter figure depicts the described preliminary metering steps 135 and 136 which prepare an inhomogeneous micro-droplet for mixing, as well as steps 137 of the actual mixing function. Step 138, as customary, obtains necessary input parameters, including identification of the mixing assembly components (here, portions of the two metering assemblies) and their control leads, and positions of the micro-droplet to be mixed. In this case, pressure for micro-droplet mixing may be generated by either or both of the pressure generators present in the metering components. Step 139 invokes actuator-level micro-valve functions to close valve1 (which is usually open as a result of the previous metering steps), and to open valve2, if necessary. Next, step 140 invokes the actuator-level pressure generation function to rapidly generate pressure, using either or both of HTR1 and HTR2 heated to a sufficient temperature (the mixing temperature) to cause mixing of the micro-droplet. Step 141 delays until (or senses when) micro-droplet md3 has reached position 134, then step 142 closes valve2 behind the md3.

Lastly, step 144 updates the microfluidic processor configuration data to reflect the location and composition (now mixed) of the new micro-droplet.

Perform Reaction Function

Generally, a micro-droplet that has been created with the correct composition is ready for the intended reaction or analysis. Preferably, for reaction, this micro-droplet is then isolated in order to avoid evaporation or unintended interactions with the remainder of the microfluidic processor, and adjusted to a determined temperature, in order that the reaction proceeds as intended. Certain reactions, notably the polymerase chain reaction (PCR), may require that the micro-droplet be repeatedly cycled through a determined temperature protocol. Other reactions may require a (solid) catalyst, which will need to be in the reaction region of the microfluidic processor. Further, reactions may require radiation stimulation. Although the following description is, without limitation, in terms of reactions at a determined temperature, one of average skill in terms of the following description will readily understand how to provide for temperature protocols, catalysis, radiation stimulation and so forth.

Figure 10A:
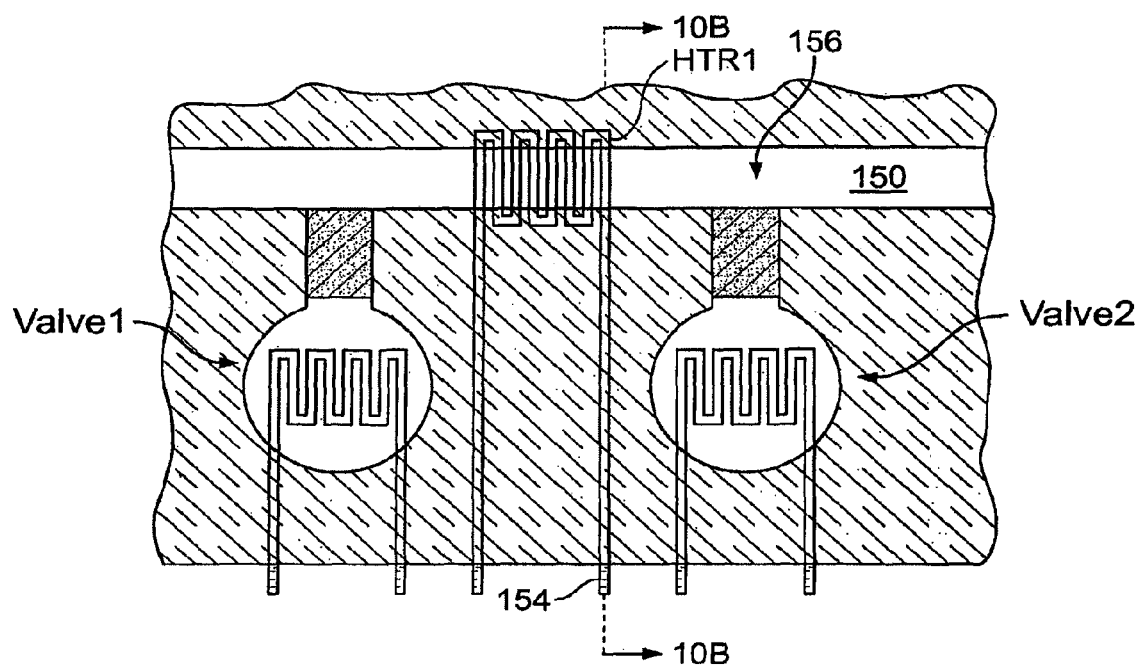
FIGS. 10A-E illustrate reaction/analysis functions for a preferred microfluidic processor.

Therefore, in the preferred embodiment described, reactions are performed in a controllably-heated region of a passage that may be isolated from the rest of the microfluidic processor, or in a controllably-heated reservoir into which a micro-droplet can be moved and isolated. FIG. 10A illustrates exemplary reaction region 156 (without any catalyst) in passage 150, having a controllable heater, HTR1, and isolating valves, valve1 and valve2. Region 156 is a stable position for a micro-droplet because of, for example, side passage 151 leading to a controllable vent. (Similar stable positions are discussed with respect to, inter alia, FIG. 1.) Alternately, a suitably placed hydrophobic region may define this stable position.

Figure 10B:
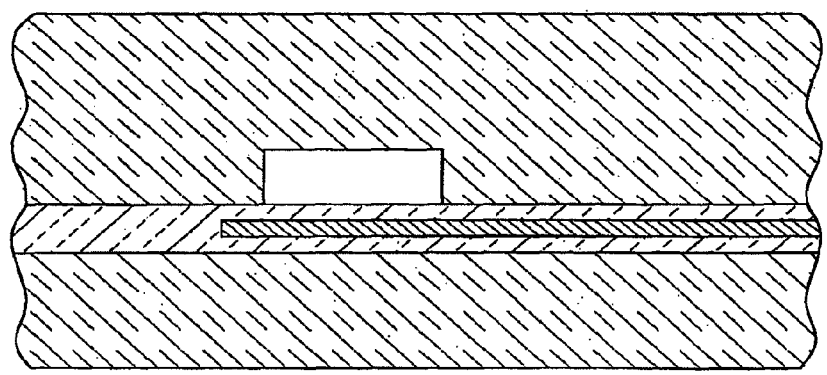
Figure 10C:
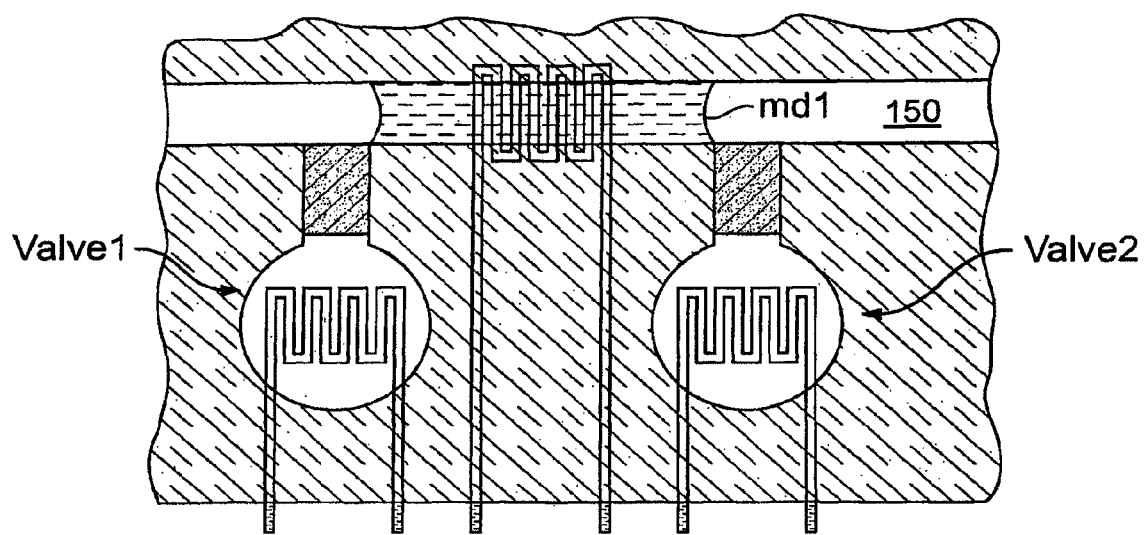
Figure 10D:
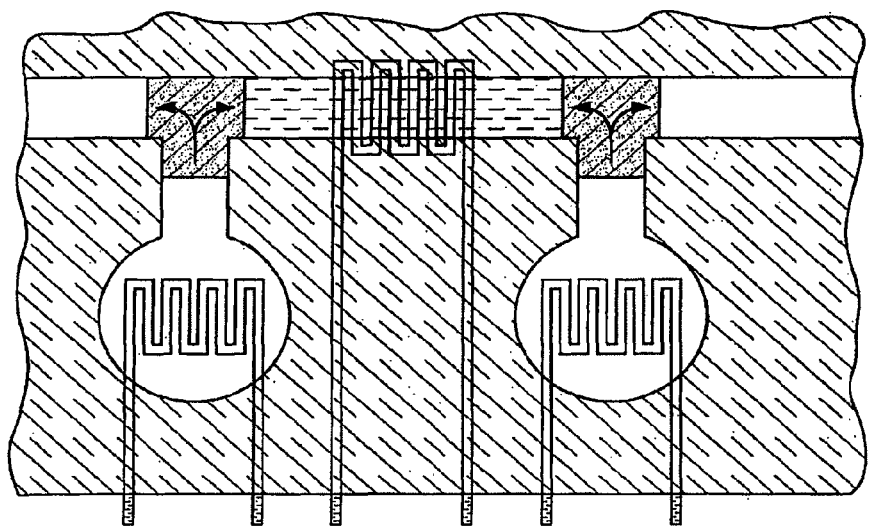
Figure 10E:
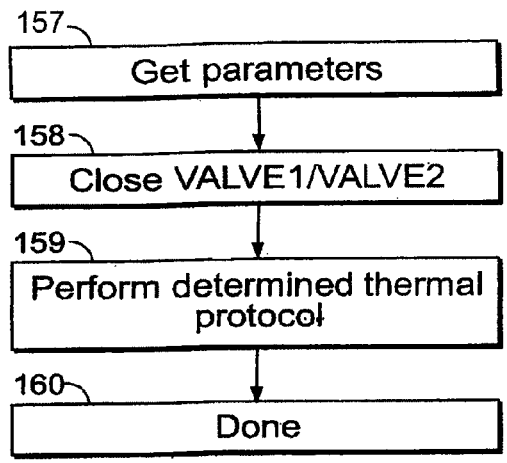

A reaction control function is illustrated with respect to FIG. 10C, which depicts reaction region 156 before reaction, to FIG. 10D, which depicts reaction region in the course of the reaction, and to FIG. 10E, which depicts the steps of a reaction control function. Step 157 obtains parameters including microfluidic processor configuration, the temperature profile for the reaction, the identities of the components forming the reaction region and their control leads and connectors. From the obtained configuration, this function checks that a micro-droplet having the correct composition is positioned in the reaction region as a result or prior microfluidic processing steps. If not, this function exits, perhaps with an error indication. Next, step 158 invokes the actuator-level micro-valve functions to isolate reaction region 156 by closing valve1 and valve2 . Step 159 performs the prescribed thermal protocol. Since no micro-droplet positions are changed by this function, the configuration need be updated only to the extent of indicating that a reaction has been performed.

This reaction completed may be the final result of the microfluidic processing, in which case the contents of the resulting micro-droplet are sensed, or it may be an intermediary reaction, in which case the resulting micro-droplet is further processed.

Next, exemplary construction of preferred, thermally-controlled microfluidic processors is briefly described. For example, FIG. 10B illustrates a section of FIG. 10A along line 10A-10B depicting general construction of such processors from top plate 152, and parallel bottom plate 155, which is positioned and bonded with a seal against the top plate. The plates may be silicon, plastic polymer, glass or so forth. Passages, such as passage 150, are machined, etched, pressed, or otherwise defined in one plate, here the top plate, while the bottom plate is substantially flat, and have walls appropriately treated for the type of micro-droplets to be processed. In particular, hydrophobic (or hydrophilic) passage regions are defined by passage treatments before plate bonding. Electrical components and leads, such as lead 154, are deposited preferably on the non-etched, substantially flat plate, and are covered (also, underlain if necessary) by insulating layer 153, which is inert to contents of the passages. Leads may be vapor deposited metal, for example, aluminum. Insulating layer may be a ceramic or polymer, for example, silicon dioxide. Light conductors may be made from optic fibers attached to a processor after plate bonding. Construction methods are adapted from those well known in the lithographic arts used in semiconductor fabrication. See, for example, U.S. Pat. Nos. 6,048,734, 6,057,149, and 6,130,098.

Integrated Device Operation Functions

The previously described micro-droplet-level functions can be combined to create user-level reaction-control functions for many different types of microfluidic processors performing many different reactions or analyses. Construction, or programming, of such control functions according to the present invention is enormously simplified because attention need generally only be paid to intuitive micro-droplet-level functions, which specify laboratory functions familiar to chemists and biologists, such as metering, moving, mixing, or reacting. Details of individual microfluidic-processor components and of their sequential control are hidden by the hierarchical construction of the component-level, actuator-level, and micro-droplet-level control functions, all of which function cooperatively to perform necessary low-level microfluidic processor control. This hierarchical control is possible because of the digital nature of the controlled microfluidic processors.

These advantages are illustrated by a user-level reaction-control function for the preferred thermally-controlled microfluidic processor illustrated in FIG. 1. This processor is capable of performing, inter alia, a simple PCR analysis of sample by metering a first micro-droplet containing the sample and some PCR reagents, by metering a second micro-droplet containing remaining PCR reagents, by mixing the two micro-droplets, by performing a PCR temperature protocol on the mixed micro-droplet, and by detecting the reaction results.

Figure 8D:
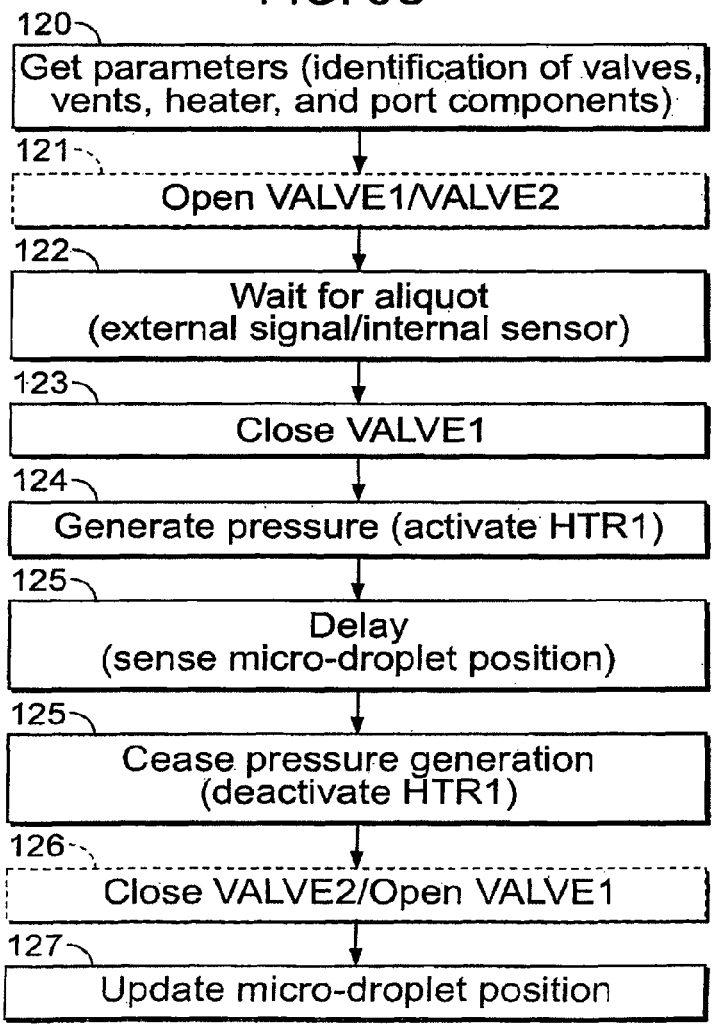
Figure 12:
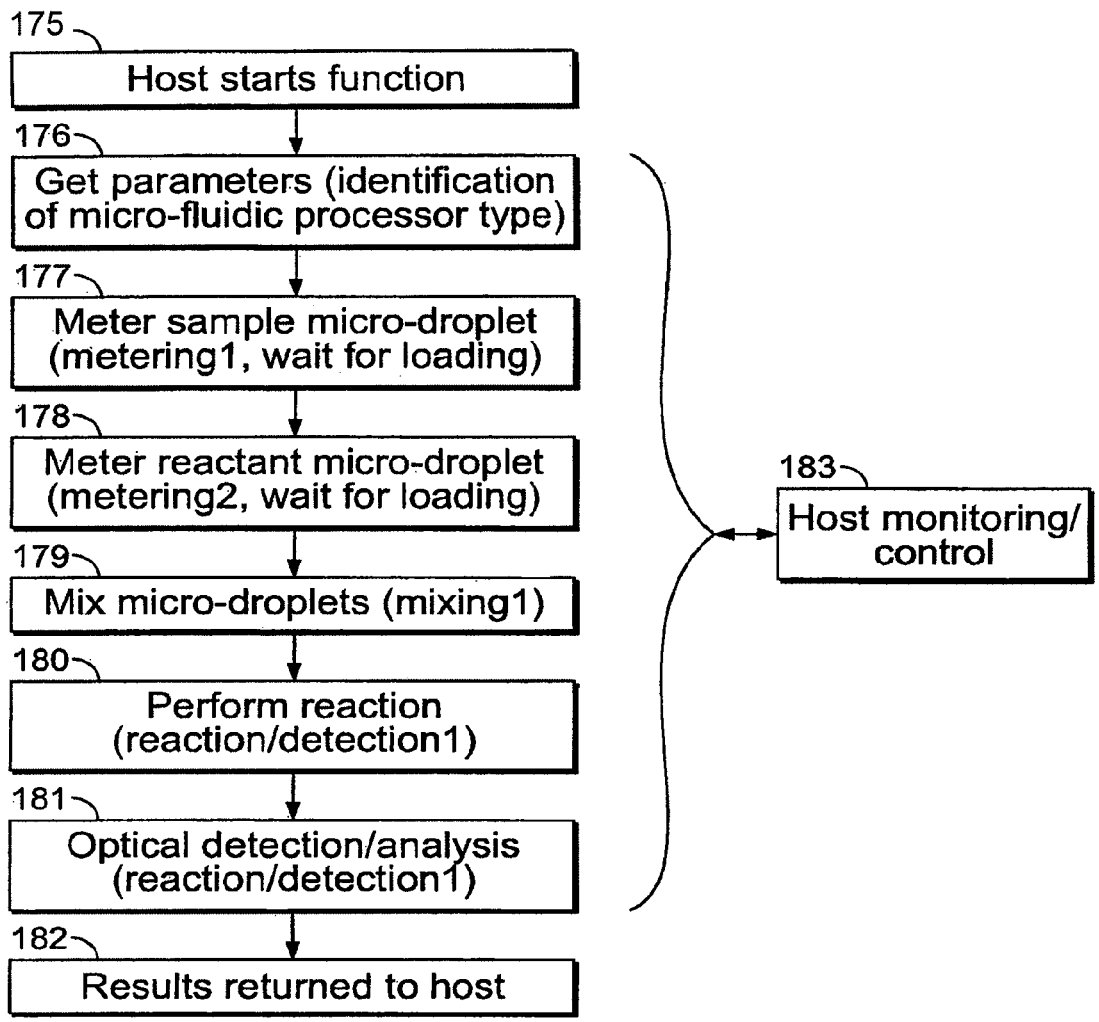
FIG. 12 illustrates an exemplary reaction control function.

In more detail, FIG. 12 illustrates a user-level PCR-reaction-control function, controlled by user commands entered on a host system. Step 175 starts the reaction-control function after a user enters a command at host equipment. Next, steps 177 and 178 obtains input parameters, which include data descriptive of the microfluidic processor on which the reaction is to be performed. As described, this descriptive data may be provided by the microfluidic processor itself, or the processor may provide a key to a database of such data. This function identifies the components, actuators, and sub-assemblies required by subsequent micro-droplet-level functions, and preferably checks that this processor has these correct resources in a correct arrangement. In the microfluidic processor of FIG. 1, these resources are checked and identified as metering1, metering2, mixing1, and reaction/detection1. Next, steps 177 and 178, using the metering micro-droplet-level functions parameterized by the metering1 and metering2 sub-assemblies, meter first and second micro-droplets, including a sample for PCR analysis and reagents. Both metering steps wait (see, for example, FIG. 8D) for a signal indicating the aliquots from which the micro-droplets are metered have been loaded into the processor. Next, step 179 invokes the mixing micro-droplet-level function parameterized by the mixing1 sub-assembly to mix the metered micro-droplets. Since the mixed micro-droplet is now located in the reaction region of the reaction/detection1 sub-assembly, step 180 performs the reaction by invoking the perform-reaction micro-droplet-level function. Lastly, step 181 optically analyzes the reaction results by invoking the sense reaction results actuator-level function. Upon reaction completion, step 182 returns the reaction results and a completion signal to the host system. Throughout the operation of this function, asynchronous host monitoring or control 183 may be in progress, for example, by monitoring the microfluidic processor configuration data as it is updated by the various invoked functions.

Therefore, this exemplary PCR reaction can be specified entirely in terms of high-level micro-droplet functions. Detailed operations of several individual components that must be coordinated to perform this function are generally encapsulated by the micro-droplet functions in which the reaction control is expressed.

In an alternative embodiment, the reaction control function, after obtaining the microfluidic processor description, determines itself which processor components to use to perform the intended reaction. If micro-droplets need to be moved between components that are not directly connected, the control function may insert the necessary micro-droplet move function invocations. This determination is analogous to the layout and wiring of a hardware description expressed in high-level hardware description language (such as VHDL) on a semiconductor chip, and can be performed by similar methods. Further alternatives apparent to one of skill in the art are also included in this invention.

Sample Preparation

The control systems and methods of the present invention are advantageously applied to control microfluidic processors to perform pre-determined analyses of biological and medical samples. Exemplary analyses include determining the presence of certain nucleic acids or proteins that may indicate a disease state of an organism and help in diagnosing the disease state.

Figure 13:
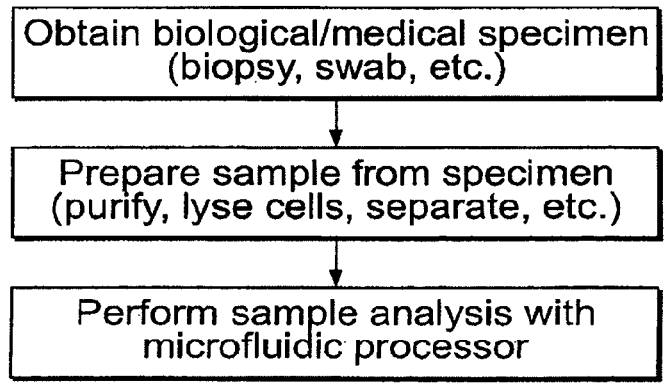
FIG. 13 illustrates an exemplary sample preparation method.

Accordingly, FIG. 13 illustrates the preparation of such samples for analyses. First, a biological or medical specimen is obtained, such as samples obtained from the exterior of an organism, for example, by scraping or swabbing, or from the interior of an organism, for example, by biopsy or surgical specimen. Next a sample is prepared from the specimen. This may include the steps of purifying the specimen from extraneous material (removing cells where extracellular material is to be analyzed), lysing cell (where intracellular materials are to be analyzed), separating the type of material to be analyzed from other types (for example, nucleic acids from proteins). Finally, the prepared sample is loaded into a microfluidic processor for analysis by the systems and methods of this invention.

The invention described and claimed herein is not to be limited in scope by the preferred embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference for all purposes. Further, none of these references, regardless of how characterized above, is admitted as prior to the invention of the subject matter claimed herein.

What is claimed is:

1. A system configured for controlling a microfluidic device, wherein the microfluidic device comprises a micro-channel, a reaction chamber, at least one micro-valve, and at least one heater, the system comprising:
   memory comprising stored instructions, the stored instructions comprising
   at least one actuator level function that controls a group of one or more components to achieve a particular actuator-type function, the at least one actuator level function comprising a close valve actuator level function that identifies a micro-valve to be closed and at least one heater which corresponds to the identified micro-valve to be closed, the close valve actuator level function directing the closing of the at least one micro-valve by directing a change in temperature by the at least one heater corresponding to the micro-valve, and
   a microdroplet level function corresponding to an operation performed on the microfluidic device; and
   an interface configured to receive a user request to perform a desired reaction program, wherein the desired reaction program comprises the microdroplet level function and the microdroplet level function comprises the at least one actuator level function.

2. The system of claim 1, wherein the microdroplet level function corresponds to at least one of a close valve operation, a perform thermal cycling operation, and a detect reaction products operation.

3. The system of claim 1, wherein the stored instructions further comprise a generate pressure actuator level function that identifies a micro-valve to be closed and a reservoir which corresponds to the identified micro-valve to be closed.

4. The system of claim 2, wherein the generate pressure actuator level directs heating of a gas in the reservoir to increase pressure of the gas in the reservoir.

5. The system of claim 1, wherein the stored instructions further comprise a sense reaction results actuator level function that actuates a light source to illuminate a portion of the reaction chamber and actuates a light detector to detect fluorescence emitted from the reaction chamber.

6. The system of claim 1, wherein the at least one actuator level function comprises at least one component level function that directs the generation of a control signal for an individual component of the one or more components of the microfluidic device.

7. The system of claim 6, wherein the at least one component level function comprises a controlled heating function, and wherein the controlled heating function directs generation of a control signal for the at least one heater which corresponds to the identified micro-valve to be closed.

8. The system of claim 7, wherein the at least one heater applies heat to a plug of inert material in the identified micro-valve in response to the control signal.

9. The system of claim 7, wherein the at least one heater applies heat to a gas in a reservoir of the identified micro-valve in response to the control signal.

10. The system of claim 6, wherein the at least one component level function comprises a sense temperature function, and wherein the sense temperature function directs generation of a control signal for a sensor element associated with the reaction chamber.

11. The system of claim 1, further comprising at least one receptacle for receiving the microfluidic device.

12. A system comprising:
   a microfluidic device comprising a micro-channel, a reaction chamber, at least one micro-valve, and at least one heater;
   memory comprising stored instructions corresponding to a reaction program, the stored instructions comprising
   a micro-valve actuator level function corresponding to the closing of a passage of the micro-channel, and
   a heater component level function corresponding to the controlled heating of the reaction chamber;
   an interface configured for allowing a user to select a desired reaction program for the microfluidic device, wherein the desired reaction program corresponds to a micro-valve actuator level function and a heater component level function; and control circuitry configured for creating and transmitting a control signal responsive to the heater component level function for controlling the heating of the micro-channel.

13. The system of claim 12, wherein the stored instructions further comprise a heater component level function corresponding to the controlled heating of a micro-valve configured to close the passage of the micro-channel.

14. The system of claim 12, wherein the stored instructions further comprise a perform analysis microdroplet level function, the perform analysis microdroplet level function comprising a sense reaction results actuator level function, the sense reaction results actuator level function corresponding to at least one of the actuation of a light source to illuminate a portion of the reaction chamber; and the actuation of a light detector to detect radiation scattered or emitted from the reaction chamber.

15. The system of claim 12, further comprising a programmable digital acquisition unit comprising:

a heater driver circuit;

a temperature sensor driver circuit; and a detection driver circuit, wherein the detection driver circuit passes signals to at least one active component configured to detection reaction products in the reaction chamber.

* * * * *